US005627064A

United States Patent [19]
Hoekstra

[11] Patent Number: 5,627,064
[45] Date of Patent: May 6, 1997

[54] PROTEIN KINASES

[75] Inventor: Merl F. Hoekstra, Shohomish, Wash.

[73] Assignee: The Salk Institute For Biological Studies, La Jolla, Calif.

[21] Appl. No.: 447,500

[22] Filed: May 23, 1995

Related U.S. Application Data

[63] Continuation of Ser. No. 8,001, Jan. 21, 1993, abandoned, which is a continuation-in-part of Ser. No. 728,783, Jul. 3, 1991, abandoned.

[51] Int. Cl.$^6$ .......................... C12N 15/54; C12N 15/63; C12N 5/10; C12N 1/15; C12N 1/21
[52] U.S. Cl. ................ 435/194; 435/254.11; 435/252.3; 435/320.1; 435/325; 435/348; 536/23.2
[58] Field of Search .......................... 536/23.2; 435/194, 435/320.1, 240.1, 254.11, 252.3

[56] References Cited

PUBLICATIONS

Coinfection of insect cells with recombinant baculovirus expressing pp60v-src results in the activation of a serine-specific protein kinase pp90rsk. Vik et al. Proc Natl Acad Sci USA Apr. 1990, 87 (7) pp. 2685–2689.

A newly synthesized selective casein kinase I inhibitor, N–(2–aminoethyl)–5–Chloroquinoline–S–Sulfonamide, and affinity purification of casein kinase I from bovine testis, Chijiwa et al., J. Biol. Chem. 25 Mar. 1989, 264 (9) pp. 4924–4927.

The application of the polymerase chain reaction to cloning members of the protein tyrosine kinase family. Wilks et al. Gene 1989 85 pp. 67–74.

Toda et al. (1987) Cell 50: 277–287.
Szyska et al. (1985) Biochim Biophys. Acta. 838: 171–174.
Hoekstra et al. (1991) J. Cell. Biochem. 15A: 156.
Berger et al. (1987) Methods in Enzym. 152.
Rowles et al. (1991) Proc. Mat. Acad. Sci, USA. 88: 9548–9552.
Robinson et al. (1992) Proc. Nat. Acad Sci, USA 89 28–32.
Wang et al. (1992) Mol. Biol. Cell 3 275–286.
Lathe (1985) J. Mol. Biol. 183: 1–12.
Donella–Deana et al (1985) Biochim Biophys. Acta 829 180–187.
Singh et al (1985 Febs. Letters 190: 84–88).
Uhlmann et al. (1990) Chemical Reviews 90:543–584.
Alani, et al., "A method for gene disruption that allows repeated use of URA3 selection in the construction of multiply disrupted yeast strains", Genetics 116:541–545, 1987.
Arriza, et al., "Cloning of human mineralocorticoid receptor complementary DNA: structural and functional kinship with the glucocorticoid receptor", Science 237:268–275, 1987.
Bohmann, et al., "Human proto–oncogene c–jun encodes a DNA binding protein with structural and functional properties of transcription factor AP–1", Science 238:1386–1392, 1987.
Boyle, et al., "Phosphopeptide mapping and phosphoamino acid analysis by two dimensional separation on thin layer cellulose plates", Meth. Enzymol. 200:110–149, 1991.

Brockman, et al., "Cell cycle–dependent localization of casein kinase I to mitotic spindles", Proc. Natl. Acad. Sci. (USA) 89:9454–9458, 1992.
Cech, et al., "Ribozymes and their medical application", J. Am. Med. Assoc. 260:3030–3034, 1988.
Coffman, et al., "Xotch, the Xenopus homolog of Drosphila Notch", Science 249:1438–1441, 1990.
Cole, et al., "Two DNA repair and recombination genes in Saccharomyces cerevisiae, RAD52, and RAD54, are induced during meiosis", Mol. Cell. Biol. 9:3101–3103, 1989.
Colicelli, et al., "Isolation and characterization of a mammalian gene encoding a high–affinity cAMP phosphodiesterase", PNAS 86:3599–3603 (1989).
Courey, et al., "Analysis of Sp1 In Vivo multiple transcriptional domains, including a novel glutamine–rich activation motif", Cell 55:887–898, 1988.
DeMaggio, et al., "The budding yeast HRR25 gene product is a casein kinase I isoform", Proc. Natl. Acad. Sci. (USA) 89:7008–7012 (1992).
Devereux, et al., "A comprehensive set of sequence analysis programs for the VAX", Nucl. Acids Res. 12:387–395, 1984.
Fikes, et al., "Striking conservation of TFIID in Schizosaccharomyces pombe and Saccharomyces cerevisiae", Nature 346:291–294, 1990.
Fraley, et al., "New generation liposomes: the engineering of an efficient vehicle for intracellular delivery of nucleic acids", TIBS 6:77–80, 1981.
Game, "Radiation–sensitive mutants and repair in yeast", in Yeast Genetics: Fundamental & Applied Aspects, pp. 109–137, 1983.
Hanks, et al., "The protein kinase family: conserved features and deduced phylogeny of the catalytic domains", Science 241:42–52, 1988.
Haynes, et al., "DNA repair and mutagenesis in yeast" in Molecular Biology of the Yeast Saccharoyces, pp. 371–414, 1981.
Heinemann, et al., "Bacterial conjugation plasmids mobilize DNA transfer between bacteria and yeast", Nature 340:205–209, 1989.
Hidaka, et al., "Properties and use of H–series compounds as protein kinase inhibitors", Meth. Enzymol. 201:328–339, 1991.
Hoekstra, et al., "Shuttle mutagenesis: bacterial transposons for genetic manipulations in yeast", Meth. Enzymol. 194:329–342, 1991.

(List continued on next page.)

Primary Examiner—Robert A. Wax
Assistant Examiner—Gabriele E. Bugaisky
Attorney, Agent, or Firm—Marshall, O'Toole, Gerstein, Murray & Borun

[57] ABSTRACT

Protein kinase mutant and wild-type genes encoding polypeptides of the class heretofore designated "casein kinase I" and useful in screening compositions which may affect DNA double-strand break repair activity are disclosed. Also disclosed are methods using the polynucleotides in cell-proliferative disorders.

11 Claims, 3 Drawing Sheets

OTHER PUBLICATIONS

Hoekstra, et al., "HRR25, a putative protein kinase from budding yeast: association with repair of damaged DNA", Science 253:1031–1034, 1991.

Huisman, et al., "A Tn10-lacZ-kanR-URA3 gene fusion transposon for insertion mutagenesis and fusion analysis of yeast and bacterial genes," Genetics 116:191–199, 1987.

Hunter, et al., "Transforming gene product of Rous sarcoma virus phosphorylates tyrosine," Proc. Natl. Acad. Sci. (USA) 77:1311–1315, 1980.

Hutter, et al., "Microbial determination by flow cytometry," J. Gen. Microbiol. 113:369–372, 1979.

Ito, et al., "Transformation of intact yeast cells treated with alkali cations," J. Bacteriol. 153:163–168, 1983.

Koerner, et al., "High-expression vectors with multiple cloning sites for construction of $_{trp}$E fusion genes: pATH vectors," Meth. Enzymol. 194:477–490, 1991.

Kohler, et al., "Continuous cultures of fused cells secreting antibody of predefined specificity," Nature 256:495–497, 1975.

Kostriken, et al., "The product of the HO gene is a nuclease: purification and characterization of the enzyme," Cold Spring Harbor Symp. Quant. Biol. 49:89–96, 1984.

Lee, et al., "Complementation used to clone a human homologue of the fission yeast cell cycle control gene cdc2," Nature 327:31–35, 1987.

Lindberg, et al., "cDNA cloning and characterization of eck, an epithelial cell receptor protein-tyrosine kinase in the eck/elk family of protein kinases," Mol. Cell. Biol. 10:6316–6324, 1990.

Maniatis, et al., Molecular Cloning: A Laboratory Manual, pp. 51–53, 109–112, 1982.

Mannino, et al., "Liposome mediated gene transfer," Biotechniques 6:682, 1988.

Marcus-Sekura, "Techniques for using anti-sense oligodeoxyribonucleotides to study gene expression," Anal. Bioch. 172:289–295, 1988.

Matsushime, et al., "A novel mammalian protein kinase gene (mak) is highly expressed in testicular germ cells at and after metaphase,"Mol. Cell. Biol. 10:2261–2268, 1990.

Maundrell, "nmt 1 of fission yeast," J. Biol. Chem. 265:10857–10864, 1990.

Moreland, et al., "Amino acid sequences that determine the nuclear localization of yeast histone 2B," Mol. Cell. Biol. 7:4048–4057, 1987.

Moreno, et al., "Molecular genetic analysis of fission yeast Schizosaccharomyces pombe," Meth.Enzymol. 194:795–823, 1991.

Nickoloff, et al., "Double-strand breaks stimulate alternative mechanisms of recombination repair," J.Mol. Biol. 207:527–541, 1989.

Rose, et al., "A Saccharomyces cerevisiae genomic plasmid bank based on a centromere-containing shuttle vector, "Gene 60:237–243, 1987.

Roussou, et al., "Transcriptional-translational regulatory circuit in Saccharomyces cerevisiae which involves the GCN4 transcriptional activator and GCN2 protein kinase," Mol. Cell. Biol. 8:2132–2139, 1988.

Silver, et al., "Yeast proteins that recognize nuclear localization sequences," J. Cell. Biol. 109:983–989, 1989.

Tuazon, et al., "Casein kinase I and II—multipotential serine protein kinases: structure, function, and regulation," Adv.Sec.Mess. & Phosphoprotein Res. 23:123–164, 1991.

Wharton, et al., "opa: a novel family of transcribed repeats shared by the Nothc locus and other developmentally regulated loci in D. melanogaster," Cell 40:55–62, 1985.

Weintraub,"Antisense RNA and DNA," Sci.Am. 262:40–46, 1990.

Williamson, et al., "The use of fluorescent DNA-binding agent for detecting and separating yeast mitochondrial DNA, "Meth. Cell. Biol. 12:335–351, 1975.

```
Hrr25       ------------MDLRVGRKFRIGRKIGSGSFGDIYHGTNLISG----------------------EEVA
Yck1/Cki2   ----SSRDDSTIIGLHYKIGKKIGEGSFGVLFEGTNMING-----------------------VPVA
Yck2/Cki1   -SGSQSRDDSTIIGLHYKIGKKIGEGSFGVLFEGTNMING-----------------------LPVA
Nuf1        --MSQRSSQHIVGIHYAVGPKIGEGSFGVIFEGENILHSCQAQTGSKRDSSIIMANEPVA
Hhp1        ------MALDLRIGNKYRIGRKIGSGSFGDIYLGTNVVSG-----------------------EEVA
Hhp2        ------MTVVDIKIGNKYRIGRKIGSGSFGQIYLGLNTVNG-----------------------EQVA
CKIα1Hu     MASSSGSKAEFIVGGKYKLVRKIGSGSFGDIYLAINITNG-----------------------EEVA
CKIα2Hu     MASSSGSKAEFIVGGKYKLVRKIGSGSFGDIYLAINITNG-----------------------EEVA
CKIα3Hu     MASSSGSKAEFIBGGKYKLVRKIGSGSFGDIYLAINITNG-----------------------EEVA
Common      ------G-KYKIGRKIGSGSFGDIY--GTN--NG-----------------------E--VA Hrr25       IKLESIRSRHPQLDYESRVYRYLSGGVGIPFIRWFGREGEYNAMVIDLLGPSLEDLFNYCH
Yck1/Cki2   IKFEPRKTEAPQLRDEYKTYKILNGTPNIPYAYYFGQEGLHNILVIDLLGPSLEDLFDWCG
Yck2/Cki1   IKFEPRKTEAPQLKDEYRTYKILAGTPGIPQEYYFGQEGLHNILVIDLLGPSLEDLFDWCG
Nuf1        IKFEPRHSDAPQLRDEFRAYRILNGCVGIPHAYYFGQEGMHNILIDLLGPSLEDLFEWCN
Hhp1        IKLESTRAKHPQLEYEYRVYRILSGGVGIPFVRWFGVECDYNAMVMDLLGPSLEDLFNFCG
Hhp2        VKLEPLKARHHQLEYEFRVYNILKGNIGIPTIRWFGVTNSYNAMVMDLLGPSLEDLFCYCG
CKIα1Hu     VKLESQKARHPQLLYESKLYKILQGGVGIPHIRWYGQEKDYNVLVMDLLGPSLEDLFNFCS
CKIα2Hu     VKLESQKARHPQLLYESKLYKILQGGVGIPHIRWYGQEKDYNVLVMDLLGPSLEDLFNFCS
CKIα3Hu     VKLESQKARHPQLLYESKLYKILQGGVGIPHIRWYGQEKDYNVLVMDLLGPSLEDLFNFCS
Common      IKLEP-KA-HPQL-YE-RVYKIL-G-VGIP--RWFG---G-YNALVIDLLGPSLEDLF--CG Hrr25       RRFSFKTVIMLALQMFCRIQYIHGRSFIHRDIKPDNFLMG--VGRRGST---------
Yck1/Cki2   RKFSVKTVVQVAVQMITLIEDLHAHDLIYRDIKPDNFLIGRPGQPDANN---------
Yck2/Cki1   RRFSVKTVLLLADQLITLIEDLHAHDLIYRDIKPDNFLIGRPGQPDANK---------
Nuf1        RKFSVKTTCMVAKQMIDRVRAIHDHDLIYRDIKPDNFLISQYQRISPEGKVIKSCASSNN
Hhp1        RKFSLKTVLLLADQLISRIEFIHSKSFLHRDIKPDNFLM---IGKRGNQ---------
Hhp2        RKFTLKTVLLLADQLISRIEYVHSKSFLHRDIKPDNFLM---KKHSNV---------
CKIα1Hu     RRFTMKTVLMLADQMISRIEYVHTKNFIHRDIKPDNFLMG--IGRHCNK---------
CKIα2Hu     RRFTMKTVLMLADQMISRIEYVHTKNFIHRDIKPDNFLMG--IGRHCNK---------
CKIα3Hu     RRFTMKTVLMLADQMISRIEYVHTKNFIHRDIKPDNFLMG--IGRHCNKCLESPVGKRKRS
Common      RRFS-KTVLMLADQMISRIEYIH--DFIHRDIKPDNFLMG---G---N---------

Hrr25       ------------VHVIDFGLSKKYRDFNTHRHIPYRENKSLTGTARYASVNTHLGIE
Yck1/Cki2   ------------IHLIDFGMAKQYRDPKTKQHIPYREKKSLSGTARYMSINTHIGRE
Yck2/Cki1   ------------VHLIDFGMAKQYRDPKTKQHIPYREKKSLSGTARYMSINTHIGRE
Nuf1        NDPNL-------IYMVDFGMAKQYRDPRTKQHIPYRERKSLSGTARYMSINTHFGRE
Hhp1        ------------VNIIDFGLAKKYRDHKTHLHIPYRENKNLTGTARYASINTHLGIE
Hhp2        ------------VTMIDFGLAKKYRDFKTHVHIPYRDNKNLTGTARYASINTHLGIE
CKIα1Hu     ------------LFLIDFGLAKKYRDNRTRQHIPYREDKNLTGTARYASINAHLGIE
CKIα2Hu     ------------LFLIDFGLAKKYRDNRTRQHIPYREDKNLTGTARYASINAHLGIE
CKIα3Hu     MTVSTSQDPSFSGLNQLFLIDFGLAKKYRDNRTRQHIPYREDKNLTGTARYASINAHLGIE
Common      ------------VHLIDFGLAKKYRDPKTHQHIPYRENKSLTGTARYASINTHLGIE
```

FIGURE 2A

```
Hrr25      QSRRDDLESLGYVLIYFCKGSLPWQGLKATTKKQKYDRIMEKKLNVSVETLCSGLPL--EF
Yck1/Cki2  QSRRDDMEALGHVFFYFLRGHLPWQGLQAPNNKQKYEKIGEKKRLTNLYDLAQGLPV--QF
Yck2/Cki1  QSRRDDMEAMGHVFFYFLRGQLPWQGLQAPNNKQKYEKIGEKKRLTNLYDLAQGLPI--QF
Nuf1       QSRRDDLESLGHVFFYFLRGSLPWQGLKAPNNKLKYEKIGMTKQKLNPDDLLLNNAIPYQF
Hhp1       QSRRDDLESLGYVLVYFCRGSLPWQGLAATTKKQKYEKIMEKKISTPTEVLCRGFPQ--EF
Hhp2       QSRRDDLESLGYVLLYFCRGSLPWQGLQADTKEQKYQRIRDTKIGTPLEVLCKGLPE--EF
CKIα1Hu    QSRRDDMESLGYVLMYFNRTSLPWQGLKAATKKQKYEKISEKKMSTPVEVLCKGFPA--EF
CKIα2Hu    QSRRDDMESLGYVLMYFNRTSLPWQGLKAATKKQKYEKISEKKMSTPVEVLCKGFPA--EF
CKIα3Hu    QSRRDDMESLGYVLMYFNRTSLPWQGLKAPTKKQKYEKIGEKK--T-LEVLC-GLP---EF
Common     QSRRDDMESLGYVL-YF-RGSLPWQGLKAPTKKQKYEKIGEKK--T-LEVLC-GLP---EF Hrr25      -QEYMAYCKNLKFDEKPDYLFLARLFKDLSIKLEYHNDHLFDWTMLRYTKAMVE
Yck1/Cki2  GRYLEIVERSLSFEECPDYEGYRKLLLSVLDDLGETADGQYDWMKLNDGRG
Yck2/Cki1  GRYLEIVERNLSFEETPDYEGYRMLLLSVLDDLGETADGQYDWMKLNGGRG
Nuf1       -ATYLKYARSLKFDEDPDYDYLLISLMDDALRLNDLKDDGHYDWMDLNGGKG
Hhp1       -SIYLNYTRSLRFDDKPDAYFRKRLRKDFCRQSEEFNYMLFDWTLKRKT
Hhp2       -T-YMCYTRQLSFTEKPNYAYLMKAFRDLLIRKGYQYDYVFDWMILK
CKIα1Hu    -AMYLNYCRGLRFEEAPDYMYLRQLFRILFRTLNHQYDYTFDWTMLKQKAAQQAASSSGQG
CKIα2Hu    -AMYLNYCRGLRFEEAPDYMYLRQLFRILFRTLNHQYDYTFDWTMLKQKAAQQAASSSGQG
CKIα3Hu    -AMYLNYCRGLRFEEAPDYMYLRQLFRILFRTLNHQYDYTFDWTMLKQKAAQQAASSSGQG
Common     ---YL-Y-R-LSFDEKPDY-YLR-LF--LL-------D--FDWT-L-

CKIα1Hu    QQAQTPTGF
CKIα2Hu    QQAQTPTGFKQTDKTKSNMKGF
CKIα3Hu    QQAQTPTGFKQTDKTKSNMKG
```

FIGURE 2B

PROTEIN KINASES

This application is a Continuation of U.S. application Ser. No. 08/008,001, filed Jan. 21,1993, now abandoned, which is a Continuation-In-Part of U.S. application Ser. No. 07/728,783, filed Jul. 3, 1991, now abandoned.

BACKGROUND OF THE INVENTION

1. Field of The Invention

The present invention relates to novel polynucleotides encoding polypeptides which correspond to the class of protein kinase isolates heretofore referred to as casein kinase I and which possess protein kinase and/or DNA recombination/repair promoting functional capabilities.

2. Related Art

A. Protein Kinases

The protein kinases comprise an exceptionally large family of eucaryotic proteins which mediate the responses of cells to external stimuli and are related by amino acid sequence homology within the so-called "catalytic domain" of the enzymes. To date, in excess of 100 unique members of the protein kinase family from a wide variety of eucaryotic organisms have been described and characterized at the amino acid sequence level. See, e.g., Hanks, et al (*Science*, 241:42–52, 1988) which presents a sequence alignment of 65 protein kinase catalytic: domains which range in size from about 250 to 300 amino acids and Hanks, et al. (*Methods in Enzymol.*, 200:38–62, 1991) presenting a catalytic domain sequence alignment for 117 distinct protein kinase family members including a variety of vertebrate, invertebrate, higher plant and yeast species enzymes. The location of the catalytic domain within a protein kinase is not fixed. In most single subunit enzymes, the domain is near the carboxy terminus of the polypeptide while in multimeric protein kinases the catalytic domain takes up almost the entirety of the subunit polypeptide.

Protein kinases are generally classified into a protein-serine/threonine subfamily or a protein-tyrosine subfamily on the basis of phosphorylation substrate specificity. Among the many classes of enzymes within the protein-serine/threonine kinase subfamily are two distinct classes which have been designated casein kinase I and casein kinase II based on the order of their elution from DEAE-cellulose. The casein kinases are distinguished from other protein kinases by their ability to phosphorylate serine or threonine residues within acidic recognition sequences such as found in casein. Tuazon, et al, (*Adv. in Second Messenger and Phosphoprotein Res.*, 23:123–164, 1991) presents a review of over 200 publications related to casein kinase I and II, addressing the physicochemical characterization, recognition sequences, substrate specificity and effects on metabolic regulation for these two classes of enzymes. Casein kinase II is active as a heterotetramer and the complete amino acid sequences of human, rat, Drosophila and yeast species catalytic regions have been determined. Despite the fact that partially purified casein kinase I preparations have been obtained from cell nuclei, cytoplasm, and cell membranes of various plant and animal species, prior to the present invention, nothing was known concerning the primary structure of its enzymatically active monomeric subunit.

As of the time of the present invention, therefore, there existed a significant need in the art for information concerning the primary structure (amino acid sequence) of protein-serine/threonine kinase enzymes of the casein kinase I class. Such information, provided in the form of DNA sequences encoding one or more of these kinases (from which primary structures could be deduced), would allow for the large scale production of kinases by recombinant techniques as well as for determination of the distribution and function of these enzymes, the structural distinctions between membrane-bound and non-membranous forms, the potential ligand-receptor interactions in which these kinases interact, and the identification of agents capable of modulating ligand-receptor binding, kinase, and other activities.

B. DNA Recombination And Repair

Chromosomes experience single-stranded or double-stranded breaks as a result of energy-rich radiation, chemical agents, as well as spontaneous breaks occurring during replication among others. Although genes present in the chromosomes undergo continuous damage, repair, exchange, transposition, and splicing, certain enzymes protect or restore the specific base sequences of the chromosome.

The repair of DNA damage is a complex process that involves the coordination of a large number of gene products. This complexity is in part dependent upon both the form of DNA damage and cell cycle progression. For example, in response to ultraviolet (UV) irradiation, cells can employ photoreactivation or excision repair functions to correct genetic lesions. The repair of strand breaks, such as those created by X-rays, can proceed through recombinational mechanisms. For many forms of DNA damage, the cell is induced to arrest in the G2 phase of the cell cycle. During this G2 arrest, lesions are repaired to ensure chromosomal integrity prior to mitotic segregation.

Since the transfer of genetic information from generation to generation is dependent on the integrity of DNA, it is important to identify those gene products which affect or regulate genetic recombination and repair. Through the use of organisms with specific genetic mutations, the normal functional gene can be obtained, molecularly cloned, and the gene products studied.

In eukaryotes such as Saccharomyces cerevisiae, genetic studies have defined repair-deficient mutants which have allowed the identification of more than 30 radiation-sensitive (RAD) mutants (Haynes, et al, in *Molecular Biology of the Yeast Saccharomyces*, pp. 371, 1981; J. Game in *Yeast Genetics: Fundamental and Applied Aspects*, pp. 109, 1983). These mutants can be grouped into three classes depending upon their sensitivities. These classes broadly define excision-repair, error-prone repair, and recombinational-repair functions. The molecular characterization of yeast RAD genes has increased the understanding of the enzymatic machinery involved in excision repair, as well as the arrest of cell division by DNA damage.

The understanding of RAD genes and their expression products has become increasingly important as research continues to develop more effective therapeutic compositions. Often these new compositions appear quite effective against a particular disease condition, such as certain tumors, but prove to be too toxic for in vivo therapy in an animal having the disease. Indeed, these compositions can actually increase the likelihood of mutagenesis.

Most agents that are mutagenic or carcinogenic are in themselves unreactive, but are broken down to reactive intermediates in vivo. It is these reactive intermediates which interact with DNA to produce a mutation. This event is thought to be the initial step in chemical carcinogenesis. Mutations in a large number of genes affect the cellular response to agents that damage DNA. In all likelihood, many of these mutated genes encode enzymes that participate in DNA repair systems. Consequently, when the repair system is compromised, the cells become extremely sensitive to toxic agents. Although the DNA may revert to normal when DNA repair mechanisms operate successfully, the failure of such mechanisms can result in a transformed tumor cell which continues to proliferate.

Although there are currently available tests to determine the toxicity or mutagenicity of chemical agents and compositions, there are limitations in both laboratory screening procedures and animal toxicity tests. These limitations include extrapolating laboratory data from animals to humans. There is often a large measure of uncertainty when attempting to correlate the results obtained in laboratory animals with effects in human subjects. In most cases, doses of the test drug have been used in the animal which are too high to be safely administered to humans. In addition, some types of toxicity can be detected if the drug is administered in a particular species, yet may be missed if the experiment is not done in the correct animal species. Moreover, many currently available laboratory tests are incapable of detecting certain types of toxic manifestations which occur in man.

Phenotypic complementation, as a way of identifying homologous normal functional genes, is widely used. For example, the human homologue of the yeast cell cycle control gene, cdc 2, was cloned by expressing a human cDNA library in *Schizosaccharomyces pombe* and selecting those clones which could complement a mutation in the yeast cdc 2 gene (Lee, et al., *Nature*, 327:31, 1987). A mammalian gene capable of reverting the heat shock sensitivity of the RAS2$^{val19}$ gene of yeast, has also been cloned by using complementation (Colicelli, et al, *Proc. Nat'l. Acad. Sci. USA*, 86:3599, 1989). A rat brain cDNA library was used to clone a mammalian cDNA that can complement the loss of growth control associated with the activated RAS2 gene in yeast. The gene, DPD (dunce-like phosphodiesterase), encodes a high-affinity CAMP phosphodiesterase.

In summary, limitations and uncertainties of existing laboratory tests fail to provide an accurate method of examining the effects of a composition on DNA integrity. In view of this, a considerable need exists for screening methodologies which are inexpensive, rapid, and contain the relevant gene from the animal which is to be treated with the composition. Such methods provide a direct assay to determine if a composition interferes with the DNA repair system of a cell.

SUMMARY OF THE INVENTION

In one of its aspects, the present invention provides purified and isolated polynucleotides (e.g., DNA sequences and RNA transcripts thereof) encoding eucaryotic protein kinases of the casein kinase I class herein designated as "HRR25-like" proteins and characterized by greater than 35% amino acid sequence homology with the prototypical yeast enzyme HRR25 through the protein kinase catalytic domain thereof. Polynucleotides provided by the invention include RNAs, mRNAs and DNAs, including antisense forms thereof. Preferred DNA sequences of the invention include genomic and cDNA sequences as well as wholly or partially chemically synthesized DNA sequences and biological replicas thereof. Specifically illustrating the invention are *Saccharomyces cerevisiae* DNAs including those encoding HRR25 and NUF 1, *Schizosaccharomyces pombe* DNAs including those encoding Hhp1+ and Hhp2+, and human DNAs including those encoding CKIα1Hu, CKIα2Hu, and CKIα3Hu. Also provided are autonomously replicating recombinant constructions such as plasmid and viral DNA vectors incorporating such sequences and especially vectors wherein DNA encoding an HRR25-like casein kinase I protein is linked to an endogenous or exogenous expression control DNA sequence.

According to another aspect of the invention, host cells, especially unicellular host cells such as procaryotic and eucaryotic cells, are stably transformed with DNA sequences of the invention in a manner allowing the desired polypeptides to be expressed therein. Host cells expressing such HRR25-like products can serve a variety of useful purposes. To the extent that the expressed products are "displayed" on host cell surfaces, the cells may constitute a valuable immunogen for the development of antibody substances specifically immunoreactive therewith.

Host cells of the invention are conspicuously useful in methods for the large scale production of HRR25-like proteins wherein the cells are grown in a suitable culture medium and the desired polypeptide products are isolated from the cells or from the medium in which the cells are grown.

Also comprehended by the present invention are antibody substances (e.g., monoclonal and polyclonal antibodies, single chain antibodies, chimeric antibodies, CDR-grafted antibodies and the like) and other binding proteins which are specific for HRR25-like proteins (i.e., non-reactive with protein kinase molecules which are not related by at least 35% homology with HRR25 through the protein kinase catalytic domain). Antibody substances can be developed using isolated natural or recombinant HRR25-like proteins or cells expressing such products on their surfaces. The antibody substances are useful, in turn, for purifying recombinant and naturally occurring HRR25-like polypeptides and identifying cells producing such polypeptides on their surfaces. The antibody substances and other binding proteins are also manifestly useful in modulating (i.e., blocking, inhibiting, or stimulating) ligand-receptor binding reactions involving HRR25-like proteins. Anti idiotypic antibodies specific for anti-HRR25-like antibody substances are also contemplated. Assays for the detection and quantification of HRR25-like proteins on cell surfaces and in fluids such as serum and cytoplasmic fractions may involve a single antibody substance or multiple antibody substances in a "sandwich" assay format.

Recombinant HRR25-like protein products obtained according to the invention have been observed to display a number of properties which are unique among the eucaryotic protein kinases. As one example, the HRR25 protein possesses both protein-tyrosine kinase and protein-serine/threonine kinase activities. Moreover, HRR25 operates to promote repair of DNA strand breaks at a specific nucleotide sequence and is the only protein kinase known to have such recombination/repair promoting activity.

The DNA sequence information for yeast and mammalian (including human) species HRR25-like proteins which is provided by the present invention makes possible the identification and isolation of DNAs encoding other HRR25-like proteins by such well-known techniques as DNA/DNA hybridization and polymerase chain reaction (PCR) cloning.

Recombinant HRR25-like proteins and host cells expressing the same are useful in screening methods designed to examine the effects of various compositions on DNA break repair and protein kinase activities of the proteins. Protein kinase inhibitory effects may be assessed by well-known screening procedures such as described in Hidaka, et al. (*Methods in Enzymology*, 201:328-339, 1991).

Further aspects and advantages of the present invention will be apparent upon consideration of the following detailed description of presently preferred embodiments thereof, reference being made to the drawing wherein:

FIG. 1(A) presents an alignment of the predicted amino acid sequence of HRR25 with the catalytic domains of the yeast CDC28, yeast KSS1 and human RAF1 protein kinases. FIG. 1(B) shows a schematic representation of the structure of HRR25.

FIG. 2A and 2B presents an alignment of the predicted amino acid sequences of HRR25 with the sequences of three other *Saccharomyces cerevisiae* HRR25-like proteins (YCK1/CKI2, YCK2/CKI1, and NUF1), two HRR25-like proteins (Hhp1+ and Hhp2+) from *Schizosaccharomyces pombe* and three putative isoforms (CKIα1Hu, CKIα2Hu, and CKIα3Hu) of a human HRR25-like protein.

DETAILED DESCRIPTION OF THE PREFERRED EMBODIMENT

Figures 1A, 1B:
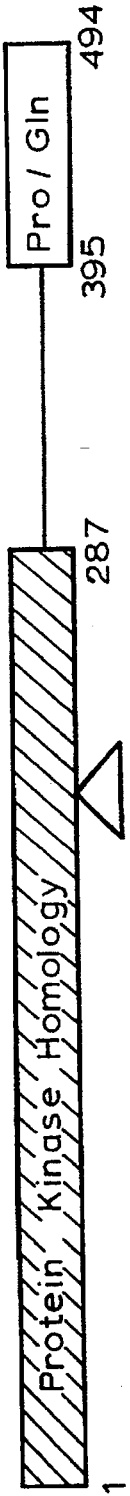

In one of its aspects, the present invention relates to a DNA encoding a recombination/repair promoting polypeptide which can be used in an assay system to examine the effects of various compositions on DNA integrity. 5 These functional sequences, which can be characterized by their ability to promote restoration of DNA strand breaks, permit the screening of compositions to determine whether a particular composition has an effect on the restoration of such repair activity. The invention also provides a DNA sequence encoding a polypeptide which promotes normal mitotic recombination, but is defective in protein kinase activity and essentially unable to repair DNA strand breaks. This defective DNA sequence is highly useful for identifying other DNA sequences which encode proteins with functional protein kinase activity. In addition, the present invention relates to the polypeptide encoded by the defective DNA sequence, as well as the polypeptide encoded by the functional wild-type DNA.

In order to identify a DNA sequence encoding a polypeptide with protein kinase activity, a method is provided whereby a DNA library is screened for nucleotide sequences capable of restoring DNA strand break repair in a mutant lacking such activity. A method is further provided for identifying a composition which affects the activity of a mammalian polypeptide having protein kinase activity, wherein the polypeptide is capable of restoring DNA double-strand break repair activity in a mutant lacking such activity.

In general, the defective protein kinase can be characterized by its ability to promote normal mitotic recombination, while being essentially unable to repair DNA double-strand break including that which occurs at the cleavage site:

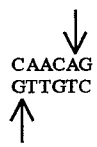

The DNA double-strand breaks which the defective protein kinase is essentially unable to repair can be induced by various means, including endonucleases, x-rays, or radiomimetic agents including alkylating agents. Preferred endonucleases are those which recognize the same nucleotide cleavage site as endonuclease HO. Radiomimetic alkylating agents having methylmethane sulfonate activity are preferred. Those of skill in the art will be able to identify other agents which induce the appropriate DNA strand breaks without undue experimentation.

The present invention specifically discloses mutants sensitive to continuous expression of the DNA double-strand endonuclease HO, which codes for a 65 kDa site-specific endonuclease that initiates mating type interconversion (Kostriken, et al., i Cold Spring Harbor Symp. Quant. Biol, 49:89, 1984). These mutants are important to understanding the functions involved in recognizing and repairing damaged chromosomes. This invention also discloses a yeast wild-type DNA recombination and repair gene called HRR25 (HO and/or radiation repair). Homozygous mutant strains, hrr25-1, are sensitive to methylmethane sulfonate and X-rays, but not UV irradiation. The wild-type gene encodes a novel protein kinase, homologous to other serine/threonine kinases, which appears critical in activation of DNA repair functions by phosphorylation.

The HRR25 kinase is important for normal cell growth, nuclear segregation, DNA repair and meiosis, and deletion of HRR25 results in cell cycle defects. These phenotypes, coupled with the sequence similarities between the HRR25 kinase and the Raf/c-mos protein kinase subgroup suggest that HRR25 might play a similar role in *S. cerevisiae* growth and development. The defects in DNA strand break repair and the aberrant growth properties revealed by mutations in HRR25 kinase, expands the role that protein kinases may play and places HRR25 in a functional category of proteins associated with DNA metabolism.

The development of specific DNA sequences encoding protein kinase polypeptides of the invention can be accomplished using a variety of techniques. For example, methods which can be employed include (1) isolation of a double-stranded DNA sequence from the genomic DNA of the eukaryote; (2) chemical synthesis of a DNA sequence to provide the necessary codons for the polypeptide of interest; and (3) in vitro synthesis of a double stranded DNA sequence by reverse transcription of mRNA isolated from a eukaryotic donor cell. In the latter case, a double stranded DNA complement of mRNA is eventually formed which is generally referred to as cDNA.

The novel DNA sequences of the invention include all sequences useful in providing for expression in prokaryotic or eukaryotic host cells of polypeptides which exhibit the functional characteristics of the novel protein kinase of the invention. These DNA sequences comprise: (a) the DNA sequences as set forth in SEQ. I.D. No. 1 or their complementary strands; (b) DNA sequences which encode an amino acid sequence with at least about 35% homology in the protein kinase domain with the amino acid sequences encoded by the DNA sequences defined in (a) or fragments thereof; and (c) DNA sequences defined in (a) and (b) above. Specifically embraced in (b) are genomic DNA sequences which encode allelic variant forms. Part (c) specifically embraces the manufacture of DNA sequences which encode fragments of the protein kinase and analogs of the protein kinase wherein the DNA sequences thereof may incorporate codons which facilitate translation of mRNA. Also included in part (c) are DNA sequences which are degenerate as a result of the genetic code.

The term "conservative variation" as used herein denotes the replacement of an amino acid residue by another, biologically similar residue. Examples of conservative variations include the substitution of one hydrophobic residue such as isoleucine, valine, leucine or methionine for another, or the substitution of one polar residue for another, such as the substitution of arginine for lysine, glutamic for aspartic acids, or glutamine for asparagine, and the like.

With the DNA sequences of the invention in hand, it is a routine matter to prepare, subclone, and express smaller DNA fragments from this or a corresponding DNA sequences. The term "polypeptide" denotes any sequence of amino acids having the characteristic activity of the mutant or wild-type protein kinase of the invention, wherein the sequence of amino acids is encoded by all or part of the DNA sequences of the invention.

The polypeptide resulting from expression of the DNA sequence of the invention can be further characterized as being free from association with other eukaryotic polypeptides or other contaminants which might otherwise be associated with the protein kinase in its natural cellular environment.

Isolation and purification of microbially expressed polypeptides provided by the invention may be by conventional means including, preparative chromatographic separations and immunological separations involving monoclonal and/or polyclonal antibody preparation.

In general, recombinant expression vectors useful in the present invention contain a promotor sequence which facilitates the efficient transcription of the inserted eukaryotic genetic sequence. The expression vector typically contains an origin of replication, a promoter, and a terminator, as well as specific genes which are capable of providing phenotypic selection of the transformed cells. The transformed hosts can be grown in fermentors and cultured according to techniques known in the art to achieve optimal cell growth. The polypeptides of the invention can then be isolated from the growth medium, cellular lysates, or cellular membrane fractions.

The DNA sequences of the present invention can be expressed in vivo in either prokaryotes or eukaryotes. Methods of expressing DNA sequences containing eukaryotic coding sequences in prokaryotes are well known in the art. Biologically functional viral and plasmid DNA vectors used to incorporate DNA sequences of the invention, for expression and replication in the host cell are well known in the art. For example, DNA can be inserted in yeast using appropriate vectors and introducing the product into the host cells. Various shuttle vectors for the expression of foreign genes in yeast have been reported (Heinemann, et al, *Nature*, 340:205, 1989; Rose, et al, *Gene*, 60:237, 1987). Those of skill in the art will know of appropriate techniques for obtaining gene expression in both prokaryotes and eukaryotes, or can readily ascertain such techniques, without undue experimentation.

Hosts include microbial, yeast, insect and mammalian host organisms. Thus, the term "host" is meant to include not only prokaryotes, but also such eukaryotes such as yeast, filamentous fungi, as well as plant and animal cells which can replicate and express an intron-free DNA sequence of the 5 invention. The term also includes any progeny of the subject cell. It is understood that not all progeny are identical to the parental cell since there may be mutations that occur at replication. However, such progeny are included when the terms above are used.

Transformation with recombinant DNA may be carried out by conventional techniques well known to those skilled in the art. Where the host is prokaryotic, such as *E. coli*, competent cells which are capable of DNA uptake can be prepared from cells harvested after exponential growth phase and subsequently treated by the $CaCl_2$ method using procedures well known in the art. Alternatively, $MgCl_2$ or RbCl could be used in the reaction. Transformation can also be performed after forming a protoplast of the host cell.

Where the host is a eukaryote, various methods of DNA transfer can be used. These include transfection of DNA by calcium phosphate-precipitates, conventional mechanical procedures such as microinjection, insertion of a plasmid encased in liposomes, spheroplast electroporation, salt mediated transformation of unicellular organisms or the use of virus vectors. Analysis of eukaryotic DNA has been greatly simplified since eukaryotic DNA can be cloned in prokaryotes using vectors well known in the art. Such cloned sequences can be obtained easily in large amounts and can be altered in vivo by bacterial genetic techniques and in vitro by specific enzyme modifications. To determine the effects of these experimentally induced changes on the function and expression of eukaryotic genes, the rearranged sequences must be taken out of the bacteria in which they were cloned and reintroduced into a eukaryotic organism. Since there are still many functions in eukaryotic cells which are absent in prokaryotes, (e.g., localization of ATP-generating systems to mitochondria, association of DNA with histones, mitosis and meiosis, and differentiation of cells), the genetic control of such functions must be assessed in a eukaryotic environment. Cloning genes from other eukaryotes in yeast has been useful for analyzing the cloned eukaryotic genes as well as other yeast genes. A number of different yeast vectors have been constructed for this purpose. All vectors replicate in *E. coli*, which is important for amplification of the vector DNA. All vectors contain markers, e.g., LEU 2, HIS 3, URA 3, that can be selected easily in yeast. In addition, these vectors also carry antibiotic resistance markers for use in *E. coli*.

Many strategies for cloning human homologues of known yeast genes are known in the art. These include, but are not limited to: 1) low stringency hybridization to detect shared nucleotide sequences; 2) antibody screening of expression libraries to detect shared structural features; and 3) complementation of mutants to detect genes with similar functions.

For purposes of the present invention, protein kinases which are homologous can be identified by structural as well as functional similarity. Structural similarity can be determined, for example, by assessing amino acid homology or by screening with antibody, especially a monoclonal antibody, which recognizes a unique epitope present on the protein kinases of the invention. When amino acid homology is used as criteria to establish structural similarity, those amino acid sequences which have homology of at least about 35% in the protein kinase domain with the prototypical HRR25 protein are considered to uniquely characterize polypeptides.

Conserved regions of amino acid residues in HRR25 can be used to identify HRR25-like genes from other species. Conserved regions which can be used as probes for identification and isolation of HRR25-like genes (homologues) include the nucleotides encoding amino acid sequences GPSLED, RDIKPDNFL, HIPYRE, and SVN, for example. These conserved motifs can be used, for example, to develop nucleotide primers to detect other HRR25-like genes by methods well known to those skilled in the art, such as polymerase chain reaction (PCR).

When homologous amino acid sequences are evaluated based on functional characteristics, then a homologous amino acid sequence is considered equivalent to an amino acid sequence of the invention when the homologous sequence is essentially unable to repair (in the case of the repair defective mutant gene) or able to repair (in the case of the natural gene), DNA double-strand breaks, including that which occurs at a nucleotide cleavage site

and when the homologous amino acid sequence allows normal mitotic recombination.

This invention provides screening methods whereby genes are cloned from plasmid libraries by complementation of a recessive marker. A recipient strain such as *Saccharomyces cerevisiae* is constructed that carries a recessive mutation in the gene of interest. This strain is then transformed with a plasmid, for example, pYES2 (Invitrogen, San Diego, Calif.) containing the wild-type genomic DNA or cDNA. The clone carrying the gene of interest can then be selected by replica plating to a medium that distinguishes mutant from wild-type phenotypes for the gene of interest. The plasmid can then be extracted from the clone and the DNA studied. Several yeast vectors allow the application of complementation systems to go beyond isolation of yeast genes. Genes from a wide variety of species can be isolated using these vectors. In such systems, DNA sequences from any source are cloned into a vector and can be screened directly in yeast for activities that will complement specific yeast mutations.

In a preferred embodiment, the present invention uses a mutation in yeast, the hrr25 mutation, which was identified by sensitivity to DNA double-strand breaks induced by the HO endonuclease. The genomic DNA which complements this mutation was isolated by transforming the hrr25 strain with a DNA library and subsequently screening for methylmethane sulfonate (MMS) resistance. Alternately, functional genes from a variety of mammalian species can now be cloned using the system described.

Yeast genes can be cloned by a variety of techniques, including use of purified RNA as hybridization probes, differential hybridization of regulated RNA transcripts, antibody screening, transposon mutagenesis, cross suppression of mutant phenotypes, cross hybridization with heterologous cDNA or oligonucleotide probes, as well as by complementation in *E. coli*.

Minor modifications of the primary amino acid sequence may result in proteins which have substantially equivalent or enhanced activity as compared to the sequence set forth in SEQ. I.D. NO. 2. The modifications may be deliberate, as by site-directed mutagenesis, or may be spontaneous by HRR25 producing organisms. All of these modifications are included in the invention as long as HRR25 activity is retained. Substitution of an aspartic acid residue for a glycine acid residue at position 151 in the sequence shown in SEQ. I.D. NO. 2 identifies the mutant hrr25.

Antibodies provided by the present invention are immunoreactive with the mutant polypeptides and/or the naturally occurring protein kinase. Antibody which consist essentially of numerous monoclonal antibodies with different epitopic specificities, as well as distinct monoclonal antibody preparations are provided. Monoclonal antibody is made from antigen containing fragments of the polypeptide by methods well known in the art (Kohler, G. et al, *Nature* 2,56:495, 1975; *Current Protocols in Molecular Biology*, Ausubel, F. et al., ed.,1989).

The invention also discloses a method for identifying a composition which 15 affects the activity of a polypeptide having tyrosine kinase activity. The polypeptide is capable of promoting restoration of DNA double-strand break repair activity in host cells containing the hrr25 gene. The composition and the polypeptide are incubated in combination with host cells for a period of time and under conditions sufficient to allow the components to interact, then subsequently monitoring the change in protein kinase activity, for example, by decreased repair of DNA double-strand breaks. The DNA strand breaks are induced, for example, by a radiomimetic agent, such as methylmethane sulfonate, x-rays, or by endonuclease like HO. Other means of inducing double-strand breaks that are well known in the art may be employed as well.

One embodiment of the invention provides a method of treating a cell proliferative disorder associated with or HRR25 or an HRR25-like protein comprising administering to a subject with the disorder, a therapeutically effective amount of reagent which modulates an HRR25-like protein activity. The term "cell proliferative disorder" denotes malignant as well as nonmalignant cell populations which differ from the surrounding tissue both morphologically and/or genotypically. Such disorders may be associated, for example, with abnormal expression of HRR25-like protein genes. "Abnormal expression" encompasses both increased or decreased levels of expression as well as expression of mutant forms such that the normal function of HRR25-like genes is altered. Abnormal expression also includes inappropriate temporal expression during the cell cycle or expression in an incorrect cell type. Antisense polynucleotides of the invention are useful in treating malignancies of the various organ systems. Essentially, any disorder which is etiologically linked to altered expression of HRR25-like genes is a candidate for treatment with a reagent of the invention. "Treatment" of cell proliferative disorder refers to increasing or decreasing populations of malignant or non-malignant cells.

As used herein, the term "modulate" envisions the suppression of HRR25-like protein expression or the augmentation of expression. When a cell proliferative disorder is associated with HRR25-like gene overexpression, appropriate reagents such as antisense or binding antibody can be introduced to a cell. This approach utilizes, for example, antisense nucleic acid and ribozymes to block translation of a specific HRR25-like protein mRNA, either by masking that mRNA with an antisense nucleic acid or by cleaving it with a ribozyme. Alternatively, when a cell proliferative disorder is associated with insufficient HRR25-like protein, a sense polynucleotide sequence (the DNA coding strand) or HRR25-like polypeptide can be introduced into the cell by methods known in the art.

As used herein, the term "therapeutically effective" refers to that amount of polynucleotide, antibody or polypeptide that is sufficient to ameliorate the HRR25-associated disorder. "Ameliorate" denotes a lessening of the detrimental effect of the HRR25-associated disorder in the subject receiving therapy.

Antisense nucleic acids are DNA or RNA molecules that are complementary to at least a portion of a specific mRNA molecule (Weintraub, *Scientific American*, 262:40, 1990). In the cell, the antisense nucleic acids hybridize to the corresponding mRNA, forming a double-stranded molecule. This interferes with the translation of the mRNA since the cell will not translate a mRNA that is double-stranded. Antisense oligomers of about 15 nucleotides are preferred, since they are easily synthesized and are less likely to cause non-specific interference with translation than larger molecules when introduced into the target HRR25 producing cell. The use of antisense methods to inhibit the in vitro translation of genes is well known in the art (Marcus-Sakura, *Anal. Biochem.*, 172:289, 1988).

Ribozymes are RNA molecules possessing the ability to specifically cleave other single-stranded RNA in a manner analogous to DNA restriction endonucleases. Through the modification of nucleotide sequences which encode these RNAs, it is possible to engineer molecules that recognize specific nucleotide sequences in an RNA molecule and cleave it (Cech, *J. Amer. Med. Assn.*, 260:3030, 1988). A major advantage of this approach is that, because ribosomes are sequence-specific, only mRNAs with particular sequences are inactivated.

There are two basic types of ribozymes namely, tetrahymena-type and "hammerhead"-type. Tetrahymena-type ribozymes recognize sequences which are four bases in length, while "hammerhead"-type ribozymes recognize base sequences 11–18 bases in length. The longer the recognition sequence, the greater the likelihood that that sequence will occur exclusively in the target mRNA species. Consequently, hammerhead-type ribozymes are preferable to tetrahymena-type ribozymes for inactivating a specific mRNA species and longer recognition sequences are preferable to shorter recognition sequences.

The present invention also provides gene therapy for the treatment of cell proliferative disorders which are mediated by HRR25-like polypeptides. Such therapy comprises introducing into cells of subjects having the proliferative disorder, the HRR25-like antisense polynucleotide. Delivery of antisense polynucleotide can be achieved using a recombinant expression vector such as a chimeric virus or a colloidal dispersion system. Disorders associated with under-expression of HRR25 can similarly be treated using gene therapy with nucleotide coding sequences.

Various viral vectors which can be utilized for gene therapy as taught herein include adenovirus, herpes virus, vaccinia, or, preferably, an RNA virus such as a retrovirus. Preferably, the retroviral vector is a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). A number of additional retroviral vectors can incorporate multiple genes. All of these vectors can transfer or incorporate a gene for a selectable marker so that transduced cells can be identified and generated. By inserting an HRR25-like sequence of interest into the viral vector, along with another gene which encodes the ligand for a receptor on a specific target cell, for example, the vector is now target specific. Retroviral vectors can be made target specific by inserting, for example, a polynucleotide encoding a sugar, a glycolipid, or a protein. Preferred targeting is accomplished by using an antibody to target the retroviral vector. Those of skill in the art will know of, or can readily ascertain without undue experimentation, specific polynucleotide sequences which can be inserted into the retroviral genome to allow target specific delivery of the retroviral vector containing the HRR25-like antisense polynucleotide.

Since recombinant retroviruses are defective, they require assistance in order to produce infectious vector particles. This assistance can be provided, for example, by using helper cell lines that contain plasmids encoding all of the structural genes of the retrovirus under the control of regulatory sequences within the LTR. These plasmids are missing a nucleotide sequence which enables the packaging mechanism to recognize an RNA transcript for encapsidation. Helper cell lines which have deletions of the packaging signal include but are not limited to Ψ2, PA317 and PA12, for example. These cell lines produce empty virions, since no genome is packaged. If a retroviral vector is introduced into such cells in which the packaging signal is intact, but the structural genes are replaced by other genes of interest, the vector can be packaged and vector virion produced. Alternatively, NIH 3T3 or other tissue culture cells can be directly transfected with plasmids encoding the retroviral structural genes gag, pol and env, by conventional calcium phosphate transfection. These cells are then transfected with the vector plasmid containing the genes of interest. The resulting cells release the retroviral vector into the culture medium.

Another targeted delivery system for HRR25-like antisense polynucleotides comprises a colloidal dispersion system. Colloidal dispersion systems include macromolecule complexes, nanocapsules, microspheres, beads, and lipid-based systems including oil-in-water emulsions, micelles, mixed micelles, and liposomes. The preferred colloidal system of this invention is a liposome. Liposomes are artificial membrane vesicles which are useful as delivery vehicles in vitro and in vivo. It has been shown that large unilamellar vesicles (LUV), which range in size from 0.2–4.0 um can encapsulate a substantial percentage of an aqueous buffer containing large macromolecules. RNA, DNA and intact virions can be encapsulated within the aqueous interior and be delivered to cells in a biologically active form (Fraley, et al., *Trends Biochem. Sci.*, 6:77, 1981). In addition to mammalian cells, liposomes have been used for delivery of polynucleotides in plant, yeast and bacterial cells. In order for a liposome to be an efficient gene transfer vehicle, the following characteristics should be present: (1) encapsulation of the genes of interest at high efficiency while not compromising their biological activity; (2) preferential and substantial binding to a target cell in comparison to non-target cells; (3) delivery of the aqueous contents of the vesicle to the target cell cytoplasm at high efficiency; and (4) accurate and effective expression of genetic information (Mannino, et al, *Biotechniques*, 6:682, 1988).

The targeting of liposomes has been classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticuloendothelial system (RES) in organs which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted delivery system may be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand.

In general, the compounds bound to the surface of the targeted delivery system will be ligands and receptors which will allow the targeted delivery system to find and "home in" on the desired cells. A ligand may be any compound of interest which will bind to another compound, such as a receptor.

The present invention will be better understood upon consideration of the following illustrative examples wherein: Example 1 addresses isolation of hrr25 mutant strains of *Saccharomyces cerevisiae*; Example 2 describes the isolation of HRR25 DNA by complementation screening; Example 3 is drawn to characterization of the DNA and putative amino acid sequence of HRR25; Example 4 addresses microscopic analysis of HRR25 wild type and hrr25 mutant yeast morphology; Example 5 addresses the relationship of the amino acid sequence of HRR25 and three exemplary protein kinases which are not HRR25-like; Example 6 describes the isolation of DNAs encoding two *Schizosaccharomyces pombe* HRR25-like protein kinases; Example 7 is directed to isolation of DNA encoding another *Saccharomyces cerevisiae* protein, NUF1; Example 8 is drawn to isolation of DNAs encoding various eucaryotic species HRR25-like proteins incuding three human isoforms, CKIα1Hu, CKIα2Hu, and CKIα3Hu; Examples 9 and 10 are respectively directed to determination of casein kinase and both serine-theonine kinase and tyrosine kinase activities for HRR25; and Example 11 is drawn to the recombinant expression of HRR25 products and the generation of antibodies thereto.

The following examples are intended to illustrate but not limit the invention. While they are typical of those that might be used, other procedures known to those skilled in the art may alternatively be used.

EXAMPLE 1

Isolation of hrr25

*S. cerevisiae* strain K264-5B (MATαho ura3 can $1^R$ tyr1 his 7 lys2 ade5 met13 trp5 leu1 ade5) was employed for the mutant isolation. The yeast were transformed according to standard procedures with a URA3-based integrating plasmid that contained a GAL1,10-regulated HO endonuclease and a transformant was mutagenized to approximately 50% survival with ethyl methanesulfonate (EMS), as described (*Current Protocols in Molecular Biology*, supra). The culture was spread onto glycerol-containing rich medium (YPG, to avoid petites), colonies were allowed to form at 30° C., and plates were replicated to glucose (HO repressing) and galactose (HO inducing) media. Mutants were identified by their inability to grow on galactose. Approximately 200 mutants were chosen for initial characterization and 62 maintained the gal- phenotype through repeated single colony purification. Among these, many were not complemented by various gal mutants. The remainder (25 mutants) were surveyed for overlapping DNA repair defects by determining sensitivity to ultraviolet (UV) irradiation and to methyl methane sulfonate (MMS). This screening method identified five alleles of known rad mutations and one new mutation. This new mutation hrr25-1 (HO and/or radiation repair), presented severe defects and was studied further.

A recessive DNA repair defect is conferred by hrr25-1 that includes sensitivity to MMS. Hrr25-1 strains also show sensitivity at 5-20 Krad X-irradiation similar to that observed with mutations in the radiation repair genes RAD50 and RAD52 (Cole, et al, *Mol.Cell.Biol.*, 9:3101, 1989). The hrr25-1 strains are no more sensitive to UV irradiation than wild type and are not temperature sensitive for growth at 37° C. Unlike hypo- and hyper-rec rad mutants which have several of the hrr25-1 phenotypes, hrr25-1 strains undergo normal mitotic recombination (Cole, et al, *Mol.Cell.Biol.*, 9:3101, 1989). Spontaneous gene conversion and crossing-over were the same for homozygous hrr25-1 and wild type strains. However, HRR25 is required for the correct completion of meiosis. The hrr25-1 homozygotes showed less than 1% spores (tetranucleate cells) under conditions that produced 75-80% spores in an isogenic wild type strain. The hrr25-1 mutation could be complemented by a number of radiation sensitive mutations (rad6, 50, 52, 54, and 57) that present some of the hrr25 phenotypes, suggesting that hrr25-1 is a newly uncovered rad-like mutation and not one of these previously described genes. These results also indicate that HRR25 plays a role in DNA repair and meiosis, but is not specifically required for the repair of spontaneous mitotic lesions by recombination.

EXAMPLE 2

Isolation of HRR25

The HRR25 gene was obtained by complementing for MMS sensitivity using a yeast genomic library constructed in the plasmid YCp50 (Rose, et al., *Gene*, 60:237, 1987). An hrr25-1 strain, MHML 3-36d (ura3 hrr25), was transformed by standard methods (Nickoloff, et al, *J.Mol.Biol.*, 207:527, 1989) to uracil prototrophy, transformants were amplified on media without uracil and replicated to media containing 0.01% MMS. Among 1200 transformants, a single MMS resistant isolate was identified. Complementation for MMS sensitivity was found to segregate with the plasmid as determined by methods known in the art.

A 12 kb genomic fragment was identified and complementing activity was localized to a 3.1 kb BamHI-SalI fragment by transposon mutagenesis and subcloning. This region complemented DNA repair defects as well as meiotic deficiencies. Gene targeting experiments linked this cloned region to hrr25-1. Transposon insertion mutations within the BamHI-SalI fragment replaced into the cognate HRR25 genomic locus did not complement hrr25-1 for MMS sensitivity, whereas adjacent chromosomal insertions outside the complementing region segregated in repulsion when crossed against hrr25-1.

Mini-Tn10LUK transposons (Huisman, et al., *Genetics*, 116:191, 1987) were used to delineate the approximate location of HRR25 on the 12 kb BamHI-SalI fragment. Insertions located to the left hand 9 kb (of the 12 kb genomic fragment) did not inactivate complementation of hrr25-1 MMS resistance compared with the un-mutagenized plasmid. Two insertions, located near an EcoRV site in the right hand 2 kb inactivated complementation. HRR25 complementation activity was localized to a 3.4 kb SalI fragment. Approximately 300 bp of this fragment (right hand side of the 12 kb) were part of the pBR322 tetracycline resistance gene (between the BamHI site of pBR322-based YCp50). The HRR25 open reading frame spans an internal region across an EcoRV site and two BglII sites within the right terminal 3 kb.

The DNA sequence of the 3.1 kb fragment revealed a centrally located open reading frame of 1482 nucleotide. A transposon insertion mutation in this open reading frame inactivated HRR25 complementation whereas insertions elsewhere in the 12 kb clone did not affect HRR25 complementation. Transposon-mediated disruption of HRR25 also revealed several phenotypes not seen with hrr25-1. As expected, a Tn10-based LUK transposon insertion (Huisman, et al, *Genetics*, 116:191, 1987) into the middle of plasmid-borne HRR25 coding region inactivated complementation for MMS sensitivity. Transplacement of this insertion into the genomic HRR25 gene revealed a severe growth defect in addition to MMS sensitivity and meiotic inviability. This severe growth defect was not observed with hrr25-1 strains. Wild type HRR25 strains doubled in rich media at 30° C. every 80-90 minutes whereas isogenic hrr25::LUK strains and hrr25Δ doubled every 9-12 hours. hrr25-1 had a doubling time of 2-4 hours.

To determine whether the mutant phenotypes revealed by the hrr::LUK disruption allele represent a null phenotype, the entire HRR25 coding sequence was deleted. Briefly, deletion of the HRR25 coding sequence employed a hisG::URA3::hisG cassette (Alani, et al, *Genetics*, 16:541, 1988). The 3.1 kb HRR25 SalI fragment was cloned into pBluescript (Stratagene, La Jolla, Calif.). This plasmid was digested with BglII and the two BglII fragments that span the entire HRR25 gene and its flanking sequences were deleted. Into this deletion was introduced the 3.8 kb BamHI-BglII hisG::URA3::hisG fragment from pNKY51 to create the hrr25Δ allele. SalI digestion yielded a linearized fragment that deleted the entire HRR25 locus. Yeast carrying the deletion-disruption allele (hrr25Δ) showed phenotypes identical to those with the hrr25::LUK allele for all properties examined, including MMS sensitivity, slow growth, and the sporulation defect, indicating that wild-type HRR25 protein is associated with these processes and that the hrr25::LUK allele does not indirectly interfere with DNA repair, growth or sporulation. In direct parallel comparisons, the hrr25::LUK and hrr25Δ alleles behaved identically.

Yeast strain MFH14 (MATa/MATα ura3/ura3) was transformed with BglII-linearized YCp50-HRR25::LUK to uracil prototrophy, heterozygous disruption of HRR25 was verified by Southern blot analysis, the diploid was sporulated by starvation for nitrogen and fermentable carbon sources, tetrads dissected and cells allowed to germinate at 30° C. for 7 days. After a normal germination period of 2 days, the severe growth defect of hrr25::LUK suggested that the deletion of HRR25 was lethal. However, microscopic examination of segregants revealed that hrr25: :LUK germinating cells grew slowly and in every case examined (20/20 tetrads), slow growth, MMS sensitivity, and uracil prototrophy co-segregated. A color variation was seen with diploid MFH14 segregants, due to mutations in adenine biosynthesis. MFH14 is ade5/ADE5 ade2/ade2. An ade5/ade2 strain was white, while an ADE5/ade2 strain was red.

EXAMPLE 3

Sequence and Structure of the Hrr25 Gene

DNA sequencing of both strands of the HRR25 gene was done by unidirectional deletions employing Sequenase (USB, Cleveland, Ohio) and Exo-Meth (Stratagene, La Jolla, Calif.) procedures as described by the manufacturers. DNA and deduced amino acid sequences are set out respectively in SEQ. I.D. NOs. 1 and 2. FIG. 1A, shows the alignment of the amino acid sequences for HRR25, CDC28, KSS1, and RAF1. FIG. 1B shows a schematic representation of the structure of HRR25. The protein kinase homology is represented by a shaded region while the P/Q rich region is indicated by cross-hatchings. The mutant, hrr25, can be distinguished from HRR25 by one amino acid substitution. At position 1 51, an aspartic acid is substituted for glycine.

The predicted translation product of HRR25 revealed an unexpected feature for a rad-like DNA repair function. HRR25 contains the hallmark signatures of sequence homology with the catalytic domain of serine/threonine protein kinase superfamily members (Hanks, et al, Science, 241:42, 1988). For comparison, the HRR25 translation product was aligned with the catalytic domains for two subgroups of yeast protein kinases, the CDC28/cdc2 group and the KSS1/FUS3 group. Located between amino acids 15 and 30 is a region that contains the conserved GXGXXG region. Just C-terminal to this region is a conserved lysine and glutamic acid present in most known kinases. These regions are thought to function in the nucleotide binding and phosphotransfer steps of the kinase reaction (Hanks, et al, Science, 241:42, 1988). Between amino acid residues 120 to 150 are regions containing the HRD and DFG motifs, also found in most protein kinase family members. In addition, sequence examination of all known serine/threonine kinases indicates that HRR25 shares some additional similarities with the Raf/PKS/mos subgroup (Hanks, et al., Science, 241:42, 1988). The strongest homologies can be found in areas around the GXGXXG, DFG, and DXXSXG conserved regions in protein kinase catalytic domains.

The functional relevance of the observed sequence similarity between HRR25 and protein kinases was studied by altering specific residues within the HRR25 kinase domain and examining the phenotypic consequences of these changes. A lysine at position 38 (Lys[38]) was mutated to an arginine residue by site directed mutagenesis, by methods known in the art. The mutagenic oligonucleotide SEQ. I.D. NO. 22 was:

5'-CCTGATCGATTCCAGCCTGATCGCTACTTCTTC ACCACT-3'.

Lys[38] in HRR25 corresponds to the lysine found in all known protein kinases, and this subdomain is involved in ATP binding. Mutations at the conserved lysine in protein kinases such as v-src, v-mos, and DBF2 inactivate these proteins. The mutant hrr25-Lys[38] allele was incapable of complementing hrr25-1, hrr25::LUK, and hrr25Δ alleles for all properties examined, an indication that the HRR25 kinase domain is required for in vivo function of HRR25.

The predicted HRR25 translation product (SEQ. I.D. NO. 2) has a number of notable features outside the region of homology to protein kinase catalytic domains. For example, the last 100 amino acids is proline and glutamine rich, containing 50 of these residues. Other proteins with regions rich in these two amino acids include the transcription factors Sp 1, jun, and HAP2, steroid hormone receptors, the S. pombe ran 1 kinase, and mak-male germ cell-associated kinase (Courey, et al., Cell, 55:887, 1988; Bohmann, et al, Science, 238:1386, 1987; Roussou, et al, Mol.Cell. Biol., 8:2132, 1988; Arriza, et al, Science, 237:268, 1987; Matsushime, et al, Mol.Cell. Biol., 10:2261, 1990). In the case of Sp 1 and jun, the proline-glutamine regions are involved in transactivation, whereas the P/Q region in the human mineralocorticoid receptor is thought to serve as an intramolecular bridge. This proline-glutamine region in HRR25 might function as a structural feature for substrate interaction, or for subcellular localization. Also, the glutamine richness of this region is similar to the opa or M-repeat seen in the Drosophila and Xenopus Notch/Xotch proteins (Wharton, et al., Cell, 40:55, 1985; Coffman, et al, Science, 249:1438, 1990). The function of the opa repeat is not certain, but it is found in several Drosophila genes. Lastly, the sequence TKKQKY at the C-terminal end of the region homologous to protein kinases is similar to the nuclear localizing signal of SV40 large T antigen and yeast histone H2B (Silver, et al., J.Cell.Biol., 109:983, 1989; Moreland, et al., Mol.Cell.Biol., 7:4048, 1987).

EXAMPLE 4

Microscopic Analysis of Germinating and Proliferating hrr25 Cells

Photomicrographs of HRR25 and hrr25::LUK colonies were taken after germination on rich medium. An MFH14 hrr25::LUK heterozygous transformant was dissected onto a thin film of YPD rich medium on a sterilized microscope slide and segregants were allowed to germinate under a coverslip by incubating the slide in a moist 30° C. chamber. Photographs of colonies were taken after 2 days of growth. Phase contrast and DAPI staining of proliferating HRR25Δ and hrr25::LUK cells were compared. Cells were inoculated into YPD rich medium and grown at 30° C. to a mid-log density of 1–3×10[7] cells/ml, briefly sonicated to disrupt clumps, fixed with formaldehyde, and stained with DAPI (Williamson, et al, *Meth.Cell.Biol.*, 12:335, 1975). Many cells with hrr25::LUK lacked DAPI stainable nuclei.

Microscopic examination of germinating and actively growing mid-log phase hrr25::LUK cells revealed aberrant cellular morphologies. Transposon disruption of HRR25 resulted in large cells, and 25–40% of cells were filamentous or extended. DAPI nuclear staining (Williamson, et al, *Meth. Cell. Biol.*, 12:335, 1975) of mid-log populations showed that orderly cell cycle progression in hrr25 mutants was lost. There were a large number of cells lacking DAPI-stainable nuclei which, by single cell manipulations proved to be inviable. Consistent with this nuclear segregation defect, the plating efficiency of hrr25::LUK haploids was also reduced to 75–80% of wild type. However, this reduction in plating efficiency is insufficient to account for the severe growth rate reduction. Plating efficiency was measured from mid-log phase cells by comparing the efficiency of colony formation on rich medium relative to the total number of cells determined by hemocytometer count. Cell populations were analyzed for DNA content distribution by flow cytometric analysis following staining with propidium iodide as described (Hutter, et al *J. Gen. Microbiol.*, 113:369, 1979). Cell sorting analysis showed that a large number of the cells in a haploid hrr25::LUK population were delayed in the cell cycle and exhibited G2 DNA content, but the population was not arrested uniformly in the cell cycle.

EXAMPLE 5

Sequence Comparison of Hrr25 with CDC28, KSS1, and RAF1

The predicted translation product of HRR25 (SEQ. I.D. NO. 2) was compared with the catalytic domains of several members of the serine/threonine protein kinase superfamily. Initial sequence comparisons employed the UWGCG programs (Devereux, et al, *Nuc.Acids. Res.*, 12:387, 1984), whereas subgroup comparisons used the methods of Hanks, et al, supra. HRR25 contains all eleven subdomains described by Hanks, et al, supra. Structurally similar groupings were compared in the sequence comparisons. These included nonpolar chain R groups, aromatic or ring-containing R groups, small R groups with near neutral polarity, acidic R groups, uncharged polar R groups, and basic polar R groups.

CDC28 and KSS1 represent members of two subgroups of serine/threonine protein kinases in yeast. CDC28 is involved in cell cycle regulation while KSS1 acts in the regulation of the yeast mating pathway. HRR25 shows 21% identity and 41% similarity to CDC28 and 19% identity and 43% similarity to KSS1 (FIG. 1A). HRR25 shows highest similarity to members of the Raf1/PKS/Mos family of protein kinases. Through the catalytic domain, HRR25 shows 30% identity and 49% similarity to Raf1.

EXAMPLE 6

Identification, Isolation, and Analysis of *Sc. pombe* Hhp1+and Hhp2+Genes

A. Isolation of the Hhp1+and Hhp2+Genes

The clones were isolated by a two-pronged approach: i) DNA-based screening methods; and ii) direct complementation in *S. cerevisiae* hrr25 mutant strains. Two genes were identified (Hhp1+ and Hhp2+-so named for HRR25 Homologue from *Schizosaccharomyces pombe*). Expression of Hhp1+ in *S. cerevisiae* hrr25 mutants fully rescued all mutant defects. Expression of Hhp2+ in *S. cerevisiae* also rescued, to varying degrees, the defects associated with hrr25 mutations.

DNA-based amplification of HRR25-like DNAs from *Sc. pombe* genomic and cDNA sequences prepared according to Fikes, et al. (*Nature*, 346:291–293, 1990) was conducted using polymerase chain reaction with the following partially degenerate oligonucleotide primers:

(1) Primer No. 4583 (SEQ. ID. NO. 13) representing top strand DNA encoding residues 16 through 23 of HRR25; [1nmol/5μl], $T_m=52°$ C.;

(2) Primer No. 4582 (SEQ. ID. NO. 14) representing top strand DNA encoding residues 126 through 133 of HRR25; [1.5nmol/5μl], $T_m=54°$ C.;

(3) Primer No. 4589 (SEQ. ID. NO. 15) representing bottom strand DNA encoding residues 126 through 133 of HRR25; [0.5nmol/5/μl], $T_m=54°$ C.;

(4) Primer No. 4590 (SEQ. ID. NO. 16) representing bottom strand DNA encoding residues 194 through 199 of HRR25; [2nmol/5μl], $T_m=38°$ C.

Two series of amplifications were conducted using Perkin Elmer Automated apparatus; a first series using HRR25-based primer Nos. 4583 and 4589 and a second series employing all four of the primers. In the first series, 30 cycles of denaturation (94° C., 1 min), annealing (48° C., 1 min), and extension (66° C., 3 min) were performed and in a final cycle, the extension time was extended to 5 min. Reaction products were sized on an agarose gel revealing a prominent band of the expected size of about 306 bp. In the second series of amplifications, 30 cycles were carried out as above except that annealing and extension were carried out at 35° C. and 60° C., respectively. Three major products of the expected sizes (513 bp, 180 bp, and 306 bp) were developed in both genomic and cDNA libraries and were purified by preparative agarose gel electrophoresis.

Products were cloned into M13mp 19 and sequenced by the dideoxy method (Maniatis, et al., *Molecular Cloning: A Laboratory Manual*, 1982). Two classes of sequences were identified. A representative clone from each class was radio-labelled with $^{32}P$ by random primed cut labeling to a specific activity of $10^6$ cpm/μg (Maniatis, et al., supra) and used as a hybridization probe to isolate full length cDNA clones and to prove yeast genomic DNA in Southern blots and total RNA on Northern blots. Hybridization was carried out for 16 hours in a buffer containing 6×SSPE, 0.1% SDS, 5% dextran sulfate. Two genes were identified and designated Hhp1+and Hhp2+ for HRR25 Homologues from *Sc. pombe*.

For Hhp 1+, 7 clones were identified (6 partial and 1 full length clone). For Hhp2+, 2 full length clones were identified. Both Southern and Northern analysis confirmed that these clones were from separate genes. These genes were sequenced using standard dideoxy method (Maniatis, et al, supra). The nucleotide and deduced amino acid sequences for Hhp1+ are set out in SEQ. ID. NOS. 3 and 4; the nucleotide and deduced amino acid sequences for Hhp2 +are set out in SEQ. ID. NOS. 5 and 6.

B. Functional analysis of Hhp1+ and Hhp2+ in *S. cerevisiae* hrr25 mutants.

*Sc. pombe* Hhp1+ and Hhp2+ cDNAs were cloned in a location which placed them under the control of the *S. cerevisiae* alcohol dehydrogenase-1 (ADH1) promoter in a URA3-based vector pDB20 to allow for expression in *S. cerevisiae* (Fikes, et al., supra). These resulting clones were analyzed for their ability to alter/modify the suppress phenotypes associated with the hrr25-1 mutation and the hrr25Δ mutation following transformation into appropriate yeast strains by standard methods (Ito, et al., *J. Bacteriol.* 153:163, 1983). Transformants were analyzed for their ability to overcome defects associated with the hrr25 mutations (Hoekstra, et al., *Science*, 253:1031, 1991). Hhp1+ expression fully complemented hrr25-associated defects and was indistinguishable from wild type HRR25 in all analyses. Complementation was analyzed for the effect on DNA repair, cell cycle progression, cellular morphology, and sporulation. Hhp2+ complemented to a lesser degree than Hhp1+ (its complementation level was 50%–75% that of bona fide HRR25). The alteration of hrr25-associated phenotypes was dependent upon the transformed yeast strains containing both a complementing *Sc. pombe* Hhp plasmid and having hrr25 mutations.

The degree of amino acid homology between HRR25 protein and Hhp1+ protein is 73% through the kinase domain. The degree of similarity, which considers the presence of similar as well as identical amino acids, is greater than 85%. The amino acid identity of HRR25 protein and Hhp2+ protein is 63% with a percent similarity score of 80%. The intraspecies comparison of Hhp1+ protein to Hhp2+ protein is 72% identity. This structural and complementation analysis clearly indicates that these *Sc. pombe* clones are functional homologues of the *S. cerevisiae* HRR25. Such a high degree of relatedness is not seen with any other group of protein kinases. As a measure of comparison here, bona fide functional homologues (i.e., cdc2 protein kinases from *S. cerevisiae*, Sc. pombe, and humans) show 40%–45% identity. Any two randomly compared protein kinases, regardless of whether the comparison is inter-or intra-species show a degree of identity of about 20%–25%.

C. Disruption and mutation of Hhp 1+ and Hhp2+ in *Sc. pombe*

Mutations that inactivate or reduce the protein kinase activity of HRR25 in *S. cerevisiae* result in a wide variety of phenotypes including: sensitivity to various forms of DNA damage, severe cell cycle delay, sensitivity to drugs that affect cell cycle progression (e.g., caffeine), sensitivity to agents that affect microtubule integrity (e.g., benomyl), and sensitivity to agents that affect the integrity of replicating DNA (e.g., hydroxyurea).

Similarity, in *Sc. pombe*, inactivation of the Hhp1+ and the Hhp2+ genes to reduce or abolish the encoded protein kinase activity resulted in cellular phenotypes that mimicked hrr25 mutations. For example, deletion of the Hhp1+ gene resulted in a cell cycle delay and aberrant cellular morphology, in sensitivity to DNA damaging agents like MMS, and in sensitivity to benomyl and hydroxyurea. Deletion of the Hhp2+ gene resulted in caffeine sensitivity, benomyl sensitivity, and hydroxyurea sensitivity, amongst other defects.

The Hhp 1+ gene was disrupted as follows: cDNA was subcloned into the *Sc. pombe* vector pHSS19 (Hoekstra et al., *Meth. Enzymol*, 194:329, 1991), which was digested with NheI-EcoRI. The *Sc. pombe* URA4 gene was inserted resulting in deletion of the Hhp 1+ kinase domain. *Sc. pombe* was transformed by standard methods (Moreno, et al, *Meth. Enzymol*, 194:795, 1991) with the linearized DNA from the resulting plasmid construction. Stable transformants were identified and haploid hhp 1Δ strains were verified by standard methods (Moreno, et al., Maniatis, et al).

The Hhp2+ gene was disrupted as follows: the Hhp2+ cDNA was cloned into the *Sc. pombe* based vector, plasmid pHSS19, and was disrupted by transposon shuttle mutagenesis using the mini-Tn3 transposon mTn3Leu2 (Hoekstra, et al., Meth. Enzymol supra.). *Sc. pombe* was transformed by standard methods with the linearized DNA from the resulting plasmid construction. Stable transformants were identified and haploid hhp2Δ strains were verified by standard methods (see above).

Standard physiological methods as described for *S. cerevisiae* HRR25 (Hoekstra, et al., *Science* 253:1031, 1991) were employed to characterize hhp mutant strains. Phenotypic analysis revealed that both hhp1 and hhp2 mutants showed defects previously seen in hrr25 mutants, including sensitivity to various DNA damaging treatments that include MMS treatment and X-ray treatment.

The foregoing substantiates that Hhp1+ and Hhp2+ are isoforms of *S. cerevisiae* HRR25 protein kinase. These three protein kinases show high levels of sequence identity. In addition, mutations that inactivate these kinases result in very similar defects in widely divergent organisms.

D. Complementation of *Sc. pombe* mutant strains with the *S. cerevisiae* HRR25 gene.

To show that *Sc. pombe* hhp mutants prepared as described above, were identical to *S. cerevisiae* hrr25 mutants and to show that HRR25-like protein kinases with greater than 35% amino acid identity are functional homologues, the *S. cerevisiae* HRR25 gene was introduced into a *Sc. pombe* expression vector and transformed into *Sc. pombe* hhp mutants. The DNA sequence at the HRR25 initiating methionine was changed into an NdeI site, (a silent coding alteration that maintains the reading frame but allows the HRR25 gene to be introduced into appropriate *Sc. pombe* plasmids). This was done by a site-directed DNA change was made in the *S. cerevisiae* HRR25 gene by standard methods using a commercially available system (Bio-Rad, Cambridge, Mass.). The altered HRR25 gene was ligated into the *Sc. pombe* expression plasmid, pREP 1 (Maundrell, K. J., *Biol. Chem.* 265:10857, 1990), at an NdeI site and the resulting construction was transformed by standard methods into *Sc. pombe* hhp mutants. Expression of HRR25 in *Sc. pombe* mutant strains resulted in complementation of the mutant defects as evaluated by physiological methods described by Hoekstra, et al. (Science, supra).

EXAMPLE 7

Isolation and Characterization of Yeast HRR25-Like Genes

Isolation of additional HRR25-like genes from *S. cerevisiae* was accomplished by performing DNA-based amplification of genomic DNA from an *S. cerevisiae* strain lacking HRR25 coding sequences [Strain 7D of DeMaggio, et al (*Proc. Natl. Acad. Sci., USA*, 89:7008–7012, 1992, incorporated herein by reference) thereby eliminating the chance of obtaining HRR25 sequences from the amplification. The primers and amplification conditions were as in Example 6.

The resulting amplification products were cloned in M13mp19 and sequenced by dideoxy chain termination methods. Three unique classes of amplified products were identified. Two of these products respectively corresponded to the YCK1/CKI2 and YCK2/CKI1 genes of Robinson, et al. (*Proc. Natl. Acad. Sci. USA*, 8–9:28–32, 1992) and Wang, et al (*Molecular Biology of the Cell*, 3:275–286, 1992). The third gene product was designated "NUFI" (for Number Eour). The amplified products corresponding to NUF1 were radiolabelled as described in Example 6 and used to screen a yeast YCp50-based genomic library (ATCC, Rockville, Md.). Eight clones were identified and one of these clones included approximately 4 Kb HindIII fragment containing the NUF1 hybridizing gene. Southern analysis revealed that NUF1 is a separate gene from HRR25, YCK1/CK12, and YCK2/CKI1. The HindIII fragment was sequenced and revealed a protein kinase with about 65% identity to HRR25 through its protein kinase domain. The DNA and deduced amino acid sequences for NUF 1 are set out in SEQ. ID. NOS. 23 and 24.

To further characterize the NUF 1 gene, the HindIII fragment was subcloned into the yeast plasmid YEplac112 (Geitz, et al.). The resulting construct was transformed into the hrr25Δ deletion strain 7d and NUF 1 was found to complement for hrr25Δ mitotic defects (e.g., NUF1 complemented for slow growth defect, aberrant morphology defect, DNA damaging agent sensitivities). Furthermore, a null mutant allele of NUF 1 was constructed by transposon shuttle mutagenesis and strains lacking the NUF 1 gene product were found to have hrr25Δ mutant-like defects. In particular, like hrr25Δ mutants, NUF1 mutants showed slower mitotic growth rates and increased sensitivity to DNA damaging agents like MMS, UV, and X-irradiation.

EXAMPLE 8

Identification and Isolation of Human HRR25-Like Genes

Oligonucleotides derived from amino acid sequences described above in Example 6A were used to amplify cDNAs from the following sources: *Arabidopsis thaliana*, *Drosophila melanogaster*, Xenopus, chicken, mouse, rat, and human HeLa cells. These cDNAs were obtained from reverse transcribed mRNA (Maniatis, et al., supra) or from commercially-available cDNA libraries (Stratagene, La Jolla, Calif., and Clonetech). Amplification products of similar migration size to those obtained from *S. cerevisiae* HRR25 and *Sc. pombe*, Hhp1+ and Hhp2+ genes were observed in 1.0% Agarose gels (Maniatis, et al, supra). This result indicated that HRR25-like genes exist in all species examined.

Isolation of full length DNAs encoding human HRR25-like protein kinases was accomplished by PCR amplification of human genomic DNA using unique sequence oligonucleotide primers based on portions of a bovine brain casein kinase I cDNA which had been reported in Rowles, et al. (*Proc. Natl. Acad. Sci. USA*, 88:9548-9552, 1991) to encode a mammalian protein that was 60% homologous to HRR25 over its catalytic domain.

A variety of primers were prepared and used in pairwise fashion including:

(1) Primer JH21 (SEQ. ID. NO. 17) representing bovine top strand DNA bases 47-67;

(2) Primer JH22 (SEQ. ID. NO. 18) representing bovine top strand DNA bases 223-240;

(3) Primer JH29 (SEQ. ID. NO. 19) representing bovine top strand DNA bases 604-623;

(4) Primer JH30 (SEQ. ID. NO. 20) representing bovine top strand DNA bases 623-604; and (5) Primer JH31 (SEQ. ID. NO. 21) representing bovine top strand DNA bases 835-817.

DNA amplification with combination of oligonucleotides JH21/JH30, JH22/JH30, and JH29/JH31 were carried out for 30 cycles with denaturation performed at 94° C. for 4 min for the first cycle and for 1 min for the remaining cycle annealing at 50° C. for 2 min and extension at 72° C. for 4 min. Products of the expected size from the three amplifications were purified on preparative acrylamide gels and labeled with $^{32}$P using random nick translation (to a specific activity between $7 \times 10^6$ cpm/μg and $1.4 \times 10^7$ cpm/μg. The labelled probes were employed as a group to screen a commercial human fetal brain cDNA library (Stratagene). Hybridization was carried out for 16 hours at 65 °C. in a hybridization buffer containing 3×SSC, 0.1% Sarkosyl, 10×Denhart's solution and 20 mM sodium phosphate (pH 6.8). Three washes at 65° C. in 2×SSC, 0.1% SDS were performed. Approximately $1.5 \times 10^6$ plaques were screened on 30 plates using duplicate filters. Six strong positive clones were isolated, purified and converted to plasmid form according to procedures recommended by the supplier of the library. Restriction digestion revealed the following insert sizes for the six clones: clone 35A1, 1kb; clone 35B1, 1.4 kb; clone 41A1, 3.7 kb; clone 42A1, >4 kb; clone 47A1, 3.35 kb; and clone 51A1, 2.75 kb. All six inserts contained sequences which could be aligned with both the DNAs and deduced protein sequence of the bovine CKIα gene. The abbreviated, partial cDNA clones 35A1 and 35B1 were not further analyzed. Clones 41A1 and 42A1 were identical except for size. Clones 42A1, 51A1, and 47A1 were redesignated as CKIα1Hu, CKIα2Hu, and CKIα3Hu. The DNA and deduced amino acid sequences of the inserts are set out in SEQ. ID. NOS. 7 and 8; 9 and 10; and 11 and 12, respectively. The deduced amino acid sequence for CKIα1Hu was identical to the reported bovine CKIα sequence. Table 1, below sets out differences in nucleotides between the bovine and human DNAs, numbered from the first base in the initiation codon, ATG.

TABLE 1

| COMPARISON OF HUMAN AND BOVINE CKIα DNA | | | | | |
|---|---|---|---|---|---|
| Position | Bovine | Human | Position | Bovine | Human |
| +9 | C | T | +591 | A | G |
| +27 | A | T | +594 | A | G |
| +93 | T | C | +669 | A | G |
| +126 | G | A | +687 | A | G |
| +147 | C | T | +690 | G | A |
| +186 | A | G | +705 | A | G |
| +255 | T | C | +729 | A | G |
| +258 | C | T | +731 | C | T |
| +261 | G | A | +753 | A | G |
| +267 | T | C | +771 | C | G |
| +279 | T | G | +798 | G | A |
| +285 | C | T | +816 | G | A |
| +291 | T | C | +828 | C | T |
| +372 | C | T | +867 | T | C |
| +540 | T | C | +870 | C | T |
| +555 | T | C | +936 | A | C |
| +558 | G | A | | | |

The CKIα3Hu DNA also includes an insertion of 84 bases at position +454 in the coding sequence providing an intermediate extension of the CKIα2Hu expression product by 28 amino acids. This DNA insert is not present in the bovine gene, but it encodes an amino acid sequence insert which Rowles, et al designated as CKI-alpha-L. The CKIα2Hu and CKIα3Hu DNAs insertion at position +971 of the CKIα1Hu DNA. This insertion is not found in any of the bovine sequences and encodes an extension of the 13 amino acids adjacent the carboxy terminal. The last two codons of the CKIα3Hu sequences differ from any of the bovine sequences or the sequences of CKIα1Hu and CKIα2Hu, causing the CKIα3Hu expression product to terminate with a lysine, rather than a phenylalanine as found in all the other bovine and human casein kinase I sequences. The 3' flanking sequence of CKIα3Hu DNA differs significantly from that of CKIα1Hu and CKIα2Hu.

FIG. 2A and 2B provide an alignment of the catalytic domain amino acid sequences of HRR25-like proteins whose DNAs were isolated in the above illustrative examples, including HRR25, Hhp 1+, Hhp2+, CKIα1Hu, CKIα2Hu, and CKIα3Hu as well as YCK1/CKI2, and YCK2/CKI1. Note that with the exception of the CKIα3Hu intermediate insert and the carboxy terminal region inserts of CKIα2Hu and CKIα3Hu, the sequences of the three human products are identical. "Common" residues are indicated in the Figure where at least 3 of the seven residues are identical at the corresponding position (the human sequences being taken as a single sequence).

Like Hhp1+ and Hhp2+, the three human HRR25-like protein kinases showed very high degrees of amino acid identity to the HRR25 gene product (68%), establishing that these human clones were enzymatic isoforms of the yeast HRR25 gene. The alignment of HRR25, Hhp1+, Hhp2+, and the human complementing-like kinase isoforms show that these enzymes share a number of primary structural features that indicate that these enzymes provide comparable activities in different species. This conclusion is reached based on several lines of evidence. First, all enzymes share the common primary sequence identifiers characteristic of protein kinases. Second, the enzymes share high degrees of amino acid identity in regions of the protein kinase domain that are not conserved in unrelated protein kinases. Finally, these enzymes share regions of identity in the kinase domain which regions differ in primary sequence from other protein kinases, but are identical among the members of this isoform grouping. For example, greater than 95% of all known protein kinases have a so-called A-P-E sequence (Alanine-Proline-Glutamate) approximately two-thirds of the way through the kinase domain. HRR25-like protein kinases lack the A-P-E sequence and have instead a S-I/V-N sequence (Serine-lsoleucine or ValineAsparagine). Based on this primary sequence comparison, between known protein kinases and the protein kinases of the invention from evolutionarily divergent organisms, these enzymes of the invention are isoforms of HRR25 protein kinase.

EXAMPLE 9

Comparison of HRR25 with a Casein Kinase

In all eukaryotes examined, two of the major protein kinases are casein kinase I and II (CKI and CKII, respectively). These enzymes have been found in all cell types and species examined. Both enzymes recognize Ser/Thr residues in an acidic environment in the substrate. These two protein kinases are found throughout the cell and their activities have been purified from or found to be associated with cytoplasmic fractions, membranes, nuclei, mitochondria, and cytoskeleton. CKII is predominantly a nuclear enzyme, but similar studies have yet to be described for CKI.

To determine whether HRR25 gene product might function as a casein kinase, the ability of HRR25-containing immunoprecipitates to phosphorylate casein was studied. HRR25-containing immunoprecipitates from yeast were incubated with casein and phosphorylated proteins were examined.

Yeast extracts were prepared by physical disruption. Equal volumes of a cells were suspended in lysis buffer and acid-washed 0.5 mm beads were mixed, 30 second bursts were interspersed with 1 min on ice, and the extent of disruption was followed microscopically. Lysis buffer contained 10 mM sodium phosphate (pH 7.2), 150 mM NaCl, 1% Nonidet P-40, 1% Trasylol, 1 mM DTT, 1 mM benzamidine, 1 mM phenylmethyl sulfonyl fluoride, 5 mM EDTA, pepstatin (1 ug/ml), Pepstatin A (2 ug/ml), leupeptin (1 ug/ml), 100 mM sodium vanadate, and 50 mM NaF. Extracts were clarified by a 100,000×g centrifugation for 30 min., made to 50% (vol/vol) with glycerol, frozen in liquid nitrogen, and stored at −70 degrees C. Little loss in protein kinase activity was seen in frozen extracts over several months.

Immune complex protein kinase assays were performed on the extracts according to the methods described in Lindberg, et al. (Mol. Cell. Biol. 10:6316, 1991). Frozen extracts were diluted to 25% glycerol with lysis buffer or fresh extracts were used directly. Extracts were precleared with preimmune serum and protein A-Sepharose, and then treated with immune serum (obtained as described in Example 11, infra, from immunization of rabbits with E. coli-derived type-HRR25 fusion products). HRR25 kinase-containing immune complexes were precipitated with protein A-Sepharose. Immune complexes were washed four times with lysis buffer and twice with kinase buffer containing 15 mM Hepes (pH 7.4), 100 mM NaCl, and 10 mM MgCl$_2$.

Reaction mixtures of HRR25 immunoprecipitates and heat-treated casein (300 ng/20 ul reaction volume) were incubated at 30 degrees C for 5–10 min and contained 10 uCi of gamma-$^{32}$P-ATP per 20 ul reaction volume. Reactions were stopped by the addition of SDS and EDTA, boiled in SDS/PAGE sample buffer and resolved in 10% gels. Phosphoamino acid analysis was as described (Hunter et al., Proc. Natl. Acad. Sci. USA 77:1311, 1980).

Immunoprecipitates from HRR+ strains were able to phosphorylate casein. To verify that the appropriate amino acids were phosphorylated, the phosphoamino acid composition of the HRR25-phosphorylated casein was examined by phosphoamino acid analysis. Samples were resolved by two-dimensional electrophoresis at pH 1.9 and pH 3.5. Consistent with mammalian CKI specificity, serine and threonine residues were phosphorylated. HRR25 phosphorylated serine residues on casein 3-fold greater than threonine residues. Similarly, the autophosphorylation of HRR25 in immune complexes in vitro occurred on serine and threonine residues. Coupled with the high degree of sequence identity, these results suggest that HRR25 might be a CKI isoform.

To extend and confirm that HRR25 immunoprecipitates from yeast could phosphorylate casein, several experiments were performed. HRR25 immunoprecipitated from E. coli strains expressing HRR25 (See Example 11) also showed casein kinase activity, whereas E. coli extracts lacking HRR25 protein did not phosphorylate casein. HRR25-containing baculovirus constructs produced casein kinase activity in immunoprecipitates. Wild-type baculovirus-infected cells showed <0.5% casein kinase activity under comparable conditions. The protein kinase activity from S19 cells expressing HRR25 protein was sensitive to the same conditions that reduced or inactivated the HRR25 protein activity from yeast extracts. The observations that HRR25-dependent casein kinase activity was present in immunoprecipitates from E. coli cells expressing wild-type HRR25, in insect cells infected with HRR25-containing baculovirus, and in wild-type but not hrr25Δ mutants indicated that the HRR25 gene product could function as a casein kinase and that the casein kinase activity in HRR25 protein-containing immunoprecipitates was due to HRR25 gene product.

EXAMPLE 10

Analysis of Protein Kinase Activity of HRR25-Like Proteins

Because the predominant protein kinase activity in *E. coli* is histidine kinase, rather than serine/threonine or tyrosine kinase, those procaryotic cells provide a system for examination of HRR25-like protein kinase activities which is not compromised by presence of endogenous kinases. Both HRR25 and Hhp1+ DNAs were, therefore, expressed in the IPTG-inducible T7 gene 10-based commercial expression system (Invitrogen, San Diego, Calif.) using *E. coli* strain BL21 (DE3) which contains an IPTG-inducible T7 RNA polymerase and T7 lysozyme gene. See, DeMaggio, et al., *Proc. Natl. Acad. Sci. USA*, 89:7008–7012, (1991). In a first series of experiments, *E. coli* lysates were prepared by inducing mid-log phase cells with IPTG for 2 hours, pelleting the cells, and preparing extracts by a freeze-thaw method using buffers described in DeMaggio, et al, supra. Extracts were electrophoresed in polyacrylamide gels, transferred to nylon-based support membranes, and probed by Western analysis with antibodies directed against phosphotyrosine (UBI Lake Placid, N.Y.). These procedures revealed that HRR25 and Hhp1+ expressing cells contained novel tyrosine phosphorylated proteins not observed in control cells (transformed with the vector alone or with kinase inactive mutants). In a second experiment, the HRR25 and Hhp 1+ -containing *E. coli* strains were examined for tyrosine-phorphorylated protein by a sensitive and accurate radiolabelling and phosphoamino acid procedure. To do this experiment, cells were induced with IPTG and grown in the presence of $^{32}$P-orthophosphate. Radiolabelled extracts were prepared by the freeze-thaw method, electrophoresed in polyacrylamide gels, and the gels were examined by autoradiographic methods. Novel phosphoproteins were observed in the strains expressing HRR25 and Hhp1+, but not in the above controls. Phosphoproteins were examined by extracting and hydrolyzing the proteins from the gels using standard methods (Boyle, et al, *Meth. Enzymol*, 201:110, 1991). These experiments verified that HRR25 and Hhp 1+ could phosphorylate tyrosine, serine, and threonine residues on protein substrates.

EXAMPLE 11

Recombinant Expression of HRR25 Products and Generation of Antibodies Thereto Two different plasmid constructions were developed for expression of HRR25 DNA in *E. coli* to generate immunogens useful in preparation of anti-HRR25 antibodies.

The first plasmid construction involved plasmid pATH according to Koerner et al, *Meth. Enzymol*, 194:477–491 (1991). An approximately [606] base pair DNA fragment was isolated from the HRR25 open reading frame by Bgl II digestion and this fragment (which encodes amino acid residues 275–476) was ligated into pATH which had been digested with BamHI. The resulting plasmid encoded a fusion protein comprising the *E. coli* TrpE gene product at its amino terminus and a carboxy terminal fragment of HRR25 at its carboxyl terminus.

Inclusion bodies were isolated from *E. coli* DH5α (Bethesda Research Laboratories, Bethesda, Md.) host cells transformed the plasmid using lysis buffers as described in Koerner et al, supra, and were purified by polyacrylamide gel electrophoresis. The gel purified materials were then employed in the immunization of rabbits by subcutaneous injection as recommended by Harlow, et al, *Antibodies: A Laboratory Manual*, Cold Spring Harbor Laboratory, Cold Spring Harbor, N.Y. (1988), using gel purified products with complete Freund's adjuvant for primary injections and incomplete Freund's adjuvant for subsequent injections. Serum reactivity was followed by Western blotting against the gel purified antigen. Affinity purification of serum antibodies was effected using the *E. coli* -produced antigen immobilized on a nitrocellulose membrane support.

Subsequent to the filing of U.S. patent application Serial No. 07/728,783 on Jul. 3, 1991, there have been numerous reports in the scientific literature of the isolation of DNAs encoding HRR25-like proteins. For example, Rowles, et al, (*Proc. Natl. Acad. Sci. USA*, 88:9548–9592, 1991) reported the purification of a bovine thymus casein kinase I (CKI) enzyme. The sequencing of tryptic fragments reveled nearly 25% of the primary sequence of the enzyme. PCR cloning resulted in development of partial clones coding for the CKI enzyme isolate and a homologue enzyme referred to as CKI-δ. Screening of bovine brain libraries with the partial clones yielded full length cDNAs for the CKI isolate (designated CKIα) and two additional homologues (CKIβ and CKIγ). The deduced sequence for bovine CKIα was noted to be 60% homologous to HRR25 over its catalytic domain. As noted earlier, a comparison of the bovine CKIα sequence of Rowles, et al. to human CKIα1 sequence set out in SEQ. ID. NO. 7 and 8 reveals 100% homology in the catalytic domain.

As another example, Robinson, et al. (*Proc. Natl. Acad. Sci. USA*, 89:28–32, 1992) describes the isolation of two *Saccharomyces cerevisiae* genes, YCK1 and YCK2 which encode yeast casein kinase 1 homologues and also describes purification and partial sequencing of a rabbit casein kinase I from a rabbit reticulocyte lysate preparation. HRR25 was noted to be 50% homologous to YCK1 and YCK2 and 60% homologous to the partial rabbit CKI sequence. As a further example, Wang, et al. (*Molecular Biology of the Cell*, 3:275–286, 1992) describes the isolation of a 54 kDa CKI from *S. cerevisiae* and the use of amino acid sequence information therefrom for cloning two yeast cDNAs encoding homologous casein kinase I proteins, CKI1 and CKI2. Comparison of the catalytic domains of the protein encoded by the CKI1 gene produced few alignments revealing greater than 20–25% homology. The closest matches were with HRR25 (50–56%) and with the three bovine isozymes of Rowles, et al. (51–56%). The YCK1 sequence of Robinson, et al. corresponds to the CKI2 sequence of Wang, et al.; the YCK2 sequence corresponds to CKI1. Finally, Brockman, et al. (*Proc. Natl. Acad. Sci, USA*, 89:9454–9458, 1992) reported the immunopurification and sequencing of a human erythroid casein kinase I and noted that it was 62% homologous to HRR25.

While the foregoing illustrative examples are specifically directed to isolation of "full length" polynucleotides encoding the HRR25-like proteins HRR25, Hhp1+, Hhp2+, CKIα1Hu, CKIα2Hu, and CKIα3Hu, it will be readily understood that the present invention is not limited to those polynucleotides. Rather it embraces all polynucleotides which are comprehended within the class of genes encoding HRR25-like proteins characterized protein kinase activity and by homology of 35% or more with the HRR25 protein through the protein kinase catalytic domain. By way of example, employing information concerning the DNA sequence of HRR25, the procedures of Example 7 allowed the isolation partial cDNA clones of expected length from cDNA libraries derived from Arabidopsis thaliana, Drosophila melanogaster, Xenopus, chicken, mouse, rat, and human species. These partial cDNAs may, in turn, be employed in the manner of Examples 6 and 7 to isolate full length DNA clones encoding HRR25-like proteins from these species. Each of these may be employed in the large scale production of the corresponding proteins by recombinant methods or for the generation of other useful polynucleotides such as antisense RNAs. Recombinant expression products of such HRR25-like DNAs may be employed for generation of antibodies and in screens for compounds which modulate the protein kinase and/or recombination/ repair functions of these enzymes. Moreover, as suggested in the publication of Rowles, et al, Robinson, et al., and Wang, et al., multiple HRR25-like isozymes are expected to exist in a variety of eucaryotic species as both membrane bound and cytoplasmic proteins. It appears reasonable to expect that a number of genes and gene products exist in human species, all of which are functionally related as well as structurally related to each other and to HRR25.

SUMMARY OF SEQUENCES

Sequence I.D. No. 1 is the nucleic acid sequence and the deduced amino acid of a genomic fragment encoding a yeast-derived protein kinase, HRR25 of the present invention.

Sequence I.D. No. 2 is the deduced amino acid sequence of a yeast-derived protein kinase HRR25 of the present invention.

Sequence I.D. No. 3 is the nucleic acid sequence (and the deduced amino acid sequence) of a genomic fragment encoding Hhp1+ of the present invention.

Sequence I.D. No. 4 is the deduced amino acid sequence of Hhp1+ of the present invention.

Sequence I.D. No. 5 is the nucleic acid sequence (and the deduced amino acid sequence) of a genomic fragment encoding Hhp2+ of the present invention.

Sequence I.D. No. 6 is the deduced amino acid sequence of Hhp2+ of the present invention.

Sequence I.D. No. 7 is the nucleic acid sequence (and the deduced amino acid sequence) of a genomic fragment encoding CK1α1Hu of the present invention.

Sequence I.D. No. 8 is the deduced amino acid sequence of CK1α1Hu of the present invention.

Sequence I.D. No. 9 is the nucleic acid sequence (and the deduced amino acid sequence) of a genomic fragment encoding CK1α2Hu of the present invention.

Sequence I.D. No. 10 is the deduced amino acid sequence of CK1α2Hu of the present invention.

Sequence I.D. No. 11 is the nucleic acid sequence (and the deduced amino acid sequence) of a genomic fragment encoding CK1α3Hu of the present invention.

Sequence I.D. No. 12 is the deduced amino acid sequence of CK1α3Hu of the present invention.

Sequence I.D. No. 13 is the primer, 4583, representing top strand DNA encoding residues 16–23 of HRR25.

Sequence I.D. No. 14 is the primer, 4582, representing top strand DNA encoding residues 126–133 of HRR25.

Sequence I.D. No. 15 is the primer, 4589, representing bottom strand DNA encoding residues 126–133 of HRR25.

Sequence I.D. No. 16 is the primer, 4590, representing bottom strand DNA encoding residues 194–199 of HRR25.

Sequence 17 is the primer JH21, representing bovine top strand DNA bases 47–67.

Sequence 18 is the primer JH22, representing bovine top strand DNA bases 223–240.

Sequence 19 is the primer JH29, representing bovine top strand DNA bases 604–623.

Sequence 20 is the primer JH30, representing bovine bottom strand DNA bases 623–604.

Sequence 21 is the primer JH31, representing bovine bottom strand DNA bases 835–817.

Sequence 22 is the mutated HRR25 kinase domain primer found on p. 33, Example 3.

Sequence I.D. No. 23 is the nucleic acid sequence (and the deduced amino acid sequence) of a genomic fragment encoding NUF1 of the present invention.

Sequence I.D. No. 24 is the deduced amino acid sequence of NUF 1 of the present invention.

Sequence I.D. Nos. 25, 26 and 27 are the conserved motifs found on page 18.

The invention now being fully described, it will be apparent to one of ordinary skill in the art that various changes and modifications can be made without departing from the spirit or scope of the invention.

---

---

I claim:

1. An isolated and purified polynucleotide sequence encoding a polypeptide selected from the group consisting of the polypeptide disclosed in SEQ ID NOs: 4, 6, 8, 10, 12, and 24.

2. The polynucleotide of claim 1 wherein the encoded polypeptide possesses casein kinase activity.

3. The polynucleotide of claim 1 wherein the encoded polypeptide possesses protein-serine/threonine kinase activity.

4. The polynucleotide of claim 1 wherein the encoded polypeptide possesses protein-tyrosine kinase activity.

5. The polynucleotide of claim 1 wherein the encoded polypeptide possess protein-serine/threonine and protein-tyrosine kinase activity.

6. The polynucleotide of claim 1, wherein the polypeptide is characterized as:

a) promoting normal mitotic recombination; and b) promoting the repair a DNA strand break which occurs at the cleavage site:

↓
CAACAG
GTTGTC.
↑

7. The polynucleotide of claim 1, selected from the group consisting of RNA, mRNA, genomic DNA and cDNA.

8. The polynucleotide of claim 1, selected from the group consisting of the DNA sequences of SEQ ID NOs. 3, 5, 7, 9, 11 and 23.

9. An autonomously replicating extrachromosomal DNA vector comprising a DNA according to claim 7.

10. A procaryotic or eucaryotic host cell stably transformed or transfected with a DNA according to claim 7.

11. A method for the production of a polypeptide possessing protein kinase and/or recombination/repair promoting activity comprising growing a host cell according to claim 10 in a suitable nutrient medium and isolating the desired polypeptide from said host cell or from the medium of its growth.

* * * * *

UNITED STATES PATENT AND TRADEMARK OFFICE
CERTIFICATE OF CORRECTION

Page 1 of 3

PATENT NO. : 5,627,064
DATED : May 6, 1997
INVENTOR(S) : Merl F. Hoekstra

It is certified that error appears in the above-identified patent and that said Letters Patent is hereby corrected as shown below:

On the title page, item [56]:

Other Publications, Robinson, et al., "Yeast casein kinase I homologues: an essential gene pair," *Proc. Natl. Acad. Sci. (USA) 89*:28-32, 1992" is missing;

Other Publications, Rowles, et al., "Purification of casein kinase I and isolation of cDNAs encoding multiple casein kinase I-like enzymes," *Proc. Natl. Acad. Sci. (USA) 88*:9548-9552, 1991" is missing;

Other Publications, Wang, et al., "Two genes in *Saccharomyces cerevisiae* encode a membrane-bound form of casein kinase-I," *Mol. Biol. Cell. 3*:275, 1992" is missing;

Column 1, line 27 replace "catalytic: domains" with --catalytic domains--;

Column 1, line 43 replace "kinase land casein" with --kinase I and casein--;

Column 5, line 19 replace "5 these functional" with --These functional--;

Column 6, line 3 replace "1Cold Spring Harbor" with --Cold Spring Harbor--;

Column 8, line 1 a new paragraph should begin with "Analysis of eukaryotic DNA...";
Column 9, line 52 replace "2.56:495" with --256:495--;

Column 9, line 56 replace "which 15 affects" with --which affects--;

Column 14, line 67 replace "16:541" with --116:541--;

Column 15, line 26 replace "hrr25: :LUK" with --hrr25::LUK--;

Column 15, line 49 replace "At position 1 51" with --At position 151--;

Column 16, line 30 replace "Sp 1, jun" with --*Sp1, jun*--;

Column 16, line 31 replace "ran 1 Kinase" with --ran1 kinase--;

UNITED STATES PATENT AND TRADEMARK OFFICE
CERTIFICATE OF CORRECTION

PATENT NO. : 5,627,064
DATED : May 6, 1997
INVENTOR(S) : Merl F. Hoekstra

It is certified that error appears in the above-identified patent and that said Letters Patent is hereby corrected as shown below:

Column 16, line 36 replace "Sp 1 and" with --Sp1 and--;

Column 18, line 37 replace "M13mp 19" with --M13mp19--;

Column 19, line 28 replace "Sc. pombe" with --*Sc. pombe*--;

Column 19, line 33 replace "Hhp 1+" with --Hhp1+--;

Column 19, line 43 replace "similarity" with --similarly--;

Column 20, line 30 replace "was made in the" with --in the--;

Column 20, line 58 replace "8-9" with --89--;

Column 20, line 60 replace "NUFT" with --NUF1--;

Column 20, line 61 replace "Eour" with --Four--;

UNITED STATES PATENT AND TRADEMARK OFFICE
CERTIFICATE OF CORRECTION

PATENT NO. : 5,627,064
DATED : May 6, 1997
INVENTOR(S) : Merl F. Hoekstra

It is certified that error appears in the above-identified patent and that said Letters Patent is hereby corrected as shown below:

Column 21, line 28 replace "Xenopus" with --*Xenopus*--;

Column 23, line 60 replace "Equal volumes of a cells" with --Equal volumes of cells--;

Column 26, line 65 replace "isolation partial" with --isolation of partial--;

Column 26, lines 66 and 67 replace "Arabidopis thaliana, Drosophila melanogaster, Xenopus" with --*Arabidopis thaliana, Drosophila melanogaster, Xenopus*--;

Signed and Sealed this

Twelfth Day of December, 2000

Attest:

Q. TODD DICKINSON

*Attesting Officer*   *Director of Patents and Trademarks*

SEQUENCE LISTING ( 1 ) GENERAL INFORMATION:

( i i i ) NUMBER OF SEQUENCES: 27

( 2 ) INFORMATION FOR SEQ ID NO:1:

( i ) SEQUENCE CHARACTERISTICS:
        ( A ) LENGTH: 3098 base pairs
        ( B ) TYPE: nucleic acid
        ( C ) STRANDEDNESS: single
        ( D ) TOPOLOGY: linear ( i i ) MOLECULE TYPE: DNA (genomic)

( v i i ) IMMEDIATE SOURCE:
        ( B ) CLONE: Protein Kinase ( i x ) FEATURE:
        ( A ) NAME/KEY: CDS
        ( B ) LOCATION: 879..2360

( x i ) SEQUENCE DESCRIPTION: SEQ ID NO:1:

```
GTCGACTCGC CAATCACCAA GTTCTTATCC CACATCCGAC CAGTGTCTGA GTCATGGTTT      60
ACCACCACCA TACCATCGCT GGTCATTTGT AAATCCGTTT CTATTACATC AGCACCTGCT     120
GCATAAGCCT TCTCAAATGC TAGTAGCGTA TTTTCAGGAT ATCTTGCTTT AAAAGCTCTG     180
TGGCCCACAA TTTCAACCAT CCTCGTGTCC TTGTTGTTAT CTTACACTTC TTATTTATCA     240
ATAACACTAG TAACATCAAC AACACCAATT TTATATCTCC CTTAATTGTA TACTAAAAGA     300
TCTAAACCAA TTCGGTATTG TCCTCGATAC GGCATGCGTA TAAAGAGATA TAATTAAAAG     360
AGGTTATAGT CACGTGATGC AGATTACCCG CAACAGTACC ACAAAATGGA TACCATCTAA     420
TTGCTATAAA AGGCTCCTAT ATACGAATAA CTACCACTGG ATCGACGATT ATTTCGTGGC     480
AATCATATAC CACTGTGAAG AGTTACTGCA ACTCTCGCTT TGTTTCAACG CTTCTTCCCG     540
TCTGTGTATT TACTACTAAT AGGCAGCCCA CGTTGAATT CTTTTTTTC TGGAGAATTT       600
TTGGTGCAAC GAGGAAAAGG AGACGAAGAA AAAAGTTGA AACACGACCA CATATATGGA      660
ACGTGGTTGA ATACAAAGA GAAGAAAGGT TCGACACTCG AGGAAAGCAT TGGTGGTGA       720
AAACACATCT TAGTAGCATC TTTAAACCTC TGTTGGGTAC TTAGAAAAAT ATTTCCAGAC     780
TTCAAGGATA AAAAAAGTCG AAAAGTTACG ACATATTCGA CCAAAAAAAA AAACCAAAAA     840
GAAAAGATAT ATTTATAGAA AGGATACATT AAAAAGAG ATG GAC TTA AGA GTA        893
                                          Met Asp Leu Arg Val
                                           1                 5

GGA AGG AAA TTT CGT ATT GGC AGG AAG ATT GGG AGT GGT TCC TTT GGT       941
Gly Arg Lys Phe Arg Ile Gly Arg Lys Ile Gly Ser Gly Ser Phe Gly
            10                  15                  20

GAC ATT TAC CAC GGC ACG AAC TTA ATT AGT GGT GAA GAA GTA GCC ATC       989
Asp Ile Tyr His Gly Thr Asn Leu Ile Ser Gly Glu Glu Val Ala Ile
        25                  30                  35

AAG CTG GAA TCG ATC AGG TCC AGA CAT CCT CAA TTG GAC TAT GAG TCC      1037
Lys Leu Glu Ser Ile Arg Ser Arg His Pro Gln Leu Asp Tyr Glu Ser
    40                  45                  50

CGC GTC TAC AGA TAC TTA AGC GGT GGT GTG GGA ATC CCG TTC ATC AGA      1085
Arg Val Tyr Arg Tyr Leu Ser Gly Gly Val Gly Ile Pro Phe Ile Arg
55                  60                  65

TGG TTT GGC AGA GAG GGT GAA TAT AAT GCT ATG GTC ATC GAT CTT CTA      1133
Trp Phe Gly Arg Glu Gly Glu Tyr Asn Ala Met Val Ile Asp Leu Leu
70                  75                  80                  85

GGC CCA TCT TTG GAA GAT TTA TTC AAC TAC TGT CAC AGA AGG TTC TCC      1181
Gly Pro Ser Leu Glu Asp Leu Phe Asn Tyr Cys His Arg Arg Phe Ser
            90                  95                 100

TTT AAG ACG GTT ATC ATG CTG GCT TTG CAA ATG TTT TGC CGT ATT CAG      1229
Phe Lys Thr Val Ile Met Leu Ala Leu Gln Met Phe Cys Arg Ile Gln
        105                 110                 115

TAT ATA CAT GGA AGG TCG TTC ATT CAT AGA GAT ATC AAA CCA GAC AAC      1277
Tyr Ile His Gly Arg Ser Phe Ile His Arg Asp Ile Lys Pro Asp Asn
    120                 125                 130

TTT TTA ATG GGG GTA GGA CGC CGT GGT AGC ACC GTT CAT GTT ATT GAT      1325
Phe Leu Met Gly Val Gly Arg Arg Gly Ser Thr Val His Val Ile Asp
135                 140                 145

TTC GGT CTA TCA AAG AAA TAC CGA GAT TTC AAC ACA CAT CGT CAT ATT      1373
Phe Gly Leu Ser Lys Lys Tyr Arg Asp Phe Asn Thr His Arg His Ile
150                 155                 160                 165

CCT TAC AGG GAG AAC AAG TCC TTG ACA GGT ACA GCT CGT TAT GCA AGT      1421
Pro Tyr Arg Glu Asn Lys Ser Leu Thr Gly Thr Ala Arg Tyr Ala Ser
            170                 175                 180

GTC AAT ACG CAT CTT GGA ATA GAG CAA AGT AGA AGA GAT GAC TTA GAA      1469
```

```
Val Asn Thr His Leu Gly Ile Glu Gln Ser Arg Arg Asp Leu Glu
            185                 190                 195

TCA CTA GGT TAT GTC TTG ATC TAT TTT TGT AAG GGT TCT TTG CCA TGG    1517
Ser Leu Gly Tyr Val Leu Ile Tyr Phe Cys Lys Gly Ser Leu Pro Trp
        200                 205                 210

CAG GGT TTG AAA GCA ACC ACC AAG AAA CAA AAG TAT GAT CGT ATC ATG    1565
Gln Gly Leu Lys Ala Thr Thr Lys Lys Gln Lys Tyr Asp Arg Ile Met
        215                 220                 225

GAA AAG AAA TTA AAC GTT AGC GTG GAA ACT CTA TGT TCA GGT TTA CCA    1613
Glu Lys Lys Leu Asn Val Ser Val Glu Thr Leu Cys Ser Gly Leu Pro
230                 235                 240                 245

TTA GAG TTT CAA GAA TAT ATG GCT TAC TGT AAG AAT TTG AAA TTC GAT    1661
Leu Glu Phe Gln Glu Tyr Met Ala Tyr Cys Lys Asn Leu Lys Phe Asp
                250                 255                 260

GAG AAG CCA GAT TAT TTG TTC TTG GCA AGG CTG TTT AAA GAT CTG AGT    1709
Glu Lys Pro Asp Tyr Leu Phe Leu Ala Arg Leu Phe Lys Asp Leu Ser
            265                 270                 275

ATT AAA CTA GAG TAT CAC AAC GAC CAC TTG TTC GAT TGG ACA ATG TTG    1757
Ile Lys Leu Glu Tyr His Asn Asp His Leu Phe Asp Trp Thr Met Leu
        280                 285                 290

CGT TAC ACA AAG GCG ATG GTG GAG AAG CAA AGG GAC CTC CTC ATC GAA    1805
Arg Tyr Thr Lys Ala Met Val Glu Lys Gln Arg Asp Leu Leu Ile Glu
        295                 300                 305

AAA GGT GAT TTG AAC GCA AAT AGC AAT GCA GCA AGT GCA AGT AAC AGC    1853
Lys Gly Asp Leu Asn Ala Asn Ser Asn Ala Ala Ser Ala Ser Asn Ser
310                 315                 320                 325

ACA GAC AAC AAG TCT GAA ACT TTC AAC AAG ATT AAA CTG TTA GCC ATG    1901
Thr Asp Asn Lys Ser Glu Thr Phe Asn Lys Ile Lys Leu Leu Ala Met
                330                 335                 340

AAG AAA TTC CCC ACC CAT TTC CAC TAT TAC AAG AAT GAA GAC AAA CAT    1949
Lys Lys Phe Pro Thr His Phe His Tyr Tyr Lys Asn Glu Asp Lys His
            345                 350                 355

AAT CCT TCA CCA GAA GAG ATC AAA CAA CAA ACT ATC TTG AAT AAT AAT    1997
Asn Pro Ser Pro Glu Glu Ile Lys Gln Gln Thr Ile Leu Asn Asn Asn
        360                 365                 370

GCA GCC TCT TCT TTA CCA GAG GAA TTA TTG AAC GCA CTA GAT AAA GGT    2045
Ala Ala Ser Ser Leu Pro Glu Glu Leu Leu Asn Ala Leu Asp Lys Gly
        375                 380                 385

ATG GAA AAC TTG AGA CAA CAG CAG CCG CAG CAG CAG GTC CAA AGT TCG    2093
Met Glu Asn Leu Arg Gln Gln Gln Pro Gln Gln Gln Val Gln Ser Ser
390                 395                 400                 405

CAG CCA CAA CCA CAG CCC CAA CAG CTA CAG CAG CAA CCA AAT GGC CAA    2141
Gln Pro Gln Pro Gln Pro Gln Gln Leu Gln Gln Gln Pro Asn Gly Gln
                410                 415                 420

AGA CCA AAT TAT TAT CCT GAA CCG TTA CTA CAG CAG CAA CAA AGA GAT    2189
Arg Pro Asn Tyr Tyr Pro Glu Pro Leu Leu Gln Gln Gln Gln Arg Asp
            425                 430                 435

TCT CAG GAG CAA CAG CAG CAA GTT CCG ATG GCT ACA ACC AGG GCT ACT    2237
Ser Gln Glu Gln Gln Gln Gln Val Pro Met Ala Thr Thr Arg Ala Thr
        440                 445                 450

CAG TAT CCC CCA CAA ATA AAC AGC AAT AAT TTT AAT ACT AAT CAA GCA    2285
Gln Tyr Pro Pro Gln Ile Asn Ser Asn Asn Phe Asn Thr Asn Gln Ala
        455                 460                 465

TCT GTA CCT CCA CAA ATG AGA TCT AAT CCA CAA CAG CCG CCT CAA GAT    2333
Ser Val Pro Pro Gln Met Arg Ser Asn Pro Gln Gln Pro Pro Gln Asp
470                 475                 480                 485

AAA CCA GCT GGC CAG TCA ATT TGG TTG TAAGCAACAT ATATTGCTCA          2380
Lys Pro Ala Gly Gln Ser Ile Trp Leu
                490

AAACGCACAA AAATAAACAT ATGTATATAT AGACATACAC ACACACATAT ATATATATAT  2440
```

```
ATTATTATTA TTATTTACAT ATACGTACAC ACAATTCCAT ATCGAGTTAA TATATACAAT      2500

TCTGGCCTTC TTACCTAAAA AGATGATAGC TAAAAGAACC ACTTTTTTA  TGCATTTTTT      2560

TCTTCGGGAA GGAAATTAAG GGGGAGCGGA GCACCTCTTG GCCAATTTGT TTTTTTTTA      2620

TGTAATAAAG GGCTAACGAT CGAAGATCAA TCACGAATAT TGGACGGTTT TAAAGGAGGG      2680

CCTCTGAGAA GACAGCATCA ATTCGTATTT TCGATAATTA ACTTGCCTTA TAGTGTCTGA      2740

TTAGGAAACA ATCACGAGAC GATAACGACG GAATACCAAG GAAGTTTGTG CAAATATACA      2800

GCCGGCACAA ACAGCAGCTT CACTCAGGTT AACTCACATA CTGTTGAAAA TTGTCGGTAT      2860

GGAATTCGTT GCAGAAAGGG CTCAGCCAGT TGGTCAAACA ATCCAGCAGC AAAATGTTAA      2920

TACTTACGGG CAAGGCGTCC TACAACCGCA TCATGATTTA CAGCAGCGAC AACAACAACA      2980

ACAGCAGCGT CAGCATCAAC AACTGCTGAC GTCTCAGTTG CCCCAGAAAT CTCTCGTATC      3040

CAAAGGCAAA TATACACTAC ATGACTTCCA GATTATGAGA ACGCTTGGTA CTGGATCC        3098
```

(2) INFORMATION FOR SEQ ID NO:2:

(i) SEQUENCE CHARACTERISTICS:
        (A) LENGTH: 494 amino acids
        (B) TYPE: amino acid
        (D) TOPOLOGY: linear (ii) MOLECULE TYPE: protein (xi) SEQUENCE DESCRIPTION: SEQ ID NO:2:

```
Met Asp Leu Arg Val Gly Arg Lys Phe Arg Ile Gly Arg Lys Ile Gly
 1               5                  10                  15

Ser Gly Ser Phe Gly Asp Ile Tyr His Gly Thr Asn Leu Ile Ser Gly
            20                  25                  30

Glu Glu Val Ala Ile Lys Leu Glu Ser Ile Arg Ser Arg His Pro Gln
        35                  40                  45

Leu Asp Tyr Glu Ser Arg Val Tyr Arg Tyr Leu Ser Gly Gly Val Gly
    50                  55                  60

Ile Pro Phe Ile Arg Trp Phe Gly Arg Glu Gly Glu Tyr Asn Ala Met
65                  70                  75                  80

Val Ile Asp Leu Leu Gly Pro Ser Leu Glu Asp Leu Phe Asn Tyr Cys
                85                  90                  95

His Arg Arg Phe Ser Phe Lys Thr Val Ile Met Leu Ala Leu Gln Met
            100                 105                 110

Phe Cys Arg Ile Gln Tyr Ile His Gly Arg Ser Phe Ile His Arg Asp
        115                 120                 125

Ile Lys Pro Asp Asn Phe Leu Met Gly Val Gly Arg Arg Gly Ser Thr
    130                 135                 140

Val His Val Ile Asp Phe Gly Leu Ser Lys Lys Tyr Arg Asp Phe Asn
145                 150                 155                 160

Thr His Arg His Ile Pro Tyr Arg Glu Asn Lys Ser Leu Thr Gly Thr
                165                 170                 175

Ala Arg Tyr Ala Ser Val Asn Thr His Leu Gly Ile Glu Gln Ser Arg
            180                 185                 190

Arg Asp Asp Leu Glu Ser Leu Gly Tyr Val Leu Ile Tyr Phe Cys Lys
        195                 200                 205

Gly Ser Leu Pro Trp Gln Gly Leu Lys Ala Thr Thr Lys Lys Gln Lys
    210                 215                 220

Tyr Asp Arg Ile Met Glu Lys Lys Leu Asn Val Ser Val Glu Thr Leu
225                 230                 235                 240
```

| | | | | | | | | | | | | | | |
|---|---|---|---|---|---|---|---|---|---|---|---|---|---|---|
| Cys | Ser | Gly | Leu | Pro<br>245 | Leu | Glu | Phe | Gln | Glu<br>250 | Tyr | Met | Ala | Tyr | Cys<br>255 | Lys |
| Asn | Leu | Lys | Phe<br>260 | Asp | Glu | Lys | Pro | Asp<br>265 | Tyr | Leu | Phe | Leu<br>270 | Ala | Arg | Leu |
| Phe | Lys | Asp<br>275 | Leu | Ser | Ile | Lys | Leu<br>280 | Glu | Tyr | His | Asn | Asp<br>285 | His | Leu | Phe |
| Asp | Trp<br>290 | Thr | Met | Leu | Arg | Tyr<br>295 | Thr | Lys | Ala | Met | Val<br>300 | Glu | Lys | Gln | Arg |
| Asp<br>305 | Leu | Leu | Ile | Glu | Lys<br>310 | Gly | Asp | Leu | Asn | Ala<br>315 | Asn | Ser | Asn | Ala | Ala<br>320 |
| Ser | Ala | Ser | Asn | Ser<br>325 | Thr | Asp | Asn | Lys | Ser<br>330 | Glu | Thr | Phe | Asn | Lys<br>335 | Ile |
| Lys | Leu | Leu | Ala<br>340 | Met | Lys | Lys | Phe | Pro<br>345 | Thr | His | Phe | His<br>350 | Tyr | Tyr | Lys |
| Asn | Glu | Asp<br>355 | Lys | His | Asn | Pro | Ser<br>360 | Pro | Glu | Glu | Ile | Lys<br>365 | Gln | Gln | Thr |
| Ile | Leu<br>370 | Asn | Asn | Asn | Ala | Ala<br>375 | Ser | Ser | Leu | Pro | Glu<br>380 | Glu | Leu | Leu | Asn |
| Ala<br>385 | Leu | Asp | Lys | Gly | Met<br>390 | Glu | Asn | Leu | Arg | Gln<br>395 | Gln | Gln | Pro | Gln | Gln<br>400 |
| Gln | Val | Gln | Ser | Ser<br>405 | Gln | Pro | Gln | Pro | Gln<br>410 | Pro | Gln | Gln | Leu<br>415 | Gln | Gln |
| Gln | Pro | Asn | Gly<br>420 | Gln | Arg | Pro | Asn | Tyr<br>425 | Tyr | Pro | Glu | Pro<br>430 | Leu | Leu | Gln |
| Gln | Gln | Gln<br>435 | Arg | Asp | Ser | Gln | Glu<br>440 | Gln | Gln | Gln | Gln | Val<br>445 | Pro | Met | Ala |
| Thr | Thr<br>450 | Arg | Ala | Thr | Gln | Tyr<br>455 | Pro | Pro | Gln | Ile | Asn<br>460 | Ser | Asn | Asn | Phe |
| Asn<br>465 | Thr | Asn | Gln | Ala | Ser<br>470 | Val | Pro | Pro | Gln | Met<br>475 | Arg | Ser | Asn | Pro | Gln<br>480 |
| Gln | Pro | Pro | Gln | Asp<br>485 | Lys | Pro | Ala | Gly | Gln<br>490 | Ser | Ile | Trp | Leu | | |

( 2 ) INFORMATION FOR SEQ ID NO:3:

( i ) SEQUENCE CHARACTERISTICS:
        ( A ) LENGTH: 2469 base pairs
        ( B ) TYPE: nucleic acid
        ( C ) STRANDEDNESS: single
        ( D ) TOPOLOGY: linear ( i i ) MOLECULE TYPE: DNA (genomic)

( v i i ) IMMEDIATE SOURCE:
        ( B ) CLONE: Protein Kinase ( i x ) FEATURE:
        ( A ) NAME/KEY: CDS
        ( B ) LOCATION: 113..1207

( x i ) SEQUENCE DESCRIPTION: SEQ ID NO:3:

```
AATATTTCAA GCTATACCAA GCATACAATC AACTCCAAGC TTCGAGCGGC CGCCAGTGTG         60

CTCTAAAGGA AAAAGCGAGT GCCTTTAGCC TTAAAAGCGT TATAATATTA TT ATG           115
                                                         Met
                                                          1

GCT TTG GAC CTC CGG ATT GGG AAC AAG TAT CGC ATT GGT CGT AAA ATT         163
Ala Leu Asp Leu Arg Ile Gly Asn Lys Tyr Arg Ile Gly Arg Lys Ile
         5                  10                  15

GGC AGT GGA TCT TTC GGA GAC ATT TAT CTT GGG ACT AAT GTC GTT TCT         211
Gly Ser Gly Ser Phe Gly Asp Ile Tyr Leu Gly Thr Asn Val Val Ser
```

|  |  |  |  |  |  |  |  |  |  |  |  |  |  |  |  |  |
|---|---|---|---|---|---|---|---|---|---|---|---|---|---|---|---|---|
| GGT | GAA | GAG | GTC | GCT | ATC | AAG | CTA | GAA | TCA | ACT | CGT | GCT | AAA | CAC | CCT | 259 |
| Gly | Glu | Glu | Val | Ala | Ile | Lys | Leu | Glu | Ser | Thr | Arg | Ala | Lys | His | Pro |  |
|  |  | 35 |  |  |  | 40 |  |  |  |  | 45 |  |  |  |  |  |
| CAA | TTG | GAG | TAT | GAA | TAC | AGA | GTT | TAT | CGC | ATT | TTG | TCA | GGA | GGG | GTC | 307 |
| Gln | Leu | Glu | Tyr | Glu | Tyr | Arg | Val | Tyr | Arg | Ile | Leu | Ser | Gly | Gly | Val |  |
| 50 |  |  |  |  | 55 |  |  |  |  | 60 |  |  |  |  | 65 |  |
| GGA | ATC | CCG | TTT | GTT | CGT | TGG | TTC | GGT | GTA | GAA | TGT | GAT | TAC | AAC | GCT | 355 |
| Gly | Ile | Pro | Phe | Val | Arg | Trp | Phe | Gly | Val | Glu | Cys | Asp | Tyr | Asn | Ala |  |
|  |  |  |  | 70 |  |  |  |  | 75 |  |  |  |  |  | 80 |  |
| ATG | GTG | ATG | GAT | TTA | TTG | GGT | CCT | TCG | TTG | GAA | GAC | TTG | TTT | AAT | TTT | 403 |
| Met | Val | Met | Asp | Leu | Leu | Gly | Pro | Ser | Leu | Glu | Asp | Leu | Phe | Asn | Phe |  |
|  |  |  | 85 |  |  |  |  | 90 |  |  |  |  | 95 |  |  |  |
| TGC | AAT | CGA | AAG | TTT | TCT | TTG | AAA | ACA | GTT | CTT | CTC | CTT | GCG | GAC | CAG | 451 |
| Cys | Asn | Arg | Lys | Phe | Ser | Leu | Lys | Thr | Val | Leu | Leu | Leu | Ala | Asp | Gln |  |
|  |  | 100 |  |  |  |  | 105 |  |  |  |  | 110 |  |  |  |  |
| CTC | ATT | TCT | CGA | ATT | GAA | TTC | ATT | CAT | TCA | AAA | TCT | TTT | CTT | CAT | CGT | 499 |
| Leu | Ile | Ser | Arg | Ile | Glu | Phe | Ile | His | Ser | Lys | Ser | Phe | Leu | His | Arg |  |
|  | 115 |  |  |  |  | 120 |  |  |  |  | 125 |  |  |  |  |  |
| GAT | ATT | AAG | CCT | GAT | AAC | TTT | TTA | ATG | GGA | ATA | GGT | AAA | AGA | GGA | AAT | 547 |
| Asp | Ile | Lys | Pro | Asp | Asn | Phe | Leu | Met | Gly | Ile | Gly | Lys | Arg | Gly | Asn |  |
| 130 |  |  |  |  | 135 |  |  |  |  | 140 |  |  |  |  | 145 |  |
| CAA | GTT | AAC | ATA | ATT | GAT | TTC | GGA | TTG | GCT | AAG | AAG | TAT | CGT | GAT | CAC | 595 |
| Gln | Val | Asn | Ile | Ile | Asp | Phe | Gly | Leu | Ala | Lys | Lys | Tyr | Arg | Asp | His |  |
|  |  |  |  | 150 |  |  |  |  | 155 |  |  |  |  | 160 |  |  |
| AAA | ACT | CAC | CTG | CAC | ATT | CCT | TAT | CGC | GAG | AAC | AAG | AAT | CTT | ACA | GGT | 643 |
| Lys | Thr | His | Leu | His | Ile | Pro | Tyr | Arg | Glu | Asn | Lys | Asn | Leu | Thr | Gly |  |
|  |  |  | 165 |  |  |  |  | 170 |  |  |  |  | 175 |  |  |  |
| ACT | GCA | CGC | TAT | GCT | AGC | ATC | AAT | ACT | CAT | TTA | GGT | ATT | GAA | CAA | TCC | 691 |
| Thr | Ala | Arg | Tyr | Ala | Ser | Ile | Asn | Thr | His | Leu | Gly | Ile | Glu | Gln | Ser |  |
|  | 180 |  |  |  |  | 185 |  |  |  |  | 190 |  |  |  |  |  |
| CGC | CGT | GAT | GAC | CTC | GAA | TCT | TTA | GGT | TAT | GTG | CTC | GTC | TAC | TTT | TGT | 739 |
| Arg | Arg | Asp | Asp | Leu | Glu | Ser | Leu | Gly | Tyr | Val | Leu | Val | Tyr | Phe | Cys |  |
| 195 |  |  |  |  | 200 |  |  |  |  | 205 |  |  |  |  |  |  |
| CGT | GGT | AGC | CTG | CCT | TGG | CAG | GGA | TTG | AAG | GCT | ACC | ACG | AAA | AAG | CAA | 787 |
| Arg | Gly | Ser | Leu | Pro | Trp | Gln | Gly | Leu | Lys | Ala | Thr | Thr | Lys | Lys | Gln |  |
| 210 |  |  |  |  | 215 |  |  |  |  | 220 |  |  |  |  | 225 |  |
| AAG | TAT | GAA | AAG | ATT | ATG | GAG | AAG | AAG | ATC | TCT | ACG | CCT | ACA | GAG | GTC | 835 |
| Lys | Tyr | Glu | Lys | Ile | Met | Glu | Lys | Lys | Ile | Ser | Thr | Pro | Thr | Glu | Val |  |
|  |  |  |  | 230 |  |  |  |  | 235 |  |  |  |  | 240 |  |  |
| TTA | TGT | CGG | GGA | TTC | CCT | CAG | GAG | TTC | TCA | ATT | TAT | CTC | AAT | TAC | ACG | 883 |
| Leu | Cys | Arg | Gly | Phe | Pro | Gln | Glu | Phe | Ser | Ile | Tyr | Leu | Asn | Tyr | Thr |  |
|  |  |  | 245 |  |  |  |  | 250 |  |  |  |  | 255 |  |  |  |
| AGA | TCT | TTA | CGT | TTC | GAT | GAC | AAA | CCT | GAT | TAC | GCC | TAC | CTT | CGC | AAG | 931 |
| Arg | Ser | Leu | Arg | Phe | Asp | Asp | Lys | Pro | Asp | Tyr | Ala | Tyr | Leu | Arg | Lys |  |
|  |  | 260 |  |  |  |  | 265 |  |  |  |  | 270 |  |  |  |  |
| CTT | TTC | CGA | GAT | CTT | TTT | TGT | CGG | CAA | TCT | TAT | GAG | TTT | GAC | TAT | ATG | 979 |
| Leu | Phe | Arg | Asp | Leu | Phe | Cys | Arg | Gln | Ser | Tyr | Glu | Phe | Asp | Tyr | Met |  |
|  | 275 |  |  |  |  | 280 |  |  |  |  | 285 |  |  |  |  |  |
| TTT | GAT | TGG | ACC | TTG | AAG | AGA | AAG | ACT | CAA | CAA | GAC | CAA | CAA | CAT | CAG | 1027 |
| Phe | Asp | Trp | Thr | Leu | Lys | Arg | Lys | Thr | Gln | Gln | Asp | Gln | Gln | His | Gln |  |
| 290 |  |  |  |  | 295 |  |  |  |  | 300 |  |  |  |  | 305 |  |
| CAG | CAA | TTA | CAG | CAA | CAA | CTG | TCT | GCA | ACT | CCT | CAA | GCT | ATT | AAT | CCG | 1075 |
| Gln | Gln | Leu | Gln | Gln | Gln | Leu | Ser | Ala | Thr | Pro | Gln | Ala | Ile | Asn | Pro |  |
|  |  |  |  | 310 |  |  |  |  | 315 |  |  |  |  | 320 |  |  |
| CCG | CCA | GAG | AGG | TCT | TCA | TTT | AGA | AAT | TAT | CAA | AAA | CAA | AAC | TTT | GAT | 1123 |
| Pro | Pro | Glu | Arg | Ser | Ser | Phe | Arg | Asn | Tyr | Gln | Lys | Gln | Asn | Phe | Asp |  |
|  |  |  | 325 |  |  |  |  | 330 |  |  |  |  | 335 |  |  |  |
| GAA | AAA | GGC | GGA | GAC | ATT | AAT | ACA | ACC | GTT | CCT | GTT | ATA | AAT | GAT | CCA | 1171 |
| Glu | Lys | Gly | Gly | Asp | Ile | Asn | Thr | Thr | Val | Pro | Val | Ile | Asn | Asp | Pro |  |

|     | 340 |     |     |     |     | 345 |     |     |     |     | 350 |     |      |
|-----|-----|-----|-----|-----|-----|-----|-----|-----|-----|-----|-----|-----|------|
| TCT | GCA | ACC | GGA | GCT | CAA | TAT | ATC | AAC | AGA | CCT | AAT | TGATTAGCCT | 1217 |
| Ser | Ala | Thr | Gly | Ala | Gln | Tyr | Ile | Asn | Arg | Pro | Asn |     |      |
|     | 355 |     |     |     |     | 360 |     |     |     |     | 365 |     |      |

```
TTCATATTAT  TATTATATAG  CATGGGCACA  TTATTTTTAT  ATTTCTTCT  CATCTGGAGT   1277

CTTCCAATAC  TTGCCTTTTA  TCCTCCAGAC  GTCCTTTAAT  TTGTTGATA  GCGCAGGGCT   1337

TTTTCCTTGG  GATGGCGAAA  GTTACTTTGC  TTATAGTTTA  TTGAGGGTTC  ATAGCTTATT  1397

TGGCTGAAGA  TCTTGTGTTG  ACTTAAATTC  TATGCTAACC  TCATGATCAT  ATCCTCATTA  1457

TGGCAAGTTT  TGGTGAAAAA  TTTTTAATA   TTAGTACATT  TGCTAATAAT  ACATTGGTA   1517

TTTGTTTTTA  CTACCTGTGA  ATCTATTCAT  ACATTATCAT  ATATGTTTCG  AGCCAGGAAC  1577

AGAAAAAAGT  GAGAGAATTT  TCTGCAGAAA  TGATCATAAT  TTTATCTTCG  CTTAACACGA  1637

ATCCTGGTGA  CAGATTATCG  TGGTTTAAAG  CCTTTTTTTT  ACGACGCCAT  AAGCAAATTG  1697

GTTACTTTTT  TATGTGTGAT  GAGCCTTGGG  GTTTAATCTA  ATTAGAAGGC  ATTGCATTCA  1757

TATACTTTTA  ATAATATATT  ATCAGCTATT  TGCTGCTTTT  CTTTATAGAT  ACCGTCTTTT  1817

CCAAGCTGAA  CTCATTTAAT  CAGCGTCGTT  TAACCTTAGG  ATGCTTAAGA  TGCGTTTAAA  1877

TTCAATGACT  TAATGCTCGA  GGGATGAATG  GTTTGTTTTA  GTTCGTGTTC  TGGGTGCATG  1937

ATCTCGTGCT  TGACTGTTTT  ATTGAAGCGT  TCATTTCATG  AAGTGTCTTT  CGATGTTGTT  1997

CACACTTCTG  TTTGCTAAAT  ATAATAAATA  TTTTGCTTTT  CACTTAGAG   CACACTGGCG  2057

GCCGCTCGAA  GCTTGGACT   TCTTCGCCAT  TGGTCAAGTC  TCCAATCAAG  GTTGTCGGCT  2117

TGTCTACCTT  GCCAGAAATT  TACGAAAAGA  TGGAAAAGGG  ATCCAAATCG  TTGGTAGATA  2177

CTTGTTGACA  CTTCTAAATA  AGCGAATTTC  TTATGATTA   TGATTTTAT   TATTAAATAA  2237

GTTATAAAAA  AAATAAGGTA  TACAAATTTT  AAAGTGACTC  TTAGGTTTTA  AAACGAAAAT  2297

TCTTATTCTT  GAGTAACTCT  TTCCTGTAGG  TCAGGTTGCT  TTCTCAGGTA  TAGCATGAGG  2357

TCGCTCTTAT  TGACCACACC  TCTACCGGCA  TGCCGAGCAA  ATGCCTGCAA  ATCGCTCCCC  2417

ATTTCACCCA  ATTGTAGATA  TGCTAACTCC  AGCAATGAGC  CGATGAATCT  CC          2469
```

( 2 ) INFORMATION FOR SEQ ID NO:4:

( i ) SEQUENCE CHARACTERISTICS:
        ( A ) LENGTH: 365 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Met  Ala  Leu  Asp  Leu  Arg  Ile  Gly  Asn  Lys  Tyr  Arg  Ile  Gly  Arg  Lys
 1                  5                        10                       15

Ile  Gly  Ser  Gly  Ser  Phe  Gly  Asp  Ile  Tyr  Leu  Gly  Thr  Asn  Val  Val
               20                        25                       30

Ser  Gly  Glu  Glu  Val  Ala  Ile  Lys  Leu  Glu  Ser  Thr  Arg  Ala  Lys  His
          35                        40                       45

Pro  Gln  Leu  Glu  Tyr  Glu  Tyr  Arg  Val  Tyr  Arg  Ile  Leu  Ser  Gly  Gly
     50                        55                       60

Val  Gly  Ile  Pro  Phe  Val  Arg  Trp  Phe  Gly  Val  Glu  Cys  Asp  Tyr  Asn
 65                 70                       75                            80

Ala  Met  Val  Met  Asp  Leu  Leu  Gly  Pro  Ser  Leu  Glu  Asp  Leu  Phe  Asn
                    85                       90                           95

Phe  Cys  Asn  Arg  Lys  Phe  Ser  Leu  Lys  Thr  Val  Leu  Leu  Leu  Ala  Asp
               100                      105                      110
```

```
Gln  Leu  Ile  Ser  Arg  Ile  Glu  Phe  Ile  His  Ser  Lys  Ser  Phe  Leu  His
          115                      120                     125

Arg  Asp  Ile  Lys  Pro  Asp  Asn  Phe  Leu  Met  Gly  Ile  Gly  Lys  Arg  Gly
          130                      135                     140

Asn  Gln  Val  Asn  Ile  Ile  Asp  Phe  Gly  Leu  Ala  Lys  Lys  Tyr  Arg  Asp
145                           150                     155                     160

His  Lys  Thr  His  Leu  His  Ile  Pro  Tyr  Arg  Glu  Asn  Lys  Asn  Leu  Thr
                    165                      170                          175

Gly  Thr  Ala  Arg  Tyr  Ala  Ser  Ile  Asn  Thr  His  Leu  Gly  Ile  Glu  Gln
               180                      185                          190

Ser  Arg  Arg  Asp  Asp  Leu  Glu  Ser  Leu  Gly  Tyr  Val  Leu  Val  Tyr  Phe
          195                      200                     205

Cys  Arg  Gly  Ser  Leu  Pro  Trp  Gln  Gly  Leu  Lys  Ala  Thr  Thr  Lys  Lys
          210                      215                     220

Gln  Lys  Tyr  Glu  Lys  Ile  Met  Glu  Lys  Lys  Ile  Ser  Thr  Pro  Thr  Glu
225                           230                     235                     240

Val  Leu  Cys  Arg  Gly  Phe  Pro  Gln  Glu  Phe  Ser  Ile  Tyr  Leu  Asn  Tyr
               245                      250                          255

Thr  Arg  Ser  Leu  Arg  Phe  Asp  Asp  Lys  Pro  Asp  Tyr  Ala  Tyr  Leu  Arg
               260                      265                     270

Lys  Leu  Phe  Arg  Asp  Leu  Phe  Cys  Arg  Gln  Ser  Tyr  Glu  Phe  Asp  Tyr
               275                      280                     285

Met  Phe  Asp  Trp  Thr  Leu  Lys  Arg  Lys  Thr  Gln  Gln  Asp  Gln  Gln  His
     290                      295                     300

Gln  Gln  Gln  Leu  Gln  Gln  Gln  Leu  Ser  Ala  Thr  Pro  Gln  Ala  Ile  Asn
305                      310                     315                          320

Pro  Pro  Pro  Glu  Arg  Ser  Ser  Phe  Arg  Asn  Tyr  Gln  Lys  Gln  Asn  Phe
               325                      330                          335

Asp  Glu  Lys  Gly  Gly  Asp  Ile  Asn  Thr  Thr  Val  Pro  Val  Ile  Asn  Asp
               340                      345                     350

Pro  Ser  Ala  Thr  Gly  Ala  Gln  Tyr  Ile  Asn  Arg  Pro  Asn
               355                      360                     365
```

( 2 ) INFORMATION FOR SEQ ID NO:5:

( i ) SEQUENCE CHARACTERISTICS:
        ( A ) LENGTH: 1989 base pairs
        ( B ) TYPE: nucleic acid
        ( C ) STRANDEDNESS: single
        ( D ) TOPOLOGY: linear ( i i ) MOLECULE TYPE: DNA (genomic)

( v i i ) IMMEDIATE SOURCE:
        ( B ) CLONE: Protein Kinase ( i x ) FEATURE:
        ( A ) NAME/KEY: CDS
        ( B ) LOCATION: 50..1249

( x i ) SEQUENCE DESCRIPTION: SEQ ID NO:5:

```
CCGCCAGTGT  GCTCTAAAGG  TCATCTCTGT  GAATTAGAAT  CTTAGCAAA  ATG  ACG              55
                                                          Met  Thr
                                                           1

GTT  GTT  GAC  ATT  AAG  ATT  GGT  AAT  AAA  TAT  CGT  ATA  GGT  AGA  AAA  ATT    103
Val  Val  Asp  Ile  Lys  Ile  Gly  Asn  Lys  Tyr  Arg  Ile  Gly  Arg  Lys  Ile
          5                        10                      15

GGT  TCT  GGC  TCC  TTT  GGT  CAA  ATT  TAC  CTG  GGA  TTA  AAT  ACG  GTA  AAT    151
Gly  Ser  Gly  Ser  Phe  Gly  Gln  Ile  Tyr  Leu  Gly  Leu  Asn  Thr  Val  Asn
     20                       25                       30
```

| | | | | | | | | | | | | | | | | |
|---|---|---|---|---|---|---|---|---|---|---|---|---|---|---|---|---|
| GGA | GAA | CAA | GTT | GCT | GTG | AAA | TTG | GAG | CCT | TTA | AAG | GCT | CGT | CAT | CAT | 199 |
| Gly | Glu | Gln | Val | Ala | Val | Lys | Leu | Glu | Pro | Leu | Lys | Ala | Arg | His | His | |
| 35 | | | | 40 | | | | | 45 | | | | | | 50 | |
| CAG | TTA | GAA | TAT | GAG | TTT | CGT | GTG | TAT | AAT | ATT | CTT | AAA | GGA | AAT | ATT | 247 |
| Gln | Leu | Glu | Tyr | Glu | Phe | Arg | Val | Tyr | Asn | Ile | Leu | Lys | Gly | Asn | Ile | |
| | | | | 55 | | | | | 60 | | | | | 65 | | |
| GGC | ATA | CCC | ACA | ATT | CGC | TGG | TTC | GGT | GTA | ACC | AAT | AGT | TAT | AAT | GCT | 295 |
| Gly | Ile | Pro | Thr | Ile | Arg | Trp | Phe | Gly | Val | Thr | Asn | Ser | Tyr | Asn | Ala | |
| | | | 70 | | | | | 75 | | | | | 80 | | | |
| ATG | GTC | ATG | GAT | TTA | TTA | GGC | CCT | TCT | CTG | GAA | GAT | TTA | TTC | TGC | TAT | 343 |
| Met | Val | Met | Asp | Leu | Leu | Gly | Pro | Ser | Leu | Glu | Asp | Leu | Phe | Cys | Tyr | |
| | | 85 | | | | | 90 | | | | | 95 | | | | |
| TGT | GGA | AGA | AAG | TTT | ACT | CTT | AAA | ACG | GTT | CTT | TTA | CTT | GCT | GAT | CAA | 391 |
| Cys | Gly | Arg | Lys | Phe | Thr | Leu | Lys | Thr | Val | Leu | Leu | Leu | Ala | Asp | Gln | |
| | | 100 | | | | 105 | | | | | 110 | | | | | |
| CTC | ATC | AGT | CGC | ATT | GAA | TAT | GTT | CAC | TCC | AAG | TCA | TTC | TTA | CAT | CGA | 439 |
| Leu | Ile | Ser | Arg | Ile | Glu | Tyr | Val | His | Ser | Lys | Ser | Phe | Leu | His | Arg | |
| 115 | | | | | 120 | | | | | 125 | | | | | 130 | |
| GAC | ATT | AAG | CCT | GAT | AAT | TTT | TTA | ATG | AAG | AAG | CAC | AGC | AAT | GTT | GTT | 487 |
| Asp | Ile | Lys | Pro | Asp | Asn | Phe | Leu | Met | Lys | Lys | His | Ser | Asn | Val | Val | |
| | | | | 135 | | | | | 140 | | | | | 145 | | |
| ACG | ATG | ATT | GAC | TTC | GGA | TTG | GCG | AAA | AAA | TAC | AGG | GAT | TTT | AAA | ACT | 535 |
| Thr | Met | Ile | Asp | Phe | Gly | Leu | Ala | Lys | Lys | Tyr | Arg | Asp | Phe | Lys | Thr | |
| | | | 150 | | | | | 155 | | | | | 160 | | | |
| CAT | GTT | CAT | ATT | CCA | TAT | CGA | GAT | AAT | AAG | AAT | CTT | ACG | GGA | ACG | GCT | 583 |
| His | Val | His | Ile | Pro | Tyr | Arg | Asp | Asn | Lys | Asn | Leu | Thr | Gly | Thr | Ala | |
| | | 165 | | | | | 170 | | | | | 175 | | | | |
| CGA | TAT | GCT | AGT | ATT | AAC | ACC | CAT | ATT | GGT | ATT | GAA | CAA | TCT | CGC | CGT | 631 |
| Arg | Tyr | Ala | Ser | Ile | Asn | Thr | His | Ile | Gly | Ile | Glu | Gln | Ser | Arg | Arg | |
| | 180 | | | | | 185 | | | | | 190 | | | | | |
| GAT | GAC | CTC | GAA | TCG | TTA | GGT | TAT | GTT | TTA | CTT | TAT | TTT | TGT | CGC | GGC | 679 |
| Asp | Asp | Leu | Glu | Ser | Leu | Gly | Tyr | Val | Leu | Leu | Tyr | Phe | Cys | Arg | Gly | |
| 195 | | | | | 200 | | | | | 205 | | | | | 210 | |
| AGT | TTG | CCC | TGG | CAA | GGC | TTA | CAA | GCT | GAT | ACA | AAG | GAG | CAA | AAG | TAT | 727 |
| Ser | Leu | Pro | Trp | Gln | Gly | Leu | Gln | Ala | Asp | Thr | Lys | Glu | Gln | Lys | Tyr | |
| | | | | 215 | | | | | 220 | | | | | 225 | | |
| CAA | CGG | ATA | CGT | GAT | ACC | AAG | ATT | GGC | ACT | CCT | TTG | GAA | GTC | CTT | TGC | 775 |
| Gln | Arg | Ile | Arg | Asp | Thr | Lys | Ile | Gly | Thr | Pro | Leu | Glu | Val | Leu | Cys | |
| | | | 230 | | | | | 235 | | | | | 240 | | | |
| AAA | GGT | CTT | CCC | GAA | GAG | TTT | ATC | ACT | TAC | ATG | TGT | TAC | ACT | CGT | CAG | 823 |
| Lys | Gly | Leu | Pro | Glu | Glu | Phe | Ile | Thr | Tyr | Met | Cys | Tyr | Thr | Arg | Gln | |
| | | 245 | | | | | 250 | | | | | 255 | | | | |
| CTT | TCG | TTT | ACC | GAG | AAG | CCA | AAC | TAT | GCT | TAT | TTG | AGA | AAG | CTG | TTT | 871 |
| Leu | Ser | Phe | Thr | Glu | Lys | Pro | Asn | Tyr | Ala | Tyr | Leu | Arg | Lys | Leu | Phe | |
| | 260 | | | | | 265 | | | | | 270 | | | | | |
| CGT | GAT | TTA | CTT | ATT | CGT | AAA | GGA | TAC | CAG | TAT | GAC | TAT | GTT | TTT | GAC | 919 |
| Arg | Asp | Leu | Leu | Ile | Arg | Lys | Gly | Tyr | Gln | Tyr | Asp | Tyr | Val | Phe | Asp | |
| 275 | | | | | 280 | | | | | 285 | | | | | 290 | |
| TGG | ATG | ATA | TTA | AAA | TAC | CAA | AAG | CGA | GCT | GCT | GCT | GCT | GCC | GCC | GCT | 967 |
| Trp | Met | Ile | Leu | Lys | Tyr | Gln | Lys | Arg | Ala | Ala | Ala | Ala | Ala | Ala | Ala | |
| | | | | 295 | | | | | 300 | | | | | 305 | | |
| TCT | GCT | ACA | GCA | CCT | CCA | CAG | GTT | ACA | TCT | CCT | ATG | GTG | TCA | CAA | ACT | 1015 |
| Ser | Ala | Thr | Ala | Pro | Pro | Gln | Val | Thr | Ser | Pro | Met | Val | Ser | Gln | Thr | |
| | | | 310 | | | | | 315 | | | | | 320 | | | |
| CAA | CCG | GTT | AAT | CCC | ATT | ACT | CCT | AAT | TAT | TCA | TCC | ATT | CCC | TTA | CCT | 1063 |
| Gln | Pro | Val | Asn | Pro | Ile | Thr | Pro | Asn | Tyr | Ser | Ser | Ile | Pro | Leu | Pro | |
| | | 325 | | | | | 330 | | | | | 335 | | | | |
| GCT | GAG | CGG | AAT | CCA | AAG | ACT | CCA | CAA | TCT | TTC | TCC | ACT | AAT | ATT | GTT | 1111 |
| Ala | Glu | Arg | Asn | Pro | Lys | Thr | Pro | Gln | Ser | Phe | Ser | Thr | Asn | Ile | Val | |
| | 340 | | | | | 345 | | | | | 350 | | | | | |

```
CAA TGT GCT TCT CCC TCA CCT CTT CCT CTC TCC TTT CGT TCT CCT GTT       1159
Gln Cys Ala Ser Pro Ser Pro Leu Pro Leu Ser Phe Arg Ser Pro Val
355             360                 365                 370

CCC AAC AAA GAT TAT GAA TAC ATT CCA TCT TCG TTG CAA CCT CAA TAC       1207
Pro Asn Lys Asp Tyr Glu Tyr Ile Pro Ser Ser Leu Gln Pro Gln Tyr
                    375                 380                 385

AGT GCT CAA CTG AGG CGT GTT TTA GAT GAA GAA CCA GCT CCT               1249
Ser Ala Gln Leu Arg Arg Val Leu Asp Glu Glu Pro Ala Pro
            390                 395                 400

TGATTTTTTG ACTTTACTTT TCATCAATTC CTCTCTTACA CTACGTCTTT TAGTCTTAAA     1309
TTCCAAACCA TCTGTTGACG TTTTAAAGTT CCACAAATAT CTTTAATAAT TCCTGGCTTT     1369
CTTTTTTGTC TATGGATGGC CGGATTGCTA CACTAATACA CTTTGAGGTT TAGCTATTGT     1429
TTTGAGCTAT TCCATTTTGC CTAGAAGTTG AGTTTAATG CCTTCTTTTT AAATAGACAT      1489
ATTGTGTAAA CCTCATACAT GCTTACTGA AAAGACATAA TTAGAGGACA AAATTTAAAT      1549
CGTGCTGTTT GTTTATATTC AGCTCGTTCC GGTCAAGTTC TTGCCAAAGA ATTGAGTCAG     1609
TCGTGCTATT CATTTCTAAA TTTCTTCTTC CCAGAATTTT ATTTTATTGT TTTCGTTCCC     1669
CATTGGTTCT TACATTCCGT TTTTATTCAA AACTGAAAAG TTTGTACCTC CATTGCTAGA     1729
AGTAATATAC ACAAGGAGCA TGTTTCTTTT TTACACTAT CATTGCGTG GCTCTAAACC       1789
AGTCTTTATT GCCTACCTTT GCAATAAAAG ATATAATATC AATTGCATAA GAAATAATTC     1849
ATTAATAAAT GATAAATTTC ATCGATTAAA TAAAAAAAAA AAACTTTAGA GCTTTAGAGC     1909
ACAACTGGCG GCCGCTCGAA GCTTTGGACT TCTTCGCCAT GGTCAAGTC TCAATCAAGG      1969
TTGTCGGCTT GTCTACCTTC                                                 1989
```

( 2 ) INFORMATION FOR SEQ ID NO:6:

( i ) SEQUENCE CHARACTERISTICS:
        ( A ) LENGTH: 400 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

```
Met Thr Val Val Asp Ile Lys Ile Gly Asn Lys Tyr Arg Ile Gly Arg
 1               5                  10                  15

Lys Ile Gly Ser Gly Ser Phe Gly Gln Ile Tyr Leu Gly Leu Asn Thr
                20                  25                  30

Val Asn Gly Glu Gln Val Ala Val Lys Leu Glu Pro Leu Lys Ala Arg
            35                  40                  45

His His Gln Leu Glu Tyr Glu Phe Arg Val Tyr Asn Ile Leu Lys Gly
        50                  55                  60

Asn Ile Gly Ile Pro Thr Ile Arg Trp Phe Gly Val Thr Asn Ser Tyr
 65                 70                  75                  80

Asn Ala Met Val Met Asp Leu Leu Gly Pro Ser Leu Glu Asp Leu Phe
                85                  90                  95

Cys Tyr Cys Gly Arg Lys Phe Thr Leu Lys Thr Val Leu Leu Leu Ala
            100                 105                 110

Asp Gln Leu Ile Ser Arg Ile Glu Tyr Val His Ser Lys Ser Phe Leu
        115                 120                 125

His Arg Asp Ile Lys Pro Asp Asn Phe Leu Met Lys Lys His Ser Asn
    130                 135                 140

Val Val Thr Met Ile Asp Phe Gly Leu Ala Lys Lys Tyr Arg Asp Phe
145                 150                 155                 160
```

| | | | | | | | | | | | | | | |
|---|---|---|---|---|---|---|---|---|---|---|---|---|---|---|
|Lys|Thr|His|Val|His|Ile|Pro|Tyr|Arg|Asp|Asn|Lys|Asn|Leu|Thr|Gly|
| | | |165| | | | |170| | | | |175| |
|Thr|Ala|Arg|Tyr|Ala|Ser|Ile|Asn|Thr|His|Ile|Gly|Ile|Glu|Gln|Ser|
| | | |180| | | |185| | | | |190| | |
|Arg|Arg|Asp|Asp|Leu|Glu|Ser|Leu|Gly|Tyr|Val|Leu|Leu|Tyr|Phe|Cys|
| | |195| | | |200| | | | |205| | | |
|Arg|Gly|Ser|Leu|Pro|Trp|Gln|Gly|Leu|Gln|Ala|Asp|Thr|Lys|Glu|Gln|
| |210| | | | |215| | | |220| | | | |
|Lys|Tyr|Gln|Arg|Ile|Arg|Asp|Thr|Lys|Ile|Gly|Thr|Pro|Leu|Glu|Val|
|225| | | |230| | | |235| | | | |240| |
|Leu|Cys|Lys|Gly|Leu|Pro|Glu|Glu|Phe|Ile|Thr|Tyr|Met|Cys|Tyr|Thr|
| | | |245| | | |250| | | |255| | | |
|Arg|Gln|Leu|Ser|Phe|Thr|Glu|Lys|Pro|Asn|Tyr|Ala|Tyr|Leu|Arg|Lys|
| | |260| | | |265| | | | |270| | | |
|Leu|Phe|Arg|Asp|Leu|Leu|Ile|Arg|Lys|Gly|Tyr|Gln|Tyr|Asp|Tyr|Val|
| | |275| | | |280| | | |285| | | | |
|Phe|Asp|Trp|Met|Ile|Leu|Lys|Tyr|Gln|Lys|Arg|Ala|Ala|Ala|Ala|Ala|
| |290| | | |295| | | |300| | | | | |
|Ala|Ala|Ser|Ala|Thr|Ala|Pro|Pro|Gln|Val|Thr|Ser|Pro|Met|Val|Ser|
|305| | | |310| | | |315| | | | |320| |
|Gln|Thr|Gln|Pro|Val|Asn|Pro|Ile|Thr|Pro|Asn|Tyr|Ser|Ser|Ile|Pro|
| | | |325| | | |330| | | | |335| | |
|Leu|Pro|Ala|Glu|Arg|Asn|Pro|Lys|Thr|Pro|Gln|Ser|Phe|Ser|Thr|Asn|
| | |340| | | |345| | | |350| | | | |
|Ile|Val|Gln|Cys|Ala|Ser|Pro|Ser|Pro|Leu|Pro|Leu|Ser|Phe|Arg|Ser|
| |355| | | |360| | | |365| | | | | |
|Pro|Val|Pro|Asn|Lys|Asp|Tyr|Glu|Tyr|Ile|Pro|Ser|Ser|Leu|Gln|Pro|
|370| | | |375| | | |380| | | | | | |
|Gln|Tyr|Ser|Ala|Gln|Leu|Arg|Arg|Val|Leu|Asp|Glu|Glu|Pro|Ala|Pro|
|385| | | |390| | | |395| | | | |400| |

(2) INFORMATION FOR SEQ ID NO:7:

(i) SEQUENCE CHARACTERISTICS:
        (A) LENGTH: 1210 base pairs
        (B) TYPE: nucleic acid
        (C) STRANDEDNESS: single
        (D) TOPOLOGY: linear (ii) MOLECULE TYPE: DNA (genomic)

(vii) IMMEDIATE SOURCE:
        (B) CLONE: Protein Kinase (ix) FEATURE:
        (A) NAME/KEY: CDS
        (B) LOCATION: 173..1147

(xi) SEQUENCE DESCRIPTION: SEQ ID NO:7:

```
GGCGGTGATC AGTTCCCCTC TGCTGATTCT GGGCCCGAAC CCGGTAAAGG CCTCCGTGTT      60

CCGTTTCCTG CCGCCCTCCT CCGTAGCCTT GCCTAGTGTA GGAGCCCCGA GGCCTCCGTC     120

CTCTTCCCAG AGGTGTCGGG GCTTGCCCCA GCCTCCATCT TCGTCTCTCA GG ATG         175
                                                           Met
                                                            1

GCG AGT AGC AGC GGC TCC AAG GCT GAA TTC ATT GTC GGA GGG AAA TAT      223
Ala Ser Ser Ser Gly Ser Lys Ala Glu Phe Ile Val Gly Gly Lys Tyr
                5                  10                  15

AAA CTG GTA CGG AAG ATC GGG TCT GGC TCC TTC GGG GAC ATC TAT TTG      271
Lys Leu Val Arg Lys Ile Gly Ser Gly Ser Phe Gly Asp Ile Tyr Leu
```

```
GCG ATC AAC ATC ACC AAC GGC GAG GAA GTG GCA GTG AAG CTA GAA TCT           319
Ala Ile Asn Ile Thr Asn Gly Glu Glu Val Ala Val Lys Leu Glu Ser
        35              40              45

CAG AAG GCC AGG CAT CCC CAG TTG CTG TAC GAG AGC AAG CTC TAT AAG           367
Gln Lys Ala Arg His Pro Gln Leu Leu Tyr Glu Ser Lys Leu Tyr Lys
 50              55              60                              65

ATT CTT CAA GGT GGG GTT GGC ATC CCC CAC ATA CGG TGG TAT GGT CAG           415
Ile Leu Gln Gly Gly Val Gly Ile Pro His Ile Arg Trp Tyr Gly Gln
                     70              75                      80

GAA AAA GAC TAC AAT GTA CTA GTC ATG GAT CTT CTG GGA CCT AGC CTC           463
Glu Lys Asp Tyr Asn Val Leu Val Met Asp Leu Leu Gly Pro Ser Leu
                 85              90              95

GAA GAC CTC TTC AAT TTC TGT TCA AGA AGG TTC ACA ATG AAA ACT GTA           511
Glu Asp Leu Phe Asn Phe Cys Ser Arg Arg Phe Thr Met Lys Thr Val
            100             105             110

CTT ATG TTA GCT GAC CAG ATG ATC AGT AGA ATT GAA TAT GTG CAT ACA           559
Leu Met Leu Ala Asp Gln Met Ile Ser Arg Ile Glu Tyr Val His Thr
    115                 120             125

AAG AAT TTT ATA CAC AGA GAC ATT AAA CCA GAT AAC TTC CTA ATG GGT           607
Lys Asn Phe Ile His Arg Asp Ile Lys Pro Asp Asn Phe Leu Met Gly
130             135             140                         145

ATT GGG CGT CAC TGT AAT AAG TTA TTC CTT ATT GAT TTT GGT TTG GCC           655
Ile Gly Arg His Cys Asn Lys Leu Phe Leu Ile Asp Phe Gly Leu Ala
                150             155                     160

AAA AAG TAC AGA GAC AAC AGG ACA AGG CAA CAC ATA CCA TAC AGA GAA           703
Lys Lys Tyr Arg Asp Asn Arg Thr Arg Gln His Ile Pro Tyr Arg Glu
            165             170             175

GAT AAA AAC CTC ACT GGC ACT GCC CGA TAT GCT AGC ATC AAT GCA CAT           751
Asp Lys Asn Leu Thr Gly Thr Ala Arg Tyr Ala Ser Ile Asn Ala His
180             185                         190

CTT GGT ATT GAG CAG AGT CGC CGA GAT GAC ATG GAA TCA TTA GGA TAT           799
Leu Gly Ile Glu Gln Ser Arg Arg Asp Asp Met Glu Ser Leu Gly Tyr
    195                 200             205

GTT TTG ATG TAT TTT AAT AGA ACC AGC CTG CCA TGG CAA GGG CTA AAG           847
Val Leu Met Tyr Phe Asn Arg Thr Ser Leu Pro Trp Gln Gly Leu Lys
210             215             220                         225

GCT GCA ACA AAG AAA CAA AAA TAT GAA AAG ATT AGT GAA AAG AAG ATG           895
Ala Ala Thr Lys Lys Gln Lys Tyr Glu Lys Ile Ser Glu Lys Lys Met
                230             235                     240

TCC ACG CCT GTT GAA GTT TTA TGT AAG GGG TTT CCT GCA GAA TTT GCG           943
Ser Thr Pro Val Glu Val Leu Cys Lys Gly Phe Pro Ala Glu Phe Ala
            245             250             255

ATG TAC TTA AAC TAT TGT CGT GGG CTA CGC TTT GAG GAA GCC CCA GAT           991
Met Tyr Leu Asn Tyr Cys Arg Gly Leu Arg Phe Glu Glu Ala Pro Asp
    260             265             270

TAC ATG TAT CTG AGG CAG CTA TTC CGC ATT CTT TTC AGG ACC CTG AAC          1039
Tyr Met Tyr Leu Arg Gln Leu Phe Arg Ile Leu Phe Arg Thr Leu Asn
275             280             285

CAT CAA TAT GAC TAC ACA TTT GAT TGG ACA ATG TTA AAG CAG AAA GCA          1087
His Gln Tyr Asp Tyr Thr Phe Asp Trp Thr Met Leu Lys Gln Lys Ala
290             295             300                         305

GCA CAG CAG GCA GCC TCT TCC AGT GGG CAG GGT CAG CAG GCC CAA ACC          1135
Ala Gln Gln Ala Ala Ser Ser Ser Gly Gln Gly Gln Gln Ala Gln Thr
                310             315                     320

CCC ACA GGT TTC TAAGCATGAA TTGAGGAACA GAAGAAGCAG AGCAGATGAT             1187
Pro Thr Gly Phe
            325

CGAGCAGCAT TTGTTTCTCC CAA                                               1210
```

( 2 ) INFORMATION FOR SEQ ID NO:8:

( i ) SEQUENCE CHARACTERISTICS:
        ( A ) LENGTH: 325 amino acids
        ( B ) TYPE: amino acid
        ( D ) TOPOLOGY: linear ( i i ) MOLECULE TYPE: protein ( x i ) SEQUENCE DESCRIPTION: SEQ ID NO:8:

```
Met Ala Ser Ser Ser Gly Ser Lys Ala Glu Phe Ile Val Gly Gly Lys
 1               5                  10                  15
Tyr Lys Leu Val Arg Lys Ile Gly Ser Gly Ser Phe Gly Asp Ile Tyr
                20                  25                  30
Leu Ala Ile Asn Ile Thr Asn Gly Glu Glu Val Ala Val Lys Leu Glu
             35                  40                  45
Ser Gln Lys Ala Arg His Pro Gln Leu Leu Tyr Glu Ser Lys Leu Tyr
         50                  55                  60
Lys Ile Leu Gln Gly Gly Val Gly Ile Pro His Ile Arg Trp Tyr Gly
 65                  70                  75                  80
Gln Glu Lys Asp Tyr Asn Val Leu Val Met Asp Leu Leu Gly Pro Ser
                 85                  90                  95
Leu Glu Asp Leu Phe Asn Phe Cys Ser Arg Arg Phe Thr Met Lys Thr
            100                 105                 110
Val Leu Met Leu Ala Asp Gln Met Ile Ser Arg Ile Glu Tyr Val His
            115                 120                 125
Thr Lys Asn Phe Ile His Arg Asp Ile Lys Pro Asp Asn Phe Leu Met
    130                 135                 140
Gly Ile Gly Arg His Cys Asn Lys Leu Phe Leu Ile Asp Phe Gly Leu
145                 150                 155                 160
Ala Lys Lys Tyr Arg Asp Asn Arg Thr Arg Gln His Ile Pro Tyr Arg
                165                 170                 175
Glu Asp Lys Asn Leu Thr Gly Thr Ala Arg Tyr Ala Ser Ile Asn Ala
            180                 185                 190
His Leu Gly Ile Glu Gln Ser Arg Arg Asp Asp Met Glu Ser Leu Gly
        195                 200                 205
Tyr Val Leu Met Tyr Phe Asn Arg Thr Ser Leu Pro Trp Gln Gly Leu
    210                 215                 220
Lys Ala Ala Thr Lys Lys Gln Lys Tyr Glu Lys Ile Ser Glu Lys Lys
225                 230                 235                 240
Met Ser Thr Pro Val Glu Val Leu Cys Lys Gly Phe Pro Ala Glu Phe
                245                 250                 255
Ala Met Tyr Leu Asn Tyr Cys Arg Gly Leu Arg Phe Glu Glu Ala Pro
            260                 265                 270
Asp Tyr Met Tyr Leu Arg Gln Leu Phe Arg Ile Leu Phe Arg Thr Leu
        275                 280                 285
Asn His Gln Tyr Asp Tyr Thr Phe Asp Trp Thr Met Leu Lys Gln Lys
    290                 295                 300
Ala Ala Gln Gln Ala Ala Ser Ser Ser Gly Gln Gly Gln Gln Ala Gln
305                 310                 315                 320
Thr Pro Thr Gly Phe
                325
```

( 2 ) INFORMATION FOR SEQ ID NO:9:

( i ) SEQUENCE CHARACTERISTICS:
        ( A ) LENGTH: 1779 base pairs (B) TYPE: nucleic acid
(C) STRANDEDNESS: single
(D) TOPOLOGY: linear (ii) MOLECULE TYPE: DNA (genomic)

(vii) IMMEDIATE SOURCE:
(B) CLONE: Protein Kinase (ix) FEATURE:
(A) NAME/KEY: CDS
(B) LOCATION: 263..1273

(xi) SEQUENCE DESCRIPTION: SEQ ID NO:9:

| | | | | | |
|---|---|---|---|---|---|
| GAATTCCGAG | AAACAAGTGG | CCCAGCTGGT | AACCGCCGAG | AAGCCCTTCA | CAAACTGCGG | 60 |
| CCTGGCAAAA | AGAAACCTGA | CTGAGCGGCG | GTGATCAGGT | TCCCCTCTGC | TGATTCTGGG | 120 |
| CCCCGAACCC | CGGTAAAGGC | CTCCGTGTTC | CGTTTCCTGC | CGCCCTCCTC | CGTAGCCTTG | 180 |
| CCTAGTGTAG | GAGCCCCGAG | GCCTCCGTCC | TCTTCCCAGA | GGTGTCGGGG | CTTGGCCCCA | 240 |
| GCCTCCATCT | TCGTCTCTCA | GG ATG GCG AGT AGC AGC GGC TCC AAG GCT GAA | | | | 292 |

```
                                        Met Ala Ser Ser Ser Gly Ser Lys Ala Glu
                                         1               5                  10

TTC ATT GTC GGA GGG AAA TAT AAA CTG GTA CGG AAG ATC GGG TCT GGC              340
Phe Ile Val Gly Gly Lys Tyr Lys Leu Val Arg Lys Ile Gly Ser Gly
             15                  20                  25

TCC TTC GGG GAC ATC TAT TTG GCG ATC AAC ATC ACC AAC GGC GAG GAA              388
Ser Phe Gly Asp Ile Tyr Leu Ala Ile Asn Ile Thr Asn Gly Glu Glu
        30                  35                  40

GTG GCA GTG AAG CTA GAA TCT CAG AAG GCC AGG CAT CCC CAG TTG CTG              436
Val Ala Val Lys Leu Glu Ser Gln Lys Ala Arg His Pro Gln Leu Leu
    45                  50                  55

TAC GAG AGC AAG CTC TAT AAG ATT CTT CAA GGT GGG GTT GGC ATC CCC              484
Tyr Glu Ser Lys Leu Tyr Lys Ile Leu Gln Gly Gly Val Gly Ile Pro
60                  65                  70

CAC ATA CGG TGG TAT GGT CAG GAA AAA GAC TAC AAT GTA CTA GTC ATG              532
His Ile Arg Trp Tyr Gly Gln Glu Lys Asp Tyr Asn Val Leu Val Met
75                  80                  85                  90

GAT CTT CTG GGA CCT AGC CTC GAA GAC CTC TTC AAT TTC TGT TCA AGA              580
Asp Leu Leu Gly Pro Ser Leu Glu Asp Leu Phe Asn Phe Cys Ser Arg
                95                 100                 105

AGG TTC ACA ATG AAA ACT GTA CTT ATG TTA GCT GAC CAG ATG ATC AGT              628
Arg Phe Thr Met Lys Thr Val Leu Met Leu Ala Asp Gln Met Ile Ser
            110                 115                 120

AGA ATT GAA TAT GTG CAT ACA AAG AAT TTT ATA CAC AGA GAC ATT AAA              676
Arg Ile Glu Tyr Val His Thr Lys Asn Phe Ile His Arg Asp Ile Lys
        125                 130                 135

CCA GAT AAC TTC CTA ATG GGT ATT GGG CGT CAC TGT AAT AAG TTA TTC              724
Pro Asp Asn Phe Leu Met Gly Ile Gly Arg His Cys Asn Lys Leu Phe
    140                 145                 150

CTT ATT GAT TTT GGT TTG GCC AAA AAG TAC AGA GAC AAC AGG ACA AGG              772
Leu Ile Asp Phe Gly Leu Ala Lys Lys Tyr Arg Asp Asn Arg Thr Arg
155                 160                 165                 170

CAA CAC ATA CCA TAC AGA GAA GAT AAA AAC CTC ACT GGC ACT GCC CGA              820
Gln His Ile Pro Tyr Arg Glu Asp Lys Asn Leu Thr Gly Thr Ala Arg
                175                 180                 185

TAT GCT AGC ATC AAT GCA CAT CTT GGT ATT GAG CAG AGT CGC CGA GAT              868
Tyr Ala Ser Ile Asn Ala His Leu Gly Ile Glu Gln Ser Arg Arg Asp
            190                 195                 200

GAC ATG GAA TCA TTA GGA TAT GTT TTG ATG TAT TTT AAT AGA ACC AGC              916
Asp Met Glu Ser Leu Gly Tyr Val Leu Met Tyr Phe Asn Arg Thr Ser
        205                 210                 215

CTG CCA TGG CAA GGG CTA AAG GCT GCA ACA AAG AAA CAA AAA TAT GAA              964
```

| | | | | | | | | | | | | | | | | |
|---|---|---|---|---|---|---|---|---|---|---|---|---|---|---|---|---|
| Leu | Pro | Trp | Gln | Gly | Leu | Lys | Ala | Ala | Thr | Lys | Lys | Gln | Lys | Tyr | Glu | |
| | 220 | | | | | 225 | | | | 230 | | | | | | |

```
AAG ATT AGT GAA AAG AAG ATG TCC ACG CCT GTT GAA GTT TTA TGT AAG        1012
Lys Ile Ser Glu Lys Lys Met Ser Thr Pro Val Glu Val Leu Cys Lys
235             240             245             250

GGG TTT CCT GCA GAA TTT GCG ATG TAC TTA AAC TAT TGT CGT GGG CTA        1060
Gly Phe Pro Ala Glu Phe Ala Met Tyr Leu Asn Tyr Cys Arg Gly Leu
                255             260             265

CGC TTT GAG GAA GCC CCA GAT TAC ATG TAT CTG AGG CAG CTA TTC CGC        1108
Arg Phe Glu Glu Ala Pro Asp Tyr Met Tyr Leu Arg Gln Leu Phe Arg
            270             275             280

ATT CTT TTC AGG ACC CTG AAC CAT CAA TAT GAC TAC ACA TTT GAT TGG        1156
Ile Leu Phe Arg Thr Leu Asn His Gln Tyr Asp Tyr Thr Phe Asp Trp
        285             290             295

ACA ATG TTA AAG CAG AAA GCA GCA CAG CAG GCA GCC TCT TCC AGT GGG        1204
Thr Met Leu Lys Gln Lys Ala Ala Gln Gln Ala Ala Ser Ser Ser Gly
    300             305             310

CAG GGT CAG CAG GCC CAA ACC CCC ACA GGC AAG CAA ACT GAC AAA ACC        1252
Gln Gly Gln Gln Ala Gln Thr Pro Thr Gly Lys Gln Thr Asp Lys Thr
315             320             325             330

AAG AGT AAC ATG AAA GGT TTC TAAGCATGAA TTGAGGAACA GAAGAAGCAG           1303
Lys Ser Asn Met Lys Gly Phe
                335

AGCAGGATGA TCGAGCAGCA TTTGTTTCTC CCAAATCTAG AAATTTAAAG GTTTCTAAGC      1363

ATGAATTGAG GAACAGAAGA AGCAGAGCAG ATGATCGGAG CAGCATTTGT TCTCCCCAA       1423

ATCTAGAAAT TTTAGTTCAT ATGTACACTA GCCAGTGGTT GTGGACAACC ATTTACTTGG      1483

TGTAAAGAAC TTAATTTCAG TATAAACTGA CTCTGGGCAG CAGGTGATGC TGTATCCTGA      1543

GTTGTAGCCT CTGTAATTGT GAATATTAAC TGAGATAGTG AAACATGGTG TCCGGTTTTC      1603

TATTGCATTT TTTCAAGTGG AAAAGTTAAC TAAATGGTTG ACACACAAAA ATTGGTGGAG      1663

AAATTGTGCA TATGCCAATT TTTTGTTAAA ACCTTTTGTT TTGAACTATA CTGCTTTGAG      1723

ATCTCATTTC AGAAGAACGG CATGAACAGT CTTCAGCCAC AGTTGTGATG GTTGTT         1779
```

( 2 ) INFORMATION FOR SEQ ID NO:10:

( i ) SEQUENCE CHARACTERISTICS:
        ( A ) LENGTH: 337 amino acids
        ( B ) TYPE: amino acid
        ( D ) TOPOLOGY: linear ( i i ) MOLECULE TYPE: protein ( x i ) SEQUENCE DESCRIPTION: SEQ ID NO:10:

```
Met Ala Ser Ser Gly Ser Lys Ala Glu Phe Ile Val Gly Gly Lys
1               5               10              15

Tyr Lys Leu Val Arg Lys Ile Gly Ser Gly Ser Phe Gly Asp Ile Tyr
                20              25              30

Leu Ala Ile Asn Ile Thr Asn Gly Glu Glu Val Ala Val Lys Leu Glu
            35              40              45

Ser Gln Lys Ala Arg His Pro Gln Leu Leu Tyr Glu Ser Lys Leu Tyr
        50              55              60

Lys Ile Leu Gln Gly Gly Val Gly Ile Pro His Ile Arg Trp Tyr Gly
65              70              75              80

Gln Glu Lys Asp Tyr Asn Val Leu Val Met Asp Leu Leu Gly Pro Ser
                85              90              95

Leu Glu Asp Leu Phe Asn Phe Cys Ser Arg Arg Phe Thr Met Lys Thr
            100             105             110
```

| | | | | | | | | | | | | | | |
|---|---|---|---|---|---|---|---|---|---|---|---|---|---|---|
|Val|Leu|Met|Leu|Ala|Asp|Gln|Met|Ile|Ser|Arg|Ile|Glu|Tyr|Val|His|
| | |115| | | |120| | | |125| | | | | |

| | | | | | | | | | | | | | |
|---|---|---|---|---|---|---|---|---|---|---|---|---|---|
|Thr|Lys|Asn|Phe|Ile|His|Arg|Asp|Ile|Lys|Pro|Asp|Asn|Phe|Leu|Met|
| |130| | | |135| | | |140| | | | | |

Gly Ile Gly Arg His Cys Asn Lys Leu Phe Leu Ile Asp Phe Gly Leu
145 150 155 160

Ala Lys Lys Tyr Arg Asp Asn Arg Thr Arg Gln His Ile Pro Tyr Arg
165 170 175

Glu Asp Lys Asn Leu Thr Gly Thr Ala Arg Tyr Ala Ser Ile Asn Ala
180 185 190

His Leu Gly Ile Glu Gln Ser Arg Arg Asp Asp Met Glu Ser Leu Gly
195 200 205

Tyr Val Leu Met Tyr Phe Asn Arg Thr Ser Leu Pro Trp Gln Gly Leu
210 215 220

Lys Ala Ala Thr Lys Lys Gln Lys Tyr Glu Lys Ile Ser Glu Lys Lys
225 230 235 240

Met Ser Thr Pro Val Glu Val Leu Cys Lys Gly Phe Pro Ala Glu Phe
245 250 255

Ala Met Tyr Leu Asn Tyr Cys Arg Gly Leu Arg Phe Glu Glu Ala Pro
260 265 270

Asp Tyr Met Tyr Leu Arg Gln Leu Phe Arg Ile Leu Phe Arg Thr Leu
275 280 285

Asn His Gln Tyr Asp Tyr Thr Phe Asp Trp Thr Met Leu Lys Gln Lys
290 295 300

Ala Ala Gln Gln Ala Ala Ser Ser Ser Gly Gln Gly Gln Gln Ala Gln
305 310 315 320

Thr Pro Thr Gly Lys Gln Thr Asp Lys Thr Lys Ser Asn Met Lys Gly
325 330 335

Phe (2) INFORMATION FOR SEQ ID NO:11:

(i) SEQUENCE CHARACTERISTICS:
        (A) LENGTH: 1689 base pairs
        (B) TYPE: nucleic acid
        (C) STRANDEDNESS: single
        (D) TOPOLOGY: linear (ii) MOLECULE TYPE: DNA (genomic)

(vii) IMMEDIATE SOURCE:
        (B) CLONE: Protein Kinase (ix) FEATURE:
        (A) NAME/KEY: CDS
        (B) LOCATION: 294..1385

(xi) SEQUENCE DESCRIPTION: SEQ ID NO:11:

```
GAATTCCGAT AGTATTATGT GGAGTTCCAT TTTTATGTAT TTTTTGTATG AAATATTCTA      60

GTATAAGTAA ATATTTATC  AGAAGTATTT ACATATCTTT TTTTTTTTA  GTTGAGAGC      120

GGCGGTGATC AGGTTCCCCT CTGCTGATTC TGGGCCCCGA ACCCCGGTAA AGGCCTCCGT     180

GTTCCGTTTC CTGCCGCCCT CCTCCGTAGC CTTGCCTAGT GTAGGAGCCC CGAGGCCTCC     240

GTCCTCTTCC CAGAGGTGTC GGGGCTTGGC AGCCTCCATC TTCGTCTCTC AGG ATG        296
                                                            Met
                                                              1

GCG AGT AGC AGC GGC TCC AAG GCT GAA TTC ATT GTC GGA GGG AAA TAT      344
Ala Ser Ser Ser Gly Ser Lys Ala Glu Phe Ile Val Gly Gly Lys Tyr
        5                  10                  15
```

| | | | | | | | | | | | | | | | | |
|---|---|---|---|---|---|---|---|---|---|---|---|---|---|---|---|---|
| AAA | CTG | GTA | CGG | AAG | ATC | GGG | TCT | GGC | TCC | TTC | GGG | GAC | ATC | TAT | TTG | 392 |
| Lys | Leu | Val | Arg | Lys | Ile | Gly | Ser | Gly | Ser | Phe | Gly | Asp | Ile | Tyr | Leu | |
| | | 20 | | | | | 25 | | | | | 30 | | | | |
| GCG | ATC | AAC | ATC | ACC | AAC | GGC | GAG | GAA | GTG | GCA | GTG | AAG | CTA | GAA | TCT | 440 |
| Ala | Ile | Asn | Ile | Thr | Asn | Gly | Glu | Glu | Val | Ala | Val | Lys | Leu | Glu | Ser | |
| | 35 | | | | | 40 | | | | | 45 | | | | | |
| CAG | AAG | GCC | AGG | CAT | CCC | CAG | TTG | CTG | TAC | GAG | AGC | AAG | CTC | TAT | AAG | 488 |
| Gln | Lys | Ala | Arg | His | Pro | Gln | Leu | Leu | Tyr | Glu | Ser | Lys | Leu | Tyr | Lys | |
| 50 | | | | | 55 | | | | | 60 | | | | | 65 | |
| ATT | CTT | CAA | GGT | GGG | GTT | GGC | ATC | CCC | CAC | ATA | CGG | TGG | TAT | GGT | CAG | 536 |
| Ile | Leu | Gln | Gly | Gly | Val | Gly | Ile | Pro | His | Ile | Arg | Trp | Tyr | Gly | Gln | |
| | | | | 70 | | | | | 75 | | | | | 80 | | |
| GAA | AAA | GAC | TAC | AAT | GTA | CTA | GTC | ATG | GAT | CTT | CTG | GGA | CCT | AGC | CTC | 584 |
| Glu | Lys | Asp | Tyr | Asn | Val | Leu | Val | Met | Asp | Leu | Leu | Gly | Pro | Ser | Leu | |
| | | | 85 | | | | | 90 | | | | | 95 | | | |
| GAA | GAC | CTC | TTC | AAT | TTC | TGT | TCA | AGA | AGG | TTC | ACA | ATG | AAA | ACT | GTA | 632 |
| Glu | Asp | Leu | Phe | Asn | Phe | Cys | Ser | Arg | Arg | Phe | Thr | Met | Lys | Thr | Val | |
| | | 100 | | | | | 105 | | | | | 110 | | | | |
| CTT | ATG | TTA | GCT | GAC | CAG | ATG | ATC | AGT | AGA | ATT | GAA | TAT | GTG | CAT | ACA | 680 |
| Leu | Met | Leu | Ala | Asp | Gln | Met | Ile | Ser | Arg | Ile | Glu | Tyr | Val | His | Thr | |
| | 115 | | | | | 120 | | | | | 125 | | | | | |
| AAG | AAT | TTT | ATA | CAC | AGA | GAC | ATT | AAA | CCA | GAT | AAC | TTC | CTA | ATG | GGT | 728 |
| Lys | Asn | Phe | Ile | His | Arg | Asp | Ile | Lys | Pro | Asp | Asn | Phe | Leu | Met | Gly | |
| 130 | | | | | 135 | | | | | 140 | | | | | 145 | |
| ATT | GGG | CGT | CAC | TGT | AAT | AAG | TGT | TTA | GAA | TCT | CCA | GTG | GGG | AAG | AGG | 776 |
| Ile | Gly | Arg | His | Cys | Asn | Lys | Cys | Leu | Glu | Ser | Pro | Val | Gly | Lys | Arg | |
| | | | | 150 | | | | | 155 | | | | | 160 | | |
| AAA | AGA | AGC | ATG | ACT | GTT | AGT | ACT | TCT | CAG | GAC | CCA | TCT | TTC | TCA | GGA | 824 |
| Lys | Arg | Ser | Met | Thr | Val | Ser | Thr | Ser | Gln | Asp | Pro | Ser | Phe | Ser | Gly | |
| | | | 165 | | | | | 170 | | | | | 175 | | | |
| TTA | AAC | CAG | TTA | TTC | CTT | ATT | GAT | TTT | GGT | TTG | GCC | AAA | AAG | TAC | AGA | 872 |
| Leu | Asn | Gln | Leu | Phe | Leu | Ile | Asp | Phe | Gly | Leu | Ala | Lys | Lys | Tyr | Arg | |
| | | 180 | | | | | 185 | | | | | 190 | | | | |
| GAC | AAC | AGG | ACA | AGG | CAA | CAC | ATA | CCA | TAC | AGA | GAA | GAT | AAA | AAC | CTC | 920 |
| Asp | Asn | Arg | Thr | Arg | Gln | His | Ile | Pro | Tyr | Arg | Glu | Asp | Lys | Asn | Leu | |
| | 195 | | | | | 200 | | | | | 205 | | | | | |
| ACT | GGC | ACT | GCC | CGA | TAT | GCT | AGC | ATC | AAT | GCA | CAT | CTT | GGT | ATT | GAG | 968 |
| Thr | Gly | Thr | Ala | Arg | Tyr | Ala | Ser | Ile | Asn | Ala | His | Leu | Gly | Ile | Glu | |
| 210 | | | | | 215 | | | | | 220 | | | | | 225 | |
| CAG | AGT | CGC | CGA | GAT | GAC | ATG | GAA | TCA | TTA | GGA | TAT | GTT | TTG | ATG | TAT | 1016 |
| Gln | Ser | Arg | Arg | Asp | Asp | Met | Glu | Ser | Leu | Gly | Tyr | Val | Leu | Met | Tyr | |
| | | | | 230 | | | | | 235 | | | | | 240 | | |
| TTT | AAT | AGA | ACC | AGC | CTG | CCA | TGG | CAA | GGG | CTA | AAG | GCT | GCA | ACA | AAG | 1064 |
| Phe | Asn | Arg | Thr | Ser | Leu | Pro | Trp | Gln | Gly | Leu | Lys | Ala | Ala | Thr | Lys | |
| | | | 245 | | | | | 250 | | | | | 255 | | | |
| AAA | CAA | AAA | TAT | GAA | AAG | ATT | AGT | GAA | AAG | AAG | ATG | TCC | ACG | CCT | GTT | 1112 |
| Lys | Gln | Lys | Tyr | Glu | Lys | Ile | Ser | Glu | Lys | Lys | Met | Ser | Thr | Pro | Val | |
| | | 260 | | | | | 265 | | | | | 270 | | | | |
| GAA | GTT | TTA | TGT | AAG | GGG | TTT | CCT | GCA | GAA | TTT | GCG | ATG | TAC | TTA | AAC | 1160 |
| Glu | Val | Leu | Cys | Lys | Gly | Phe | Pro | Ala | Glu | Phe | Ala | Met | Tyr | Leu | Asn | |
| | 275 | | | | | 280 | | | | | 285 | | | | | |
| TAT | TGT | CGT | GGG | CTA | CGC | TTT | GAG | GAA | GCC | CCA | GAT | TAC | ATG | TAT | CTG | 1208 |
| Tyr | Cys | Arg | Gly | Leu | Arg | Phe | Glu | Glu | Ala | Pro | Asp | Tyr | Met | Tyr | Leu | |
| 290 | | | | | 295 | | | | | 300 | | | | | 305 | |
| AGG | CAG | CTA | TTC | CGC | ATT | CTT | TTC | AGG | ACC | CTG | AAC | CAT | CAA | TAT | GAC | 1256 |
| Arg | Gln | Leu | Phe | Arg | Ile | Leu | Phe | Arg | Thr | Leu | Asn | His | Gln | Tyr | Asp | |
| | | | | 310 | | | | | 315 | | | | | 320 | | |
| TAC | ACA | TTT | GAT | TGG | ACA | ATG | TTA | AAG | CAG | AAA | GCA | GCA | CAG | CAG | GCA | 1304 |
| Tyr | Thr | Phe | Asp | Trp | Thr | Met | Leu | Lys | Gln | Lys | Ala | Ala | Gln | Gln | Ala | |
| | | | 325 | | | | | 330 | | | | | 335 | | | |

| GCC | TCT | TCC | AGT | GGG | CAG | GGT | CAG | CAG | GCC | CAA | ACC | CCC | ACA | GGC | AAG | 1352 |
| Ala | Ser | Ser | Ser | Gly | Gln | Gly | Gln | Gln | Ala | Gln | Thr | Pro | Thr | Gly | Lys | |
| | | | 340 | | | | | 345 | | | | | 350 | | | |

| CAA | ACT | GAC | AAA | ACC | AAG | AGT | AAC | ATG | AAA | GGT | TAGTAGCCAA | GAACCAAGTG | 1405 |
| Gln | Thr | Asp | Lys | Thr | Lys | Ser | Asn | Met | Lys | Gly | | | |
| | 355 | | | | | 360 | | | | | | | |

| ACGTTACAGG | GAAAAAATTG | AATACAAAAT | TGGGTAATTC | ATTTCTAACA | GTGTTAGATC | 1465 |
| AAGGAGGTGG | TTTTAAAATA | CATAAAAATT | TGGCTCTGCG | TTAAAAAAAA | AAAAGACGTC | 1525 |
| CTTGGAAAAT | TTGACTACTA | ACTTTAAACC | CAAATGTCCT | TGTTCATATA | TATGTATATG | 1585 |
| TATTTGTATA | TACATATATG | TGTGTATATT | TATATCATTT | CTCTTGGGAT | TTGGGTCAT | 1645 |
| TTTTTTAACA | ACTGCATCTT | TTTTACTCAT | TCATTAACCC | CCTT | | 1689 |

( 2 ) INFORMATION FOR SEQ ID NO:12:

( i ) SEQUENCE CHARACTERISTICS:
        ( A ) LENGTH: 364 amino acids
        ( B ) TYPE: amino acid
        ( D ) TOPOLOGY: linear ( i i ) MOLECULE TYPE: protein ( x i ) SEQUENCE DESCRIPTION: SEQ ID NO:12:

| Met | Ala | Ser | Ser | Ser | Gly | Ser | Lys | Ala | Glu | Phe | Ile | Val | Gly | Gly | Lys |
| 1 | | | | 5 | | | | | 10 | | | | | 15 | |
| Tyr | Lys | Leu | Val | Arg | Lys | Ile | Gly | Ser | Gly | Ser | Phe | Gly | Asp | Ile | Tyr |
| | | | 20 | | | | | 25 | | | | | 30 | | |
| Leu | Ala | Ile | Asn | Ile | Thr | Asn | Gly | Glu | Glu | Val | Ala | Val | Lys | Leu | Glu |
| | | | 35 | | | | | 40 | | | | | 45 | | |
| Ser | Gln | Lys | Ala | Arg | His | Pro | Gln | Leu | Leu | Tyr | Glu | Ser | Lys | Leu | Tyr |
| | 50 | | | | | 55 | | | | | 60 | | | | |
| Lys | Ile | Leu | Gln | Gly | Gly | Val | Gly | Ile | Pro | His | Ile | Arg | Trp | Tyr | Gly |
| 65 | | | | | 70 | | | | | 75 | | | | | 80 |
| Gln | Glu | Lys | Asp | Tyr | Asn | Val | Leu | Val | Met | Asp | Leu | Leu | Gly | Pro | Ser |
| | | | | 85 | | | | | 90 | | | | | 95 | |
| Leu | Glu | Asp | Leu | Phe | Asn | Phe | Cys | Ser | Arg | Arg | Phe | Thr | Met | Lys | Thr |
| | | | 100 | | | | | 105 | | | | | 110 | | |
| Val | Leu | Met | Leu | Ala | Asp | Gln | Met | Ile | Ser | Arg | Ile | Glu | Tyr | Val | His |
| | | | 115 | | | | | 120 | | | | | 125 | | |
| Thr | Lys | Asn | Phe | Ile | His | Arg | Asp | Ile | Lys | Pro | Asp | Asn | Phe | Leu | Met |
| | | 130 | | | | | 135 | | | | | 140 | | | |
| Gly | Ile | Gly | Arg | His | Cys | Asn | Lys | Cys | Leu | Glu | Ser | Pro | Val | Gly | Lys |
| 145 | | | | | 150 | | | | | 155 | | | | | 160 |
| Arg | Lys | Arg | Ser | Met | Thr | Val | Ser | Thr | Ser | Gln | Asp | Pro | Ser | Phe | Ser |
| | | | | 165 | | | | | 170 | | | | | 175 | |
| Gly | Leu | Asn | Gln | Leu | Phe | Leu | Ile | Asp | Phe | Gly | Leu | Ala | Lys | Lys | Tyr |
| | | | 180 | | | | | 185 | | | | | 190 | | |
| Arg | Asp | Asn | Arg | Thr | Arg | Gln | His | Ile | Pro | Tyr | Arg | Glu | Asp | Lys | Asn |
| | | | 195 | | | | | 200 | | | | | 205 | | |
| Leu | Thr | Gly | Thr | Ala | Arg | Tyr | Ala | Ser | Ile | Asn | Ala | His | Leu | Gly | Ile |
| | | 210 | | | | | 215 | | | | | 220 | | | |
| Glu | Gln | Ser | Arg | Arg | Asp | Asp | Met | Glu | Ser | Leu | Gly | Tyr | Val | Leu | Met |
| 225 | | | | | 230 | | | | | 235 | | | | | 240 |
| Tyr | Phe | Asn | Arg | Thr | Ser | Leu | Pro | Trp | Gln | Gly | Leu | Lys | Ala | Ala | Thr |
| | | | | 245 | | | | | 250 | | | | | 255 | |
| Lys | Lys | Gln | Lys | Tyr | Glu | Lys | Ile | Ser | Glu | Lys | Lys | Met | Ser | Thr | Pro |
| | | | 260 | | | | | 265 | | | | | 270 | | |

| | | | | | | | | | | | | | | |
|---|---|---|---|---|---|---|---|---|---|---|---|---|---|---|
|Val|Glu|Val|Leu|Cys|Lys|Gly|Phe|Pro|Ala|Glu|Phe|Ala|Met|Tyr|Leu|
| | |275| | | | |280| | | | |285| | | |

| | | | | | | | | | | | | | | |
|---|---|---|---|---|---|---|---|---|---|---|---|---|---|---|
|Asn|Tyr|Cys|Arg|Gly|Leu|Arg|Phe|Glu|Glu|Ala|Pro|Asp|Tyr|Met|Tyr|
| |290| | | | |295| | | | |300| | | | |

| | | | | | | | | | | | | | | |
|---|---|---|---|---|---|---|---|---|---|---|---|---|---|---|
|Leu|Arg|Gln|Leu|Phe|Arg|Ile|Leu|Phe|Arg|Thr|Leu|Asn|His|Gln|Tyr|
|305| | | | |310| | | | |315| | | | |320|

| | | | | | | | | | | | | | | |
|---|---|---|---|---|---|---|---|---|---|---|---|---|---|---|
|Asp|Tyr|Thr|Phe|Asp|Trp|Thr|Met|Leu|Lys|Gln|Lys|Ala|Ala|Gln|Gln|
| | | | |325| | | | |330| | | | |335| |

| | | | | | | | | | | | | | | |
|---|---|---|---|---|---|---|---|---|---|---|---|---|---|---|
|Ala|Ala|Ser|Ser|Ser|Gly|Gln|Gly|Gln|Gln|Ala|Gln|Thr|Pro|Thr|Gly|
| | | |340| | | | |345| | | | |350| | |

| | | | | | | | | | | |
|---|---|---|---|---|---|---|---|---|---|---|
|Lys|Gln|Thr|Asp|Lys|Thr|Lys|Ser|Asn|Met|Lys|Gly|
| | |355| | | | |360| | | | |

(2) INFORMATION FOR SEQ ID NO:13:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(vii) IMMEDIATE SOURCE:
        (B) CLONE: Protein Kinase (ix) FEATURE:
        (A) NAME/KEY: CDS
        (B) LOCATION: 1..23
        (D) OTHER INFORMATION: /note= "Bases designated N at
            positions 3, 6, 9, 12 and 18 are Inosine."

(xi) SEQUENCE DESCRIPTION: SEQ ID NO:13:

GGNWSNGGNW SNTT Y GGNGA Y AT    23

(2) INFORMATION FOR SEQ ID NO:14:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(vii) IMMEDIATE SOURCE:
        (B) CLONE: Protein Kinase (ix) FEATURE:
        (A) NAME/KEY: CDS
        (B) LOCATION: 1..23
        (D) OTHER INFORMATION: /note= "Bases designated N at
            positions 6, 12 and 18 are Inosine."

(xi) SEQUENCE DESCRIPTION: SEQ ID NO:14:

CA Y GMNGA Y A TNAARCCN-
GA Y AA    23

(2) INFORMATION FOR SEQ ID NO:15:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(vii) IMMEDIATE SOURCE:

-continued (B) CLONE: Protein Kinase (ix) FEATURE:
      (A) NAME/KEY: CDS
      (B) LOCATION: 1..24
      (D) OTHER INFORMATION: /note= "Bases designated N at
            positions 7, 13 and 19 are Inosine."

(xi) SEQUENCE DESCRIPTION: SEQ ID NO:15:

RTTRTCNGG Y TTNATRTCNC KRTG 24

(2) INFORMATION FOR SEQ ID NO:16:

(i) SEQUENCE CHARACTERISTICS:
      (A) LENGTH: 18 base pairs
      (B) TYPE: nucleic acid
      (C) STRANDEDNESS: single
      (D) TOPOLOGY: linear (ii) MOLECULE TYPE: DNA (genomic)

(vii) IMMEDIATE SOURCE:
      (B) CLONE: Protein Kinase (ix) FEATURE:
      (A) NAME/KEY: CDS
      (B) LOCATION: 1..18
      (D) OTHER INFORMATION: /note= "Bases designated N at
            positions 1, 4, 7 and 13 are Inosine."

(xi) SEQUENCE DESCRIPTION: SEQ ID NO:16:

NCCNARNSW Y TCNARRTC 18

(2) INFORMATION FOR SEQ ID NO:17:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: DNA (genomic)

(vii) IMMEDIATE SOURCE:
      (B) CLONE: Protein Kinase (ix) FEATURE:
      (A) NAME/KEY: CDS
      (B) LOCATION: 1..20

(xi) SEQUENCE DESCRIPTION: SEQ ID NO:17:

ATATAAACTG GTACGGAAGA 20

(2) INFORMATION FOR SEQ ID NO:18:

(i) SEQUENCE CHARACTERISTICS:
      (A) LENGTH: 17 base pairs
      (B) TYPE: nucleic acid
      (C) STRANDEDNESS: single
      (D) TOPOLOGY: linear (ii) MOLECULE TYPE: DNA (genomic)

(vii) IMMEDIATE SOURCE:
      (B) CLONE: Protein Kinase (ix) FEATURE:
      (A) NAME/KEY: CDS
      (B) LOCATION: 1..17

(xi) SEQUENCE DESCRIPTION: SEQ ID NO:18:

ACATACGGTG GTATGGT 17

( 2 ) INFORMATION FOR SEQ ID NO:19:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( v i i ) IMMEDIATE SOURCE:
        ( B ) CLONE: Protein Kinase ( i x ) FEATURE:
        ( A ) NAME/KEY: CDS
        ( B ) LOCATION: 1..19

( x i ) SEQUENCE DESCRIPTION: SEQ ID NO:19:

ATGACATGGA ATCATTAGG                                        19

( 2 ) INFORMATION FOR SEQ ID NO:20:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( v i i ) IMMEDIATE SOURCE:
        ( B ) CLONE: Protein Kinase ( i x ) FEATURE:
        ( A ) NAME/KEY: CDS
        ( B ) LOCATION: 1..19

( x i ) SEQUENCE DESCRIPTION: SEQ ID NO:20:

CCTAATGATT CCATGTCAT                                        19

( 2 ) INFORMATION FOR SEQ ID NO:21:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( v i i ) IMMEDIATE SOURCE:
        ( B ) CLONE: Protein Kinase ( i x ) FEATURE:
        ( A ) NAME/KEY: CDS
        ( B ) LOCATION: 1..18

( x i ) SEQUENCE DESCRIPTION: SEQ ID NO:21:

TCAGGTACAT GTAATCCG                                          18

( 2 ) INFORMATION FOR SEQ ID NO:22:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: DNA (genomic)

( v i i ) IMMEDIATE SOURCE:
        ( B ) CLONE: Protein Kinase ( i x ) FEATURE:
    ( A ) NAME/KEY: CDS
    ( B ) LOCATION: 1..39

( x i ) SEQUENCE DESCRIPTION: SEQ ID NO:22:

| | | | | |
|---|---|---|---|---|
| CCTGATCGAT | TCCAGCCTGA | TCGCTACTTC | TTCACCACT | 39 |

( 2 ) INFORMATION FOR SEQ ID NO:23:

( i ) SEQUENCE CHARACTERISTICS:
    ( A ) LENGTH: 3627 base pairs
    ( B ) TYPE: nucleic acid
    ( C ) STRANDEDNESS: single
    ( D ) TOPOLOGY: linear ( i i ) MOLECULE TYPE: DNA (genomic)

( v i i ) IMMEDIATE SOURCE:
    ( B ) CLONE: Protein Kinase ( i x ) FEATURE:
    ( A ) NAME/KEY: CDS
    ( B ) LOCATION: 1633..3204

( x i ) SEQUENCE DESCRIPTION: SEQ ID NO:23:

| | | | | | |
|---|---|---|---|---|---|
| GATCAGATGA | TATAGCTTTT | TGTGTGCCGT | ACCTTTCCGC | GATTCTGCCC | GTATATCTTG | 60 |
| GTCCCTGAGC | TATTTTCTGA | GATTCTTTTT | GTTGCTTTGC | CAAATCATTG | GCGTCATTCA | 120 |
| TGGTCATACC | AAATCCCAAT | TTGGCAAACT | GGGTGTTAAA | AGTATCTTGC | TGTTCTTTTC | 180 |
| TAGTTGTGTC | GAAGCTGTTT | GAAGTGTCAT | TTAAAAAATC | ATTGAATTCA | TCAGGCTGGG | 240 |
| TATTAATATC | ATCTATACTG | TTATTATTGT | TGCCTTTACT | GTTATTCATA | AATTGGGAAT | 300 |
| CGTAATCATT | TGTCTAATTT | TGGTGCTAGA | AGACGAATTA | GTGAACTCGT | CCTCCTTTTC | 360 |
| TTGTTGAGCC | TCTTTTTTAA | ATTGATCAAA | CAAGTCTTCT | GCCTGTGATT | TGTCGACTTT | 420 |
| CTTTGCGGTT | AGTCTAGTGG | GCTTTCTTGA | CGAAGACAAA | ATTGAATGTT | CTTTTTATC | 480 |
| TTGCGAGTTT | AATACCGGTT | TCTTTCTGCA | TGCCGTTAAG | ATGGAACTCT | CGTTTAGTG | 540 |
| ACAGTGGTCT | TGGGTGTGCT | GCCTGTGGTG | TTGTTTTTTG | GGGCGAGAGA | GCCTGTATTT | 600 |
| ACATTGAGTT | TAGAACTGGA | ATTGGAGCTT | GGTTTTGCC | AATTAGAGAA | AAAATCGTCA | 660 |
| ACACTATTTT | CTTTGGAAGT | CGACCTGGAA | GCGTCTGAAT | CGGTGTCCAA | CGGTGAGTCC | 720 |
| GAAGAATCTT | GACCGTTCAA | GACTAATTCT | GATGGGTATA | ACTCCATATC | CTTTTGAACC | 780 |
| TTCTTGTCGA | GATGTATCTT | ATATTTCTTA | GCAACAGGGC | TCGTATATTT | TGTTTTCGCG | 840 |
| TCAACATTTG | CTGTATTTAG | TAGCTGTTTC | CCATTGTTCT | TTAAGAAAAA | ATCACGAGCC | 900 |
| TTATGGTTCC | CACCCAACTT | AAACCTTCTT | AAATTGTTAA | TTGTCCATTT | ATCTAATGTA | 960 |
| GAAGACTTTA | CAAAGGTGAT | ATGAACACCC | ATGTTTCTAT | GCACAGCAGA | GCATTGAATA | 1020 |
| CACAGCATCA | CACCAAAAGG | TACCGAAGTC | CAGTAGGATT | CTTGTTACCA | CAATCAAAAC | 1080 |
| AAACTCGATT | TTCCATGTTG | CTACCTAGCT | TCTGAAAAAC | TTGTTGAGTA | GTCTGTTCCG | 1140 |
| TGGCAAATGT | TTCTCCTTCA | TCGTTACTCA | TTGTCGCTAT | GTGTATACTA | AATTGCTCAA | 1200 |
| GAAGACCGGA | TCAACAAGTA | CTTAACAAAT | ACCCTTTCTT | TGCTATCGCC | TTGATCTCCT | 1260 |
| TTTATAAAAT | GCCAGCTAAA | TCGTGTTTAC | GAAGAATAGT | TGTTTTCTTT | TTTTTTTTT | 1320 |
| TTTTTCGAAA | CTTTACCGTG | TCGTCGAAAA | TGACCAAACG | ATGTTACTTT | TCCTTTTGTG | 1380 |
| TCATAGATAA | TACCAATATT | GAAAGTAAAA | TTTAAACAT | TCTATAGGTG | AATTGAAAAG | 1440 |
| GGCAGCTTAG | AGAGTAACAG | GGGAACAGCA | TTCGTAACAT | CTAGGTACTG | GTATTATTTG | 1500 |
| CTGTTTTTTA | AAAAGAAGG | AAATCCGTTT | TGCAAGAATT | GTCTGCTATT | TAAGGGTATA | 1560 |

| | |
|---|---|
| CGTGCTACGG TCCACTAATC AAAAGTGGTA TCTCATTCTG AAGAAAAAGT GTAAAAGGA | 1620 |

```
CGATAAGGAA AG ATG TCC CAA CGA TCT TCA CAA CAC ATT GTA GGT ATT      1668
              Met Ser Gln Arg Ser Ser Gln His Ile Val Gly Ile
               1               5                  10

CAT TAT GCT GTA GGA CCT AAG ATT GGC GAA GGG TCT TTC GGA GTA ATA    1716
His Tyr Ala Val Gly Pro Lys Ile Gly Glu Gly Ser Phe Gly Val Ile
            15              20              25

TTT GAG GGA GAG AAC ATT CTT CAT TCT TGT CAA GCG CAG ACC GGT AGC    1764
Phe Glu Gly Glu Asn Ile Leu His Ser Cys Gln Ala Gln Thr Gly Ser
     30              35              40

AAG AGG GAC TCT AGT ATA ATA ATG GCG AAC GAG CCA GTC GCA ATT AAA    1812
Lys Arg Asp Ser Ser Ile Ile Met Ala Asn Glu Pro Val Ala Ile Lys
 45              50              55                          60

TTC GAA CCG CGA CAT TCG GAC GCA CCC CAG TTG CGT GAC GAA TTT AGA    1860
Phe Glu Pro Arg His Ser Asp Ala Pro Gln Leu Arg Asp Glu Phe Arg
                 65              70              75

GCC TAT AGG ATA TTG AAT GGC TGC GTT GGA ATT CCC CAT GCT TAT TAT    1908
Ala Tyr Arg Ile Leu Asn Gly Cys Val Gly Ile Pro His Ala Tyr Tyr
             80              85              90

TTT GGT CAA GAA GGT ATG CAC AAC ATC TTG ATT ATC GAT TTA CTA GGG    1956
Phe Gly Gln Glu Gly Met His Asn Ile Leu Ile Ile Asp Leu Leu Gly
         95              100             105

CCA TCA TTG GAA GAT CTC TTT GAG TGG TGT GGT AGA AAA TTT TCA GTG    2004
Pro Ser Leu Glu Asp Leu Phe Glu Trp Cys Gly Arg Lys Phe Ser Val
 110             115             120

AAA ACA ACC TGT ATG GTT GCC AAG CAA ATG ATT GAT AGA GTT AGA GCA    2052
Lys Thr Thr Cys Met Val Ala Lys Gln Met Ile Asp Arg Val Arg Ala
125             130             135             140

ATT CAT GAT CAC GAC TTA ATC TAT CGC GAT ATT AAA CCC GAT AAC TTT    2100
Ile His Asp His Asp Leu Ile Tyr Arg Asp Ile Lys Pro Asp Asn Phe
             145             150             155

TTA ATT TCT CAA TAT CAA AGA ATT TCA CCT GAA GGA AAA GTC ATT AAA    2148
Leu Ile Ser Gln Tyr Gln Arg Ile Ser Pro Glu Gly Lys Val Ile Lys
         160             165             170

TCA TGT GCC TCC TCT TCT AAT AAT GAT CCC AAT TTA ATA TAC ATG GTT    2196
Ser Cys Ala Ser Ser Ser Asn Asn Asp Pro Asn Leu Ile Tyr Met Val
     175             180             185

GAC TTT GGT ATG GCA AAA CAA TAT AGA GAT CCA AGA ACG AAA CAA CAT    2244
Asp Phe Gly Met Ala Lys Gln Tyr Arg Asp Pro Arg Thr Lys Gln His
 190             195                             200

ATA CCA TAC CGT GAA CGA AAA TCA TTG AGC GGT ACC GCC AGA TAT ATG    2292
Ile Pro Tyr Arg Glu Arg Lys Ser Leu Ser Gly Thr Ala Arg Tyr Met
205             210             215             220

TCT ATT AAT ACT CAT TTT GGA AGA GAA CAG TCA CGT AGG GAT GAT TTA    2340
Ser Ile Asn Thr His Phe Gly Arg Glu Gln Ser Arg Arg Asp Asp Leu
             225             230             235

GAA TCG CTA GGT CAC GTT TTT TTT TAT TTC TTG AGG GGA TCC TTG CCA    2388
Glu Ser Leu Gly His Val Phe Phe Tyr Phe Leu Arg Gly Ser Leu Pro
         240             245             250

TGG CAA GGT TTG AAA GCA CCA AAC AAC AAA CTG AAG TAT GAA AAG ATT    2436
Trp Gln Gly Leu Lys Ala Pro Asn Asn Lys Leu Lys Tyr Glu Lys Ile
     255             260             265

GGT ATG ACT AAA CAG AAA TTG AAT CCT GAT GAT CTT TTA TTG AAT AAT    2484
Gly Met Thr Lys Gln Lys Leu Asn Pro Asp Asp Leu Leu Leu Asn Asn
 270             275             280

GCT ATT CCT TAT CAG TTT GCC ACA TAT TTA AAA TAT GCA CGT TCC TTG    2532
Ala Ile Pro Tyr Gln Phe Ala Thr Tyr Leu Lys Tyr Ala Arg Ser Leu
285             290             295             300

AAG TTC GAC GAA GAT CCG GAT TAT GAC TAT TTA ATC TCG TTA ATG GAT    2580
Lys Phe Asp Glu Asp Pro Asp Tyr Asp Tyr Leu Ile Ser Leu Met Asp
```

|  |  |  |  |  |  |  |  |  |  |  |  |  |  |  |  |
|---|---|---|---|---|---|---|---|---|---|---|---|---|---|---|---|
|  |  |  |  |  | 305 |  |  |  |  | 310 |  |  |  |  | 315 |
| GAC | GCT | TTG | AGA | TTA | AAC | GAC | TTA | AAG | GAT | GAT | GGA | CAC | TAT | GAC | TGG | 2628
| Asp | Ala | Leu | Arg | Leu | Asn | Asp | Leu | Lys | Asp | Asp | Gly | His | Tyr | Asp | Trp |
|  |  |  | 320 |  |  |  |  | 325 |  |  |  |  | 330 |  |  |
| ATG | GAT | TTG | AAT | GGT | GGT | AAA | GGC | TGG | AAT | ATC | AAG | ATT | AAT | AGA | AGA | 2676
| Met | Asp | Leu | Asn | Gly | Gly | Lys | Gly | Trp | Asn | Ile | Lys | Ile | Asn | Arg | Arg |
|  |  |  | 335 |  |  |  | 340 |  |  |  |  | 345 |  |  |  |
| GCT | AAC | TTG | CAT | GGT | TAC | GGA | AAT | CCA | AAT | CCA | AGA | GTC | AAT | GGC | AAT | 2724
| Ala | Asn | Leu | His | Gly | Tyr | Gly | Asn | Pro | Asn | Pro | Arg | Val | Asn | Gly | Asn |
|  |  | 350 |  |  |  | 355 |  |  |  |  | 360 |  |  |  |  |
| ACT | GCA | AGA | AAC | AAT | GTG | AAT | ACG | AAT | TCA | AAG | ACA | CGA | AAT | ACA | ACG | 2772
| Thr | Ala | Arg | Asn | Asn | Val | Asn | Thr | Asn | Ser | Lys | Thr | Arg | Asn | Thr | Thr |
| 365 |  |  |  |  | 370 |  |  |  |  | 375 |  |  |  |  | 380 |
| CCA | GTT | GCG | ACA | CCT | AAG | CAA | CAA | GCT | CAA | AAC | AGT | TAT | AAC | AAG | GAC | 2820
| Pro | Val | Ala | Thr | Pro | Lys | Gln | Gln | Ala | Gln | Asn | Ser | Tyr | Asn | Lys | Asp |
|  |  |  |  | 385 |  |  |  |  | 390 |  |  |  |  | 395 |  |
| AAT | TCG | AAA | TCC | AGA | ATT | TCT | TCG | AAC | CCG | CAG | AGC | TTT | ACT | AAA | CAA | 2868
| Asn | Ser | Lys | Ser | Arg | Ile | Ser | Ser | Asn | Pro | Gln | Ser | Phe | Thr | Lys | Gln |
|  |  |  | 400 |  |  |  |  | 405 |  |  |  |  | 410 |  |  |
| CAA | CAC | GTC | TTG | AAA | AAA | ATC | GAA | CCC | AAT | AGT | AAA | TAT | ATT | CCT | GAA | 2916
| Gln | His | Val | Leu | Lys | Lys | Ile | Glu | Pro | Asn | Ser | Lys | Tyr | Ile | Pro | Glu |
|  |  | 415 |  |  |  |  | 420 |  |  |  |  | 425 |  |  |  |
| ACA | CAT | TCA | AAT | CTT | CAA | CGG | CCA | ATT | AAA | AGT | CAA | AGT | CAA | ACG | TAC | 2964
| Thr | His | Ser | Asn | Leu | Gln | Arg | Pro | Ile | Lys | Ser | Gln | Ser | Gln | Thr | Tyr |
| 430 |  |  |  |  |  | 435 |  |  |  |  | 440 |  |  |  |  |
| GAC | TCC | ATC | AGT | CAT | ACA | CAA | AAT | TCA | CCA | TTT | GTA | CCA | TAT | TCA | AGT | 3012
| Asp | Ser | Ile | Ser | His | Thr | Gln | Asn | Ser | Pro | Phe | Val | Pro | Tyr | Ser | Ser |
| 445 |  |  |  |  | 450 |  |  |  |  | 455 |  |  |  |  | 460 |
| TCT | AAA | GCT | AAC | CCT | AAA | AGA | AGT | AAT | AAT | GAG | CAC | AAC | TTA | CCA | AAC | 3060
| Ser | Lys | Ala | Asn | Pro | Lys | Arg | Ser | Asn | Asn | Glu | His | Asn | Leu | Pro | Asn |
|  |  |  |  | 465 |  |  |  |  | 470 |  |  |  |  | 475 |  |
| CAC | TAC | ACA | AAC | CTT | GCA | AAT | AAG | AAT | ATC | AAT | TAT | CAA | AGT | CAA | CGA | 3108
| His | Tyr | Thr | Asn | Leu | Ala | Asn | Lys | Asn | Ile | Asn | Tyr | Gln | Ser | Gln | Arg |
|  |  |  | 480 |  |  |  |  | 485 |  |  |  |  | 490 |  |  |
| AAT | TAC | GAA | CAA | GAA | AAT | GAT | GCT | TAT | TCT | GAT | GAC | GAG | AAT | GAT | ACA | 3156
| Asn | Tyr | Glu | Gln | Glu | Asn | Asp | Ala | Tyr | Ser | Asp | Asp | Glu | Asn | Asp | Thr |
|  |  | 495 |  |  |  |  | 500 |  |  |  |  | 505 |  |  |  |
| TTT | TGT | TCT | AAA | ATA | TAC | AAA | TAT | TGT | TGT | TGC | TGT | TTT | TGT | TGC | TGT | 3204
| Phe | Cys | Ser | Lys | Ile | Tyr | Lys | Tyr | Cys | Cys | Cys | Cys | Phe | Cys | Cys | Cys |
|  | 510 |  |  |  |  | 515 |  |  |  |  | 520 |  |  |  |  |

| | | | | |
|---|---|---|---|---|
| TGATAAAGCG | ATTTTTATAC | TTTTCTCTTT | TTCCTTTTTT | TTTTGATTG GCTGTTTCCT | 3264
| TATGCCGCTC | TTTCCCAATT | TATGACTTTC | CAATAATGTA | TTATTTTGTT TCTCTTTCTC | 3324
| TCTGTTACCC | TTTATTTTAT | CATCTACAAT | AATTGAATTC | CGGAGAGGGT AAAGAAACAG | 3384
| GAAAAGAAG | AAAATGAGAC | ATAGTCAGCA | TCGTAATCGT | TTTCCTTCTG TATATTCCTT | 3444
| TATCAAAAGA | CTACACGCAC | ATATATATTA | ATCCGGTAT | GTTTTGGTG TGCTAAATCT | 3504
| ATCTTCAAGC | ACTATTATAG | CATTTTTTA | AGAATATCCA | AAATAATATG TAATTTATGA | 3564
| TTAATCAAGG | TTCAAGAATT | GGAGAAACCG | TGAGCGACTT | CTTTGATACT TGGATGTAAG | 3624
| CTT | | | | | 3627

( 2 ) INFORMATION FOR SEQ ID NO:24:

( i ) SEQUENCE CHARACTERISTICS:
        ( A ) LENGTH: 524 amino acids
        ( B ) TYPE: amino acid
        ( D ) TOPOLOGY: linear ( i i ) MOLECULE TYPE: protein ( x i ) SEQUENCE DESCRIPTION: SEQ ID NO:24:

| | | | | | | | | | | | | | | |
|---|---|---|---|---|---|---|---|---|---|---|---|---|---|---|
| Met 1 | Ser | Gln | Arg | Ser 5 | Ser | Gln | His | Ile | Val 10 | Gly | Ile | His | Tyr | Ala Val 15 |
| Gly | Pro | Lys | Ile 20 | Gly | Glu | Gly | Ser | Phe 25 | Gly | Val | Ile | Phe | Glu 30 | Gly Glu |
| Asn | Ile | Leu 35 | His | Ser | Cys | Gln | Ala 40 | Gln | Thr | Gly | Ser | Lys 45 | Arg | Asp Ser |
| Ser | Ile 50 | Ile | Met | Ala | Asn 55 | Glu | Pro | Val | Ala | Ile 60 | Lys | Phe | Glu | Pro Arg |
| His 65 | Ser | Asp | Ala | Pro | Gln 70 | Leu | Arg | Asp | Glu | Phe 75 | Arg | Ala | Tyr | Arg Ile 80 |
| Leu | Asn | Gly | Cys | Val 85 | Gly | Ile | Pro | His | Ala 90 | Tyr | Tyr | Phe | Gly | Gln Glu 95 |
| Gly | Met | His | Asn 100 | Ile | Leu | Ile | Ile | Asp 105 | Leu | Leu | Gly | Pro | Ser 110 | Leu Glu |
| Asp | Leu | Phe 115 | Glu | Trp | Cys | Gly | Arg 120 | Lys | Phe | Ser | Val | Lys 125 | Thr | Thr Cys |
| Met | Val 130 | Ala | Lys | Gln | Met | Ile 135 | Asp | Arg | Val | Arg | Ala 140 | Ile | His | Asp His |
| Asp 145 | Leu | Ile | Tyr | Arg | Asp 150 | Ile | Lys | Pro | Asp | Asn 155 | Phe | Leu | Ile | Ser Gln 160 |
| Tyr | Gln | Arg | Ile | Ser 165 | Pro | Glu | Gly | Lys | Val 170 | Ile | Lys | Ser | Cys | Ala Ser 175 |
| Ser | Ser | Asn | Asn 180 | Asp | Pro | Asn | Leu | Ile 185 | Tyr | Met | Val | Asp | Phe 190 | Gly Met |
| Ala | Lys | Gln 195 | Tyr | Arg | Asp | Pro | Arg 200 | Thr | Lys | Gln | His | Ile 205 | Pro | Tyr Arg |
| Glu | Arg 210 | Lys | Ser | Leu | Ser | Gly 215 | Thr | Ala | Arg | Tyr | Met 220 | Ser | Ile | Asn Thr |
| His 225 | Phe | Gly | Arg | Glu | Gln 230 | Ser | Arg | Arg | Asp | Asp 235 | Leu | Glu | Ser | Leu Gly 240 |
| His | Val | Phe | Phe | Tyr 245 | Phe | Leu | Arg | Gly | Ser 250 | Leu | Pro | Trp | Gln | Gly Leu 255 |
| Lys | Ala | Pro | Asn 260 | Asn | Lys | Leu | Lys | Tyr 265 | Glu | Lys | Ile | Gly | Met 270 | Thr Lys |
| Gln | Lys | Leu 275 | Asn | Pro | Asp | Asp | Leu 280 | Leu | Leu | Asn | Asn | Ala 285 | Ile | Pro Tyr |
| Gln | Phe 290 | Ala | Thr | Tyr | Leu | Lys 295 | Tyr | Ala | Arg | Ser | Leu 300 | Lys | Phe | Asp Glu |
| Asp 305 | Pro | Asp | Tyr | Asp | Tyr 310 | Leu | Ile | Ser | Leu | Met 315 | Asp | Asp | Ala | Leu Arg 320 |
| Leu | Asn | Asp | Leu | Lys 325 | Asp | Asp | Gly | His | Tyr 330 | Asp | Trp | Met | Asp | Leu Asn 335 |
| Gly | Gly | Lys | Gly 340 | Trp | Asn | Ile | Lys | Ile 345 | Asn | Arg | Arg | Ala | Asn 350 | Leu His |
| Gly | Tyr | Gly 355 | Asn | Pro | Asn | Pro | Arg 360 | Val | Asn | Gly | Asn | Thr 365 | Ala | Arg Asn |
| Asn | Val 370 | Asn | Thr | Asn | Ser | Lys 375 | Thr | Arg | Asn | Thr | Thr 380 | Pro | Val | Ala Thr |
| Pro 385 | Lys | Gln | Gln | Ala | Gln 390 | Asn | Ser | Tyr | Asn | Lys 395 | Asp | Asn | Ser | Lys Ser 400 |
| Arg | Ile | Ser | Ser | Asn 405 | Pro | Gln | Ser | Phe | Thr 410 | Lys | Gln | Gln | His | Val Leu 415 |

```
Lys  Lys  Ile  Glu  Pro  Asn  Ser  Lys  Tyr  Ile  Pro  Glu  Thr  His  Ser  Asn
          420                      425                     430

Leu  Gln  Arg  Pro  Ile  Lys  Ser  Gln  Ser  Gln  Thr  Tyr  Asp  Ser  Ile  Ser
          435                      440                     445

His  Thr  Gln  Asn  Ser  Pro  Phe  Val  Pro  Tyr  Ser  Ser  Ser  Lys  Ala  Asn
     450                      455                     460

Pro  Lys  Arg  Ser  Asn  Asn  Glu  His  Asn  Leu  Pro  Asn  His  Tyr  Thr  Asn
465                      470                     475                          480

Leu  Ala  Asn  Lys  Asn  Ile  Asn  Tyr  Gln  Ser  Gln  Arg  Asn  Tyr  Glu  Gln
               485                      490                          495

Glu  Asn  Asp  Ala  Tyr  Ser  Asp  Asp  Glu  Asn  Asp  Thr  Phe  Cys  Ser  Lys
               500                      505                     510

Ile  Tyr  Lys  Tyr  Cys  Cys  Cys  Cys  Phe  Cys  Cys  Cys
          515                 520
```

( 2 ) INFORMATION FOR SEQ ID NO:25:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( v i i ) IMMEDIATE SOURCE:
        ( B ) CLONE: Protein Kinase ( i x ) FEATURE:
        ( A ) NAME/KEY: Peptide
        ( B ) LOCATION: 1..6

( x i ) SEQUENCE DESCRIPTION: SEQ ID NO:25:

```
Gly  Pro  Ser  Leu  Glu  Asp
 1                    5
```

( 2 ) INFORMATION FOR SEQ ID NO:26:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( v i i ) IMMEDIATE SOURCE:
        ( B ) CLONE: Protein Kinase ( i x ) FEATURE:
        ( A ) NAME/KEY: Peptide
        ( B ) LOCATION: 1..9

( x i ) SEQUENCE DESCRIPTION: SEQ ID NO:26:

```
Arg  Asp  Ile  Lys  Pro  Asp  Asn  Phe  Leu
 1                    5
```

( 2 ) INFORMATION FOR SEQ ID NO:27:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( v i i ) IMMEDIATE SOURCE:
        ( B ) CLONE: Protein Kinase ( i x ) FEATURE:
  ( A ) NAME/KEY: Peptide
  ( B ) LOCATION: 1..6

( x i ) SEQUENCE DESCRIPTION: SEQ ID NO:27:

His Ile Pro Tyr Arg Glu
1               5